(12) United States Patent
Nagarathnam et al.

(10) Patent No.: US 7,648,986 B2
(45) Date of Patent: Jan. 19, 2010

(54) SUBSTITUTED THIENO[3,2-D]PYRIMIDINES AS RHO KINASE INHIBITORS

(75) Inventors: Dhanapalan Nagarathnam, Bethany, CT (US); Uday Khire, Hamden, CT (US); Davoud Asgari, Plainsboro, NJ (US); Jianxing Shao, Cheshire, CT (US); Xiao-Gao Liu, New Haven, CT (US); Chunguang Wang, Hamden, CT (US); Barry Hart, Mountain View, CA (US); Olaf Weber, Woodbridge, CT (US); Mark Lynch, Madison, CT (US); Lei Zhang, Hamden, CT (US); Lei Wang, New Haven, CT (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 11/733,045

(22) Filed: Apr. 9, 2007

(65) Prior Publication Data

US 2007/0238741 A1 Oct. 11, 2007

Related U.S. Application Data

(63) Continuation of application No. 10/339,393, filed on Jan. 10, 2003, now abandoned.

(60) Provisional application No. 60/346,628, filed on Jan. 10, 2002.

(51) Int. Cl.
| | |
|---|---|
| C07D 495/04 | (2006.01) |
| C07D 251/16 | (2006.01) |
| C07D 413/10 | (2006.01) |
| A61K 31/519 | (2006.01) |
| A61K 31/5377 | (2006.01) |
| A61K 31/53 | (2006.01) |
| A61K 31/497 | (2006.01) |
| A61K 31/496 | (2006.01) |
| A61K 31/498 | (2006.01) |
| A61P 9/12 | (2006.01) |
| A61P 9/10 | (2006.01) |
| A61P 35/04 | (2006.01) |
| A61P 11/06 | (2006.01) |
| C07D 401/12 | (2006.01) |
| C07D 401/14 | (2006.01) |

(52) U.S. Cl. ............... 514/234.2; 514/252.16; 514/245; 514/260.1; 514/255.05; 514/264.11; 544/117; 544/211; 544/278; 544/284

(58) Field of Classification Search ............... 544/117, 544/211, 278; 514/234.2, 252.16, 245, 260.1, 514/255.05
See application file for complete search history.

(56) References Cited

U.S. PATENT DOCUMENTS

| | | | |
|---|---|---|---|
| 4,642,347 A | 2/1987 | Kreft, III et al. | |
| 4,952,567 A | 8/1990 | DeMeyts et al. | |
| 5,240,940 A | 8/1993 | Arnold et al. | |
| 5,245,036 A | 9/1993 | Robey et al. | |
| 5,324,839 A | 6/1994 | Clemence et al. | |
| 5,478,938 A | 12/1995 | Clemence et al. | |
| 5,817,674 A | 10/1998 | Clemence et al. | |
| 5,840,695 A | 11/1998 | Frank et al. | |
| 5,885,803 A | 3/1999 | Bandman et al. | |
| 5,906,819 A | 5/1999 | Kaibuchi et al. | |
| 5,932,470 A | 8/1999 | Frank et al. | |
| 5,958,944 A | 9/1999 | Arita et al. | |
| 5,972,598 A | 10/1999 | Chaudhary et al. | |
| 5,977,102 A | 11/1999 | Himmelsbach et al. | |
| 6,004,979 A | 12/1999 | Clemence et al. | |
| 6,153,617 A | 11/2000 | Bridges | |
| 6,184,226 B1 | 2/2001 | Chakravarty et al. | |
| 6,207,148 B1 | 3/2001 | Bandman et al. | |
| 6,218,410 B1 | 4/2001 | Uehata et al. | |
| 6,277,989 B1 | 8/2001 | Chakravarty et al. | |
| 6,326,373 B1 | 12/2001 | Uckun et al. | |
| 6,391,874 B1 | 5/2002 | Cockerill et al. | |
| 2001/0014679 A1 | 8/2001 | Tang et al. | |
| 2001/0044442 A1 | 11/2001 | Uckun et al. | |
| 2002/0055514 A1 | 5/2002 | Uckun et al. | |

FOREIGN PATENT DOCUMENTS

| | | |
|---|---|---|
| EP | 1 034 793 A1 | 9/2000 |
| EP | 1 163 910 A1 | 12/2001 |
| EP | 1 174 150 A1 | 1/2002 |
| EP | 1 177 796 A1 | 2/2002 |
| WO | 96/40142 | 12/1996 |
| WO | 97/03069 A1 | 1/1997 |

(Continued)

OTHER PUBLICATIONS

English Abstract of WO 95/28387 (US 5,598,994), Date: Oct. 26, 1995.

(Continued)

*Primary Examiner*—James O Wilson
*Assistant Examiner*—Susanna Moore
(74) *Attorney, Agent, or Firm*—Millen, White, Zelano, Branigan, P.C.

(57) ABSTRACT

Disclosed are compounds and derivatives thereof their synthesis, and their use as Rho-kinase inhibitors. These compounds of the present invention are useful for inhibiting tumor growth, treating erectile dysfunction, and treating other indications mediated by Rho-kinase, e.g., coronary heart disease.

8 Claims, No Drawings

FOREIGN PATENT DOCUMENTS

| | | |
|---|---|---|
| WO | 98/02434 A1 | 1/1998 |
| WO | 98/02438 | 1/1998 |
| WO | 99/23113 A2 | 5/1999 |
| WO | 99/24440 | 5/1999 |
| WO | 99/35132 A1 | 7/1999 |
| WO | 99/35146 A1 | 7/1999 |
| WO | 99/65908 A1 | 12/1999 |
| WO | 00/12497 A2 | 3/2000 |
| WO | 00/13497 | 3/2000 |
| WO | WO 00/39101 A1 | 7/2000 |
| WO | 00/55162 A2 | 9/2000 |
| WO | 00/57914 A1 | 10/2000 |
| WO | 01/09134 A1 | 2/2001 |
| WO | WO 01/28561 A1 | 4/2001 |
| WO | 02/24667 A1 | 3/2002 |
| WO | 02/30465 A2 | 4/2002 |
| WO | 02/053143 A2 | 7/2002 |

OTHER PUBLICATIONS

English Abstract of WO00/57914, Date: Oct. 5, 2000.
Chemical Abstract No. 117:251318p "Novel piperazinyl-substituted pyrimidines as antihypertensive and vasodilators", 1992.
Hu, Erding et al., Expert Opinion, Ther. Targets, 9(4) 2005, pp. 715-736.
Klebl, Bert M. et al., Expert Opinion, Ther. Targets, 9(5) 2005, pp. 975-993.

SUBSTITUTED THIENO[3,2-D]PYRIMIDINES AS RHO KINASE INHIBITORS

This application is a continuation of U.S. Ser. No. 10/339,393, filed Jan. 10, 2003 (now abandoned), which claimed benefits of U.S. Provisional Application 60/346,628, filed Jan. 10, 2002, and is hereby incorporated by reference.

FIELD OF THE INVENTION

The present invention relates to compounds and derivatives thereof, their synthesis, and their use as Rho-kinase inhibitors. These compounds of the present invention are useful for inhibiting tumor growth, treating erectile dysfunction, and treating other indications mediated by Rho-kinase, e.g., coronary heart disease.

BACKGROUND

The pathology of a number of human and animal diseases including hypertension, erectile dysfunction, coronary cerebral circulatory impairments, neurodegenerative disorders and cancer can be linked directly to changes in the actin cytoskeleton. These diseases pose a serious unmet medical need. The actin cytoskeleton is composed of a meshwork of actin filaments and actin-binding proteins found in all eukaryotic cells. In smooth muscle cells the assembly and disassembly of the actin cytoskeleton is the primary motor force responsible for smooth muscle contraction and relaxation. In non-muscle cells, dynamic rearrangements of the actin cytoskeleton are responsible for regulating cell morphology, cell motility, actin stress fiber formation, cell adhesion and specialized cellular functions such as neurite retraction, phagocytosis or cytokinesis (Van Aelst, et al. *Genes Dev* 1997, 11, 2295).

The actin cytoskeleton is controlled by a family of proteins that are a subset of the Ras superfamily of GTPases. This subset currently consists of RhoA through E and RhoG (refereed to collectively as Rho), Rac 1 and 2, Cdc42Hs and G25K and TC10 isoforms (Mackay, et al. *J Biol Chem* 1998, 273, 20685). These proteins are GTP (guanine nucleotide triphosphate) binding proteins with intrinsic GTPase activity. They act as molecular switches and cycles between inactive GDP (guanine nucleotide diphosphate) bound and active GTP bound states. Using biochemical and genetic manipulations, it has been possible to assign functions to each family member. Upon activation the Rho proteins controls the formation of actin stress fibers, thick bundles of actin filaments, and the clustering of integrins at focal adhesion complexes. When activated the Rac proteins control the formation of lamellopodia or membrane ruffles on the cell surface and Cdc42 controls filopodia formation. Together this family of proteins plays a critical part in the control of key cellular functions including cell movement, axonal guidance, cytokinesis, and changes in cell morphology, shape and polarity.

Depending on the cell type and the activating receptor, the Rho proteins can control different biological responses. In smooth muscle cells, Rho proteins are responsible for the calcium sensitization during smooth muscle contraction. In non-smooth muscle cells the Rho GTPases are responsible for the cellular responses to agonist such as lysophosphatidic acid (LPA), thrombin and thromboxane $A_2$ (Fukata, et al. *Trends Pharcol Sci* 2001, 22, 32). Agonist response is coupled through heterotrimeric G proteins $G_{alpha12}$ or $G_{alpha13}$ (Goetzl, et al. *Cancer Res* 1999, 59, 4732; Buhl, et al. *J Biol Chem* 1995, 270, 24631) though other receptors may be involved.

Upon activation Rho GTPases activate a number of downstream effectors including PIP5-kinase, Rhothekin, Rhophilin, PKN and Rho kinase isoforms ROCK-1/ROKbeta and ROCK-1/ROKalpha (Mackay and Hall *J Biol Chem* 1998, 273, 20685; Aspenstrom *Curr Opin Cell Biol* 1999, 11, 95; Amano, et al. *Exp Cell Res* 2000, 261, 44).

Rho kinase was identified as a RhoA interacting protein isolated from bovine brain (Matsui, et al. *Embo J* 1996, 15, 2208). It is a member of the myotonic dystrophy family of protein kinase and contains a serine/threonine kinase domain at the amino terminus, a coiled-coil domain in the central region and a Rho interaction domain at the carboxy terminus (Amano, et al. *Exp Cell Res* 2000, 261, 44). Its kinase activity is enhanced upon binding to GTP-bound RhoA and when introduced into cells, it can reproduce many of the activities of activated RhoA. In smooth muscle cells Rho kinase mediates calcium sensitization and smooth muscle contraction and inhibition of Rho kinase blocks 5-HT and phenylephrine agonist induced muscle contraction. When introduced into non-smooth muscle cells, Rho kinase induces stress fiber formation and is required for the cellular transformation mediated by RhoA (Sahai, et al. *Curr Biol* 1999, 9, 136). Rho kinase regulates a number of downstream proteins through phosphorylation, including myosin light chain (Somlyo, et al. *J Physiol (Lond)* 2000, 522 Pt 2, 177), the myosin light chain phosphatase binding subunit (Fukata, et al. *J Cell Biol* 1998, 141, 409) and LIM-kinase 2 (Sumi, et al. *J Bio Chem* 2001, 276, 670).

Inhibition of Rho kinase activity in animal models has demonstrated a number of benefits of Rho kinase inhibitors for the treatment of human diseases. Several patents have appeared claiming (+)-trans-4-(1-aminoethyl)-1-(pyridin-4-ylaminocarbonyl)cyclohexane dihydrochloride monohydrate (WO-00078351, WO-00057913) and substituted isoquinolinesulfonyl (EP-00187371) compounds as Rho kinase inhibitors with activity in animal models. These include models of cardiovascular diseases such as hypertension (Ucehata, et al. *Nature* 1997, 389, 990), atherosclerosis (Retzer, et al. *FEBS Lett* 2000, 466, 70), restenosis (Eto, et al. *Am J Physiol Heart Circ Physiol* 2000, 278, H1744; Negoro, et al. *Biochem Biophys Res Commun* 1999, 262, 211), cerebral ischemia (Uehata, et al. *Nature* 1997, 389, 990; Seasholtz, et al. *Circ Res* 1999, 84, 1186; Hitomi, et al. *Life Sci* 2000, 67, 1929; Yamamoto, et al. *J Cardiovasc Pharmacol* 2000, 35, 203), cerebral vasospasm (Sato, et al. *Circ Res* 2000, 87, 195; Kim, et al. *Neurosurgery* 2000, 46, 440), penile erectile dysfunction (Chitaley, et al. *Nat Med* 2001, 7, 119), central nervous system disorders such as neuronal degeneration and spinal cord injury (Hara, et al. *J Neurosurg* 2000, 93, 94; Toshima, et al. *Stroke* 2000, 31, 2245) and in neoplasias where inhibition of Rho kinase has been shown to inhibit tumor cell growth and metastasis (Itoh, et al. *Nat Med* 1999, 5, 221; Somlyo, et al. *Biochem Biophys Res Commun* 2000, 269, 652), angiogenesis (Uchida, et al. *Biochem Biophys Res Commun* 2000, 269, 633; Gingras, et al. *Biochem J* 2000, 348 Pt 2, 273), arterial thrombotic disorders such as platelet aggregation (Klages, et al. *J Cell Biol* 1999, 144, 745; Retzer, et al. *Cell Signal* 2000, 12, 645) and leukocyte aggregation (Kawaguchi, et al. *Eur J Pharmacol* 2000, 403, 203; Sanchez-Madrid, et al. *Embo J* 1999, 18, 501), asthma (Setoguchi, et al. *Br J Pharmacol* 2001, 132, 111; Nakahara, et al. *Eur J Pharmacol* 2000, 389, 103), regulation of intraoccular pressure (Honjo, et al. *Invest Opthalmol V is Sci* 2001, 42, 137) and bone resorption (Chellaiah, et al. *J Biol Chem* 2000, 275, 11993; Zhang, et al. *J Cell Sci* 1995, 108, 2285).

The inhibition of Rho kinase activity in patients has benefits for controlling cerebral vasospasms and ischemia following subarachnoid hemorrhage (*Pharma Japan* 1995, 1470, 16).

SUMMARY OF THE INVENTION

The compounds and their derivatives presented in this invention are useful as Rho Kinase inhibitors and thus have utilities in the treatment of hypertension, atherosclerosis, restenosis, cerebral ischemia, cerebral vasospasm, neuronal degeneration, spinal cord injury, cancers of the breast, colon, prostate, ovaries, brain and lung and their metastases, thrombotic disorders, asthma, glaucoma and osteoporosis.

In addition, the compounds of the invention are useful to treat erectile dysfunction, i.e., erectile dysfunction mediated by Rho-kinase. Erectile dysfunction can be defined as an inability to obtain or sustain an erection adequate for intercourse, WO 94/28902, U.S. Pat. No. 6,103,765 and U.S. Pat. No. 6,124,461.

The invention provides compounds of formula I

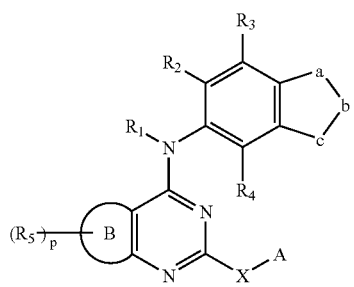

I wherein X is $-(CH_2)_x-$, $-O-(CH_2)_n-$, $-S-(CH_2)_n-$, $-NR_7-CO-(CH_2)_n-$, $-NR_7-SO_2-(CH_2)_n-$, $-NR_7-(CH_2)_n-$, or $-(O)C-NR_7-$, each n is an integer which is independently 0, 1, 2 or 3, x is 0-3 p is 0-3 a and c are each independently $-CR_5=$, $-N=$, or $-NR_6-$, wherein one of a or c is $-NR_6-$, and b is $-CR_5=$ or $-N=$;

A is H, halogen, $-CO-OR_8$, $-CO-R_8$, cyano, $-OR_8$, $-NR_8R_9$, $-CO-NR_8R_9$, $-NR_8-CO-R_9$, $-NR_8-CO-OR_9$, $-NR_8-SO_2-R_9$, $-SR_8$, $-SO_2-R_8$, $-SO_2-NR_8R_9$, $NR_8-CO-NHR_9$, or A is a 3-20 atom, preferably 5-15 atom, cyclic or polycyclic moiety, e.g., containing 1-4 rings, which optionally contain 1-3 N, O or S atoms per ring, and may optionally be aryl or heteroaryl. A may optionally be substituted up to 3 times by (i) $C_1$-$C_{10}$ alkyl or $C_2$-$C_{10}$-alkenyl, each optionally substituted with halogen up to perhalo; (ii) $C_3$-$C_{10}$ cycloalkyl; (iii) optionally substituted aryl; (iv) optionally substituted heteroaryl; (v) halogen; (vi) $-CO-OR_8$; (vii) $-CO-R_8$; (viii) cyano; (ix)$-OR_8$, (x) $-NR_8R_{13}$; (xi) nitro; (xii) $-CO-NR_8R_9$; (xiii) $-C_{1-10}$-alkyl-$NR_8R_9$; (xiv) $-NR_8-CO-R_{12}$; (xv) $-NR_8-CO-OR_9$; (xvi) $-NR_8-SO_2-R_9$;

(xvii) $-SR_8$; (xviii) $-SO_2-R_8$; (xix) $-SO_2-NR_8R_9$; or (xx) $NR_8-CO-NHR_9$;

Ring B represents a fused 5- or 6-membered heterocyclic ring containing 1-2 O, N, and/or S atoms and 1-5 C atoms.

$R_1$, and $R_6$-$R_{11}$ are each independently H and $C_{1-6}$ alkyl, $R_2$-$R_5$ are each independently (i) $C_{1-10}$ alkyl or $C_{2-10}$-alkenyl each optionally substituted by amino, N-lower alkylamino, N,N-dilower alkylamino, N-lower alkanoylamino, hydroxy, cyano, $-COOR_{10}$, $-COR_{14}$, $-OCOR_{14}$, $-OR_{10}$, $C_{5-10}$-heteroaryl, $C_{5-10}$-heteroaryloxy, $C_{5-10}$-heteroaryl-$C_{1-10}$-alkoxy, or halogen up to perhalo; (ii) $C_3$-$C_{10}$ cycloalkyl, in which 1-3 carbon atoms are optionally independently replaced by O, N or S; (iii) $C_{3-10}$-cycloalkenyl; (iv) partially unsaturated $C_{5-10}$-heterocyclyl; (v) aryl; (vi) heteroaryl; (vii) halogen; (viii) $-CO-OR_{10}$; (ix)-$OCOR_{10}$; (x) $-OCO_2R_{10}$; (xi) $-CHO$; (xii) cyano; (xiii) $-OR_{16}$; (xiv) $-NR_{10}R_{15}$; (xv) nitro; (xvi) $-CO-NR_{10}R_{11}$; (xvii) $-NR_{10}-CO-R_{12}$; (xviii) $-NR_{10}-CO-OR_{11}$; (xix) $-NR_{10}-SO_2-R_{12}$; (xx) $-SR_{16}$; (xxi) $-SOR_{16}$; (xxii) $-SO_2-R_{16}$; (xxiii) $-SO_2-NR_{10}R_{11}$; (xxiv) $NR_{10}-CO-NHR_{11}$; (xxv) amidino; (xxvi) guanidino; (xxvii) sulfo; (xxviii) $-B(OH)_2$; (xxix) $-OCON(R_{10})_2$; or (xxx) $-NR_{10}CON(R_{10})_2$;

$R_{12}$ is H, $C_{1-6}$-alkyl or $C_{5-10}$-aryl, $R_{13}$ is H, $C_{1-6}$-alkyl or $C_{1-6}$-alkoxy, $R_{14}$ is lower alkyl or phenyl;

$R_{15}$ is lower alkyl, halogen, amino, N-lower alkyl amino, N,N-dilower alkylamino, N-lower alkanoylamino, OH, CN, $COOR_{10}$, $-COR_{14}$ or $-OCOR_{14}$;

$R_{16}$ is hydrogen, $C_{1-6}$-alkyl optionally substituted by halogen, up to perhalo, or $C_{5-10}$-heteroaryl; and with the provisos that A is not hydrogen when x is 0;

—X-A is not $CH_3$ when B represents a thieno[3,2b]fused ring, and b and c are $-CR_5=$, and a is NH;

and A is not phenyl when X is NH, B forms an imidazo fused ring, and -a-b-c- is $-CR_5=N-NR_6-$ or $-NR_6=N-CR_5-$.

In formula I, suitable aryl or heteroaryl groups, e.g., for A, include, but are not limited to, 5-12 carbon-atom aromatic rings or ring systems containing 1-3 rings, at least one of which is aromatic, in which one or more, e.g., 1-4 carbon atoms in one or more of the rings can be replaced by oxygen, nitrogen or sulfur atoms. Each ring typically has 3-7 atoms. For example, aryl or heteroaryl can be 2- or 3-furyl, 2- or 3-thienyl, 2- or 4-triazinyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl; 1,2,3-triazol-1-, -4- or 5-yl, 1,2,4-triazol-1-, -3- or 135-yl, 1- or 5-tetrazolyl, 1,2,3-oxadiazol-4- or 5-yl, 1,2,4-oxadiazol-3- or 5-yl, 1,3,4-thiadiazol-2- or 5-yl, 1,2,4-oxadiazol-3- or 5-yl, 1,3,4-thiadiazol-2- or 5-yl, 1,3,4-thiadiazol-3- or 5-yl, 1,2,3-thiadiazol-4- or 5-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5- 6- or 7-benzisoxazolyl, 1-, 3-, 4-, 5-, 6- or 7-benzothiazolyl, 2-, 4-, 5-, 6- or 7-benzisothiazolyl, 2-, 4-, 5-, 6- or 7-benz-1,3-oxadiazolyl, 2-, 3-, 4-, 5-, 6-, 7- or 8-quinolinyl, 1-, 3-, 4-, 5-, 6-, 7-, 8-isoquinolinyl, 1-, 2-, 3-, 4- or 9-carbazolyl, 1-, 2-, 3-, 4-, 5-, 6-, 7-, 8- or 9-acridinyl, or 2-, 4-, 5-, 6-, 7- or 8-quinazolinyl, or additionally optionally substituted phenyl, 2- or 3-thienyl, 1,3,4-thiadiazolyl, 3-pyrryl, 3-pyrazolyl, 2-thiazolyl or 5-thiazolyl, etc.

Preferred moieties A include cyclohexyl; or $C_{5-12}$-aryl or $C_{5-12}$-heteroaryl each independently optionally substituted up to three times by (i) $C_1$-$C_{10}$-alkyl or $C_{2-10}$-alkenyl each optionally substituted with halogen up to perhalo; (ii) $C_3$-$C_{10}$ cycloalkyl; (iii) $C_{5-12}$-aryl optionally substituted by 1-3 halogen atoms; (iv) $C_{5-12}$-heteroaryl; (v) halogen; (vi) —CO—$OR_8$; (vii) —CO—$R_8$; (viii) cyano; (ix) —$OR_8$; (x) —$NR_8R_{13}$; (xi) nitro; (xii) —CO—$NR_8R_9$; (xiii) —$C_{1-10}$-alkyl-$NR_8R_9$; (xiv) —$NR_8$—CO—$R_{12}$; (xv) —$NR_8$—CO—$OR_9$; (xvi) —$NR_8$—$SO_2$—$R_9$; (xvii) —$SR_8$; (xviii) —$SO_2$—$R_8$; (xix) —$SO_2$—$NR_8R_9$, or (xx) $NR_8$—CO—$NHR_9$.

Further preferred moieties A include phenyl, pyridyl, pyrimidinyl, oxazolyl, furyl, thienyl, pyrrolyl, imidazolyl, isoxazolyl and pyrazinyl, each independently substituted up to three times by halogen, $C_{1-10}$-alkyl, $C_{1-10}$-alkoxyphenyl, naphthyl, —$OR_{10}$,

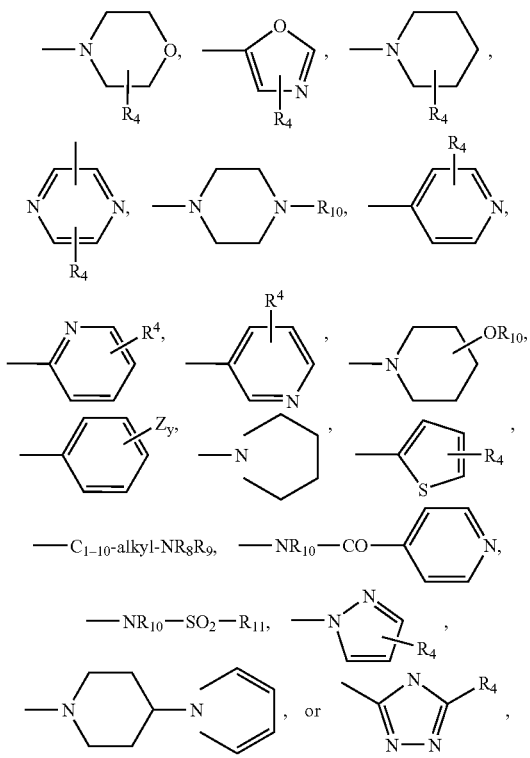

as well as

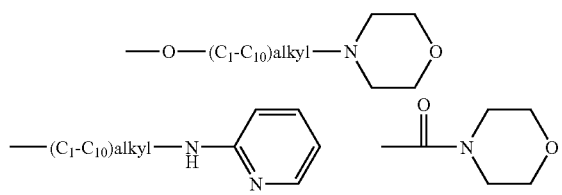

wherein each Z independently is halogen, hydroxy, hydroxy-$C_{1-10}$-alkyl, —CN, —$NO_2$, $C_{1-10}$-alkoxycarboxyl, —$NR_{10}$—CO—$R_{11}$, or —$NR_{10}$—CO—$OR_{11}$, as well as $OR_{10}$,
y is 0-3, more preferably 1-3,
and $R_4$ is as described above.

Preferred moieties A additionally include

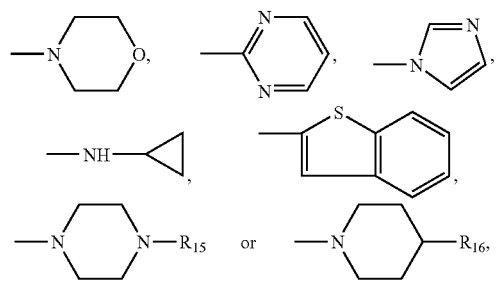

as well as wherein $R_{15}$ is H; phenyl optionally substituted by $C_{1-10}$-alkyl, $C_{1-10}$-alkoxy, $C_{1-10}$-alkylcarboxyl, or halogen; benzyl; pyrimidyl or pyridyl; and $R_{16}$ is H, phenyl, —$COOR_{10}$, The present invention is also directed to pharmaceutically acceptable salts of formula I. Suitable pharmaceutically acceptable salts are well known to those skilled in the art and include basic salts of inorganic and organic acids, such as hydrochloric acid, hydrobromic acid, sulphuric acid, phosphoric acid, methanesulphonic acid, sulphonic acid, acetic acid, trifluoroacetic acid, malic acid, tartaric acid, citric acid, lactic acid, oxalic acid, succinic acid, fumaric acid, maleic acid, benzoic acid, salicyclic acid, phenylacetic acid, and mandelic acid. In addition, pharmaceutically acceptable salts include acid salts of inorganic bases, such as salts containing alkaline cations (e.g., $Li^+$, $Na^+$ or $K^+$), alkaline earth cations (e.g., $Mg^+$, $Ca^+$ or $Ba^+$), the ammonium cation, as well as acid salts of organic bases, including aliphatic and aromatic substituted ammonium, and quaternary ammonium cations, such as those arising from protonation or peralkylation of triethylamine, N,N-diethylamine, N,N-dicyclohexylamine, pyridine, N,N-dimethylaminopyridine (DMAP), 1,4-diazabiclo[2.2.2]octane (DABCO), 1,5-diazabicyclo[4.3.0]non-5-ene (DBN) and 1,8-diazabicyclo[5.4.0]undec-7-ene (DBU).

A number of the compounds of Formula I possess asymmetric carbons and can therefore exist in racemic and optically active forms. Methods of separation of enantiomeric and diastereomeric mixtures are well known to one skilled in the art. The present invention encompasses any isolated racemic or optically active form of compounds described in Formula I which possess Rho-kinase inhibitory activity.

The invention also includes pharmaceutical compositions including a compound of Formula I, and a physiologically acceptable carrier.

The invention moreover encompasses treating indications mediated by Rho-kinase, by administering a compound of Formula I, or a pharmaceutical composition containing a compound of Formula I. Thus, the invention encompasses treating cardiovascular diseases such as hypertension, artheroselerosis, restenosis and cerebral ischemia, or vasospasm central nervous system disorders such as neuronal degeneration and spinal cord injury, erectile dysfunction, e.g., in patients who do not have satisfactory response to PDE-5 inhibitors, and cancer (e.g., tumor growth) mediated by Rho-kinase, by administering, e.g., to a host in need thereof, of an effective amount of a compound of Formula I. Cancers and tumors mediated by Rho-kinase include cancers of the breast, colon, prostate, ovaries, brain and lung and their metastases.

A number of the compounds of Formula I possess asymmetric carbons and can therefore exist in racemic and optically active forms. Methods of separation of enantiomeric and diastereomeric mixtures are well known to one skilled in the art. The present invention encompasses any isolated racemic or optically active form of compounds described in Formula I which possess Rho-kinase inhibitory activity.

The invention also includes pharmaceutical compositions including a compound of Formula I, and a physiologically acceptable carrier.

The invention moreover encompasses treating indications mediated by Rho-kinase, by administering a compound of Formula I, or a pharmaceutical composition containing a compound of Formula I. Thus, the invention encompasses treating cardiovascular diseases such as hypertension, artheroselerosis, restenosis and cerebral ischemia, or vasospasm central nervous system disorders such as neuronal degeneration and spinal cord injury, erectile dysfunction, e.g., in patients who do not have satisfactory response to PDE-5 inhibitors, and cancer (e.g., tumor growth) mediated by Rho-kinase, by administering, e.g., to a host in need thereof, of an effective amount of a compound of Formula I. Cancers and tumors mediated by Rho-kinase include cancers of the breast, colon, prostate, ovaries, brain and lung and their metastases.

The compounds may be administered orally, topically, parenterally, by inhalation or spray, vaginally, rectally or sublingually in dosage unit formulations. The term 'administration by injection' includes intravenous, intraarticular, intramuscular, subcutaneous and parenteral injections, as well as use of infusion techniques. Dermal administration may include topical application or transdermal administration. One or more compounds may be present in association with one or more non-toxic pharmaceutically acceptable carriers and if desired other active ingredients.

Compositions intended for oral use may be prepared according to any suitable method known to the art for the manufacture of pharmaceutical compositions. Such compositions may contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. These compounds may also be prepared in solid, rapidly released form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions may also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The compounds may also be in the form of non-aqueous liquid formulations, e.g., oily suspensions which may be formulated by suspending the active ingredients in a vegetable oil, for example arachis oil, olive oil, sesame oil or peanut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Compounds of the invention may also be administrated transdermally using methods known to those skilled in the art (see, for example: Chien; "Transdermal Controlled Systemic Medications"; Marcel Dekker, Inc.; 1987. Lipp et al. WO94/04157 3 Mar. 1994). For example, a solution or suspension of a compound of Formula I in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of a compound of Formula I may be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents may also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated $C_8$-$C_{18}$ fatty alcohols such as lauryl alcohol or cetyl alcohol, saturated or unsaturated $C_8$-$C_{18}$ fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations may also include mixtures of one or more materials selected from monohydroxy or polyhydroxy alcohols, saturated or unsaturated $C_8$-$C_{18}$ fatty alcohols, saturated or unsaturated $C_8$-$C_{18}$ fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates may also be used as matrix components. Additional additives, such as viscous resins or oils may be added to increase the viscosity of the matrix.

Pharmaceutical compositions of the invention may also be in the form of oil-in-water emulsions. The oil phase may be a vegetable oil, for example olive oil or arachis oil, or a mineral oil, for example, liquid paraffin or mixtures of these. Suitable emulsifying agents may be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal temperature or vaginal temperature and will therefore melt in the rectum or vagina to release the drug. Such materials include cocoa butter and polyethylene glycols.

Moreover, for treatment of erectile dysfunction, the present pharmaceutical compositions may take any form which is suitable for administration to the penis either via injection into the corpora cavernosa or transurethral administration, or topically applied to the urethral meatus. In the case of injection into the corpora cavernosa, the pharmaceutical composition is suitably in the form of a saline solution. Preferably, the pharmaceutical composition is in a form suitable for transurethral administration, and in this case the composition is typically in the form of a solution, an ointment, or a suppository. Typically, the pharmaceutical composition is administered 1 to 50 minutes, preferably 10 to 20 minutes, prior to the time of conmmencing sexual intercourse.

For all regimens of use disclosed herein for compounds of Formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.1 to 200 mg/Kg of total body weight. The daily vaginal dosage regime will preferably be from 0.01 to 200 mg/Kg of total body weight. The daily topical dosage regimen will preferably be from 0.01 to 200 mg administered between one to four times daily. The transdermal concentration will preferably be that required to maintain a daily dose is of from 0.1 to 200 mg/Kg. The daily inhalation dosage regimen will preferably be from 0.01 to 10 mg/Kg of total body weight.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of a compound of Formula I or a pharmaceutically acceptable salt thereof given for a defined number of days, can be ascertained by those skilled in the art using conventional treatment tests.

The present compounds and compositions exhibit Rho-kinase inhibitory activity, and are thus useful to treat the indications listed above, e.g., indications mediated by Rho-kinase. By indications mediated by Rho-kinase is meant diseases or conditions whose progression proceeds, at least in part, via the Rho pathway.

Rho-kinase inhibitory activity, e.g., ROCK-1 inhibition, can be evaluated as follows:

The kinase domain of human ROCK-1, amino acids 27-530, is isolated as a glutathione S-transferase fusion protein from Sf9 insect cells. The protein is partially purified by glutathione Sepharose 4B (Pharmacia Biotech, Piscataway, N.J.) affinity purification. Reactions is carried out in 96-well plates in a total volume of 100 uL containing 50 mM N-[2-Hydroryethyl]piperaxine-N'-[2-ethanesulfonic acid] pH 7.5, 5 mM $MgCl_2$, 1 mM dithiothreitol, 6 µM ATP, 0.2 µCi [$^{33}$P] ATP (NEN, Boston, Mass.), 1 µg myelin basic protein and 0.1 µg ROCK-1. Test compounds are dissolved in 100% dimethylsulfoxide, diluted to the appropriated concentration and added to the reaction. The final concentration of dimethylsulfoxide did not exceed 0.5%. The reaction is run for one hour at room temperature. The reaction is stopped with the addition of 7 mL of 1 N HCL, transferred to P30 membranes and the amount of [$^{33}$P]ATP, as counts per minute (c.p.m.) incorporated into the substrate, myelin basic protein, is read in a BetaPlate Reader (Packard Instrument Co., Meriden, Conn.). (All reagents were purchased from Sigma Chemical Co., St. Louis, Mo. unless stated otherwise.) Percentage inhibition is measured by the amount of incorporation of radioactivity in the presence of the test compound when compared to the amount of incorporation in the absence of the test compound.

Inhibitory activity can also be evaluated by measurement of stress fiber formation, performed essentially as described by Ridley, A. J., and A. Hall, Cell 70:389-399 (1992), Human fibrosarcoma HT1080 (CCL-121, American Type Culture Collection, Manassas, Va.) cells are plated on 22×22 mm #1 glass cover slips in six-well tissue culture plates (Costar) at 2.5×10$^4$ cells/well in Delbeco's modified Eagle's Medium (DMEM, Gibco) supplemented with 10% fetal calf serum. Cells are maintained in a humidified, 5% CO$_2$ atmosphere at 37° C. After 24 hours the culture medium is removed and replaced with medium without 10% fetal calf serum and the cells cultured for an additional 48 hours. Test compounds are dissolved in 100% dimethylsulfoxide, diluted to the appropriated concentration and added to the culture medium 60 minutes prior to the induction of stress fiber formation. The final concentration of dimethylsulfoxide did not exceed 0.25%. Stress fiber formation is induced by the addition of lysophosphatidic acid (1-oleoyl-2-hydroxy-sn-glycerol-3-phosphate, Avanti Polar-Lipids, Alabaster, Ala.) to 10 μM final concentration in Delbeco's modified Eagle's Medium containing 0.1% fatty acid free bovine serum albumin for 15 minutes at 37° C. Cells are fixed with 4% paraformaldehyde (Poly Scientific, Bay Shore, N.J.) in phosphate buffered saline (PBS) for 15 minutes. Cells are then washed 3 times in PBS and them permeabilized using a solution containing 40 mM piperazine-N-N'bis[2-ethanesulfonic acid], 50 mM N-[2-hydroryethyl]piperaxine-N'-[2-ethanesulfonic acid], 0.1% Triton X-100, 75 mM NaCl, mM MgCl$_2$, 0.5 mM EBTA, pH 7.2 for 2 minutes at room temperature. The cells are washed 3 times for 5 minutes each in PBS and then actin stress fibers are stained using 10 units/mL rhodamine phalloidin (Molecular Probes, Eugene, Oreg.) in PBS for 60 minutes at room temperature. The cells are washed 3 times with PBS and the cover slips mounted on glass microscope slides. The percentage of stress fiber positive cells on each slide was determined visually using a Nikon Labphoto-2 microscope. At least 100 cells were counted per slide and experiments were done in duplicate. Percentage inhibition is measured by counting the number of stress fiber positive cells in the presence of the test compound when compared to the number of stress fiber positive cells in the absence of the test compound.

Using the above protocols, all of the compounds as disclosed herein are determined to have Rho-kinase inhibitory activity.

The compounds of the invention can be made according to routine, conventional chemical methods, and/or as disclosed below, from starting materials which are either commercially available or produceable according to routine, conventional chemical methods. General methods for the preparation of the compounds are given below, and the preparation of representative compounds is specifically illustrated in the Examples.

ABBREVIATIONS AND ACRONYMS

When the following abbreviations are used herein, they have the following meaning:

| | |
|---|---|
| Ac$_2$O | acetic anhydride |
| anhy | anhydrous |
| n-BuOH | n-butanol |
| t-BuOH | t-butanol |
| CD$_3$OD | methanol-d$_4$ |
| Celite ® | diatomaceous earth filter agent, ® Celite Corp. |
| CH$_2$Cl$_2$ | methylene chloride |
| CI-MS | chemical ionization mass spectroscopy |
| conc | concentrated |
| dec | decomposition |
| DME | dimethoxyethane |
| DMF | N,N-dimethylformamide |
| DMSO | dimethylsulfoxide |
| ELSD | evaporative light scattering detector |
| EtOAc | ethyl acetate |
| EtOH | ethanol (100%) |
| Et$_2$O | diethyl ether |
| Et$_3$N | triethylamine |
| HPLC ES-MS | high performance liquid chromatography-electrospray mass spectroscopy |
| NMM | 4-methylmorpholine |
| Ph$_3$P | triphenylphosphine |
| Pd(dppf)Cl$_2$ | [1,1'-bis(diphenylphosphino)ferrocene] dichloropalladium(II) |
| Pd(PPh$_3$)$_4$ | tetrakis(triphenylphosphine)palladium(0) |
| Pd(OAc)$_2$ | palladium acetate |
| P(O)Cl$_3$ | phosphorous oxychloride |
| RT | retention time (HPLC0) |
| rt | room temperature |
| THF | tetrahydrofuran |
| TFA | trifluoroacetic acid |
| TLC | thin layer chromatography |

General Methods of Preparation

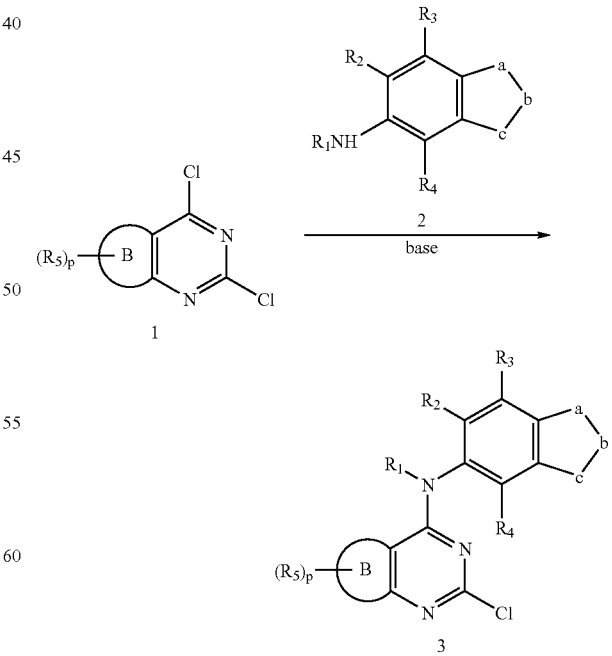

A mixture of compounds 1 and 2, and potassium acetate in THF/water is stirred at room temperature overnight. Water is added to the mixture resulting in the formation of a precipitate. The precipitate is washed with water, filtered, and dried under high vacuum to afford 3.

General Method B

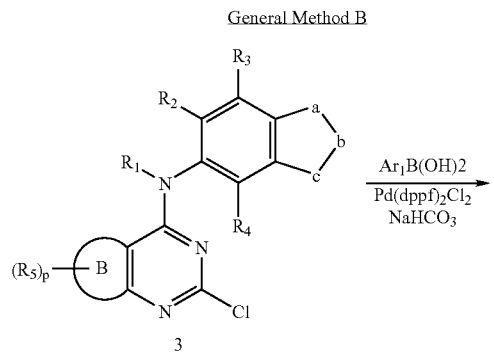

A mixture of compound 3, ethylene glycol dimethyl ether/ water, aryl boronic acid and sodium bicarbonate is degassed with argon for 15 minutes and Pd(dppf)$_2$Cl$_2$ is added. The mixture is heated to reflux overnight. After cooling to room temperature, CH$_2$Cl$_2$ and H$_2$O are added to the mixture. The organic and aqueous layers are separated and the aqueous layer is extracted with CH$_2$Cl$_2$, and the combined organic layers are dried over anhydrous sodium sulfate. The organic solvent is removed under reduced pressure and the crude product is purified by silica gel chromatography of HPLC to afford compound 4.

General Method C

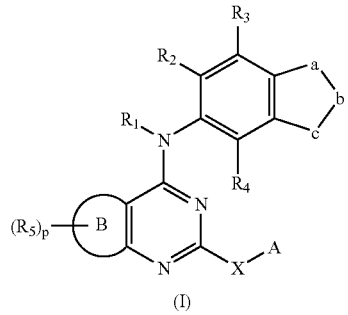

-continued

A mixture of compound 3 and a phenol, N-substituted amine, or N-substituted aniline (A-X—H, where X is O or NR$^8$) is heated to 140° C. for 2 hours. The mixture is cooled to room temperature and is treated with ether to form precipitate or purified by silica gel column chromatography. The precipitate is filtered, washed with ether several times, and is dried under high vacuum to provide product.

General Method D

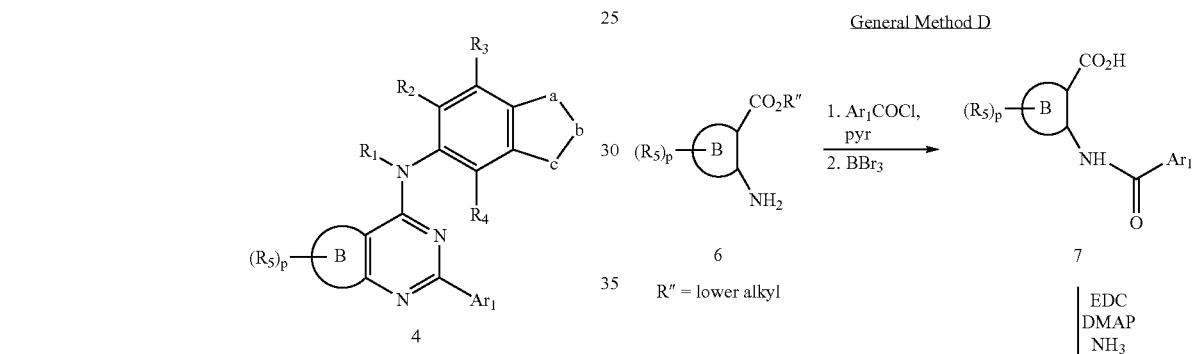

R″ = lower alkyl

A heterocyclic aminoester of Formula 6 is acylated with an aromatic acid chloride or anhydride, in a base such as pyridine. The amide ester product is converted to the amide acid of Formula 7 by hydrolysis, or if R″ is methyl, by action of boron tribromide. Conversion of the acid to the amide of Formula 8 is accomplished by reaction of 7 with ammonia in the presence of catalysts such as DMAP and EDC. Cyclization to 9 may be carried out by heating the diamide 8 in the presence of a base such as sodium hydroxide. The chloro intermediate of Formula 10 is formed by treatment of 9 with a chlorinating agent such as phosphorous oxychloride.

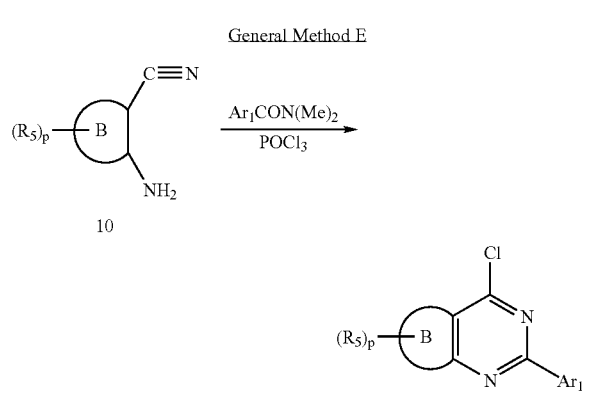

A cyanoheterocyclic amine of Formula 10 may be directly converted to compounds of Formula 4 by heating with a Vilsmeier reagent, prepared in situ by treatment of an aromatic N,N-dimethyl amide with a phosphorous oxychloride or oxalyl chloride and the like.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above or below, and of corresponding U.S. Provisional Application Ser. No. 60/277,974, filed Mar. 23, 2001, U.S. Provisional Application 60/315,341 filed Aug. 29, 2001, U.S. Provisional Application Ser. No. 60/315,338 filed Aug. 29, 2001, and U.S. Provisional Application No. 60/346,628, filed Jan. 10, 2002 are hereby incorporated by reference.

EXAMPLES

Example 1

Preparation of 2-(5-chloro-2-thienyl)-N-(1H-indazol-5-yl)thieno[3,2-d]pyrimidin-4-amine

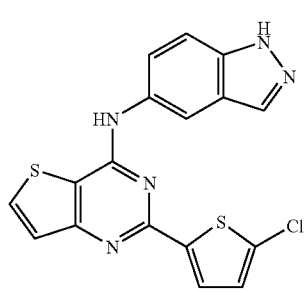

Step 1: Preparation of 2,3-dichlorothieno[3,2-d]pyrimidine

A solution of thienoyleneurea (6.0 g) and N,N-dimethylaniline (2.9 mL) in phosphorus oxychloride (35 mL) was heated at 125° C. (oil bath) for 22 h under argon. The solution cooled to 50° C. and was poured into cold water (0° C., 8.0 mL) while vigorously stirring. The precipitate was filtered, washed with water, and dissolved in EtOAc. The organic solution was filtered, washed with water, and the organic phase was dried over MgSO$_4$, filtered and concentrated to afford a yellow precipitate (4.5 g, 61% yield).

Step 2: Preparation of 4-(N-5-aminoindazole)-2-chloro-thieno[3,2-d]pyrimidine

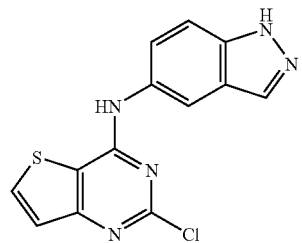

A mixture of the compound for step 1 (4.0 g, 19.5 mmol), 5-aminoindazole (3.2 g, 23.4 mmol), and potassium acetate (2.5 g, 25.4 mmol) in THF/water (100 mL/50 mL) was stirred rt overnight. The THF was removed under reduced pressure and the residue was partitioned between EtOAc and water. The organic phase was washed with aqueous NH$_4$Cl, dried over MgSO$_4$, filtered. The filtrate was poured onto a silica gel column and eluted with EtOAc. The solvent was concentrated by rotary evaporation and a gray precipitate was obtained (3.9 g, 65% yield). Rf=0.28 (EtOAc/hexanes, 1/1).

Step 3: Preparation of 2-(5-chloro-2-thienyl)-N-(1H-indazol-5-yl)thieno[3,2-d]-pyrimidin-4-amine

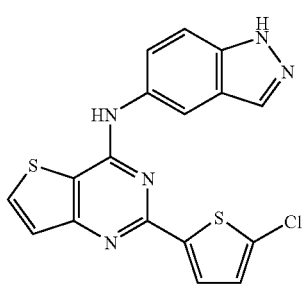

A mixture of the compound from step 2 (6.9 g, 23 mmol), 5-chlorothienyl boronic acid (3.7 g, 23 mmol) and sodium bicarbonate (5.8 g, 69 mmol) in DME/H₂O (3/1, 300 mL) was flushed with Ar for 1 h. Pd(dppf)Cl₂ (1.8 g, 2.3 mmol) was added and the mixture was heated to reflux for 48 h. The solvent was removed by rotary evaporation and the crude product was purified by silica gel chromatography to afford of yellow solid (3.5 g, 40% yield). Rf=0.20 (EtOAc/hexane, 1/1). ¹H NMR (methanol-d₄) δ 8.05 (s, 1H), 8.00 (s, 1H), 7.89 (d, 1H, J=3 Hz), 7.68-7.59 (m, 2H), 7.50 (d, 1H, J=3 Hz), 7.29 (1H, d, J=3 Hz), 6.95 (d, 1H, J=3 Hz).

Examples 2-55

Using an procedure analogous to that described for example 1 and reacting 4-(N-5-aminoindazole)-2-chlorothieno[3,2-d]pyrimidine and the appropriate boronic acid or ester, the compounds described in Table I below were prepared.

TABLE 1

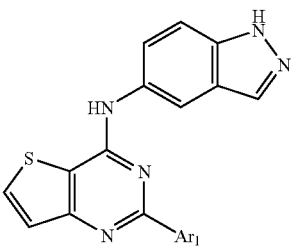

| Ex. No. | Ar₁ | Note |
|---|---|---|
| 2 | 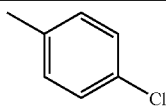 | 1 |
| 3 | 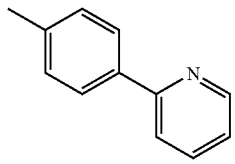 | 2 |
| 4 | 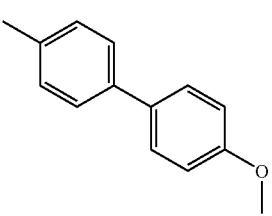 | 3 |
| 5 | 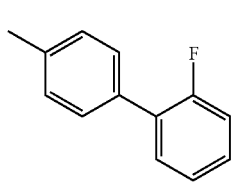 | 4 |

TABLE 1-continued

| Ex. No. | Ar₁ | Note |
|---|---|---|
| 6 | 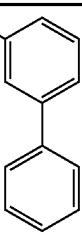 | 5 |
| 7 | 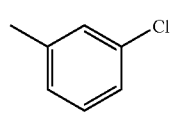 | 6 |
| 8 | 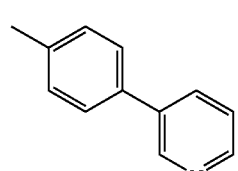 | 7 |
| 9 | 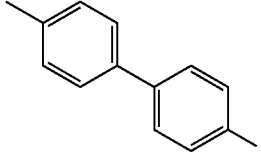 | 8 |
| 10 | 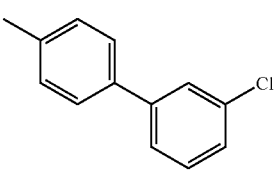 | 9 |
| 11 | 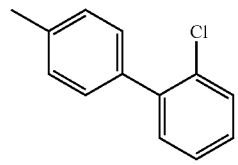 | 10 |
| 12 | 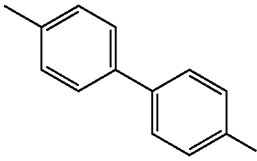 | 11 |

TABLE 1-continued
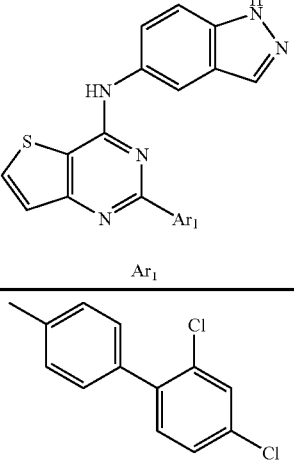
| Ex. No. | Ar₁ | Note |
|---|---|---|
| 13 | 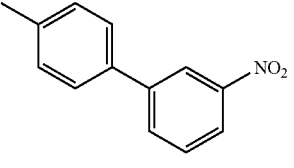 | 12 |
| 14 | 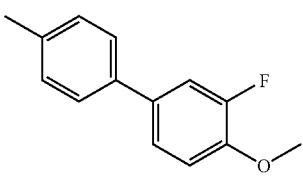 | 13 |
| 15 | 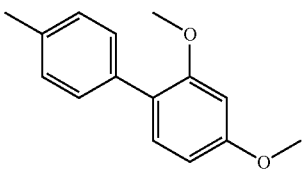 | 14 |
| 16 | 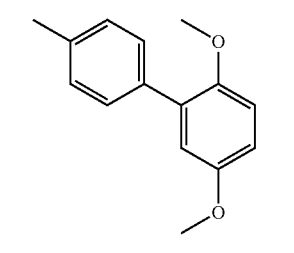 | 15 |
| 17 | 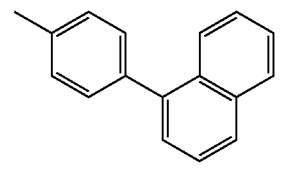 | 16 |
| 18 | 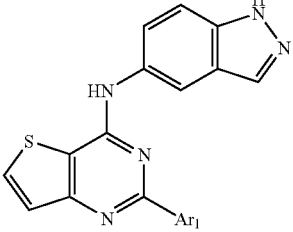 | 17 |
TABLE 1-continued
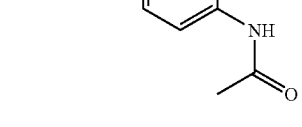
| Ex. No. | Ar₁ | Note |
|---|---|---|
| 19 |  | 18 |
| 20 | | 19 |
| 21 | | 20 |
| 22 | | 21 |
| 23 | | 22 |
| 24 | | 23 |

TABLE 1-continued

| Ex. No. | Ar₁ | Note |
|---|---|---|
| 25 | 4'-methyl-4-methoxy-3-(hydroxymethyl)biphenyl | 24 |
| 26 | 3-methyl-3-(pyridin-3-yl)phenyl | 25 |
| 27 | 2-methylbenzothiophen-2-yl | 26 |
| 28 | 5-methyl-2-methoxypyridin-3-yl | 27 |
| 29 | 5-methyl-2-phenylpyridin-3-yl | 28 |
| 30 | 4-methyl-4-(pyridin-4-yl)phenyl | 29 |
| 31 | 4-methyl-4-fluorophenyl (approx) | 30 |
| 32 | 5-methyl-2-phenylpyridin-3-yl | 31 |

TABLE 1-continued

| Ex. No. | Ar₁ | Note |
|---|---|---|
| 33 | 5-methyl-2-fluorobiphenyl | 32 |
| 34 | (5-methylthiophen-2-yl)(morpholino)methanone | 33 |
| 35 | 4-methyl-4-methoxyphenyl | 34 |
| 36 | 4-methylphenyl | 35 |
| 37 | 4-methyl-4-morpholinophenyl | 36 |
| 38 | 4'-methylbiphenyl | 37 |
| 39 | 4-methyl-2-(thieno[3,2-c]pyridin-2-yl)phenyl | 38 |
| 40 | 4-methyl-4-(piperazin-1-yl)phenyl | 39 |

TABLE 1-continued
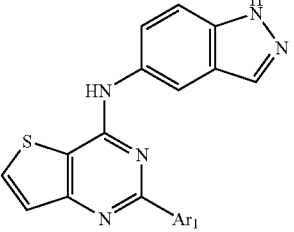
| Ex. No. | Ar₁ | Note |
|---|---|---|
| 41 | 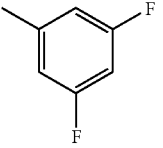 | 40 |
| 42 | 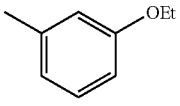 | 41 |
| 43 | 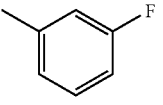 | 42 |
| 44 | 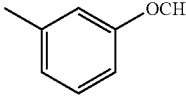 | 43 |
| 45 | 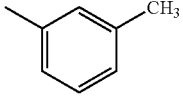 | 44 |
| 46 | 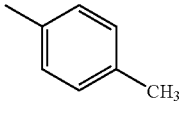 | 45 |
| 47 | 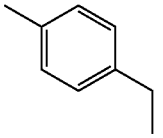 | 46 |
| 48 | 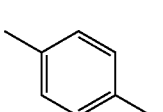 | 47 |
| 49 | 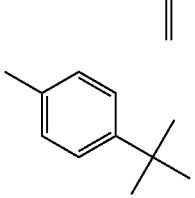 | 48 |
| 50 | 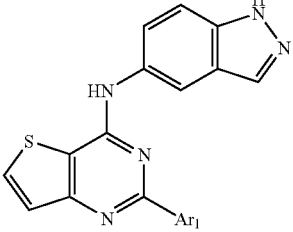 | 49 |
TABLE 1-continued
| Ex. No. | Ar₁ | Note |
|---|---|---|
| 51 | 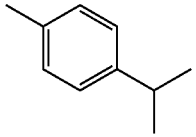 | 50 |
| 52 | 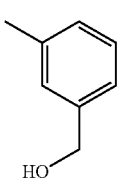 | 51 |
| 53 | 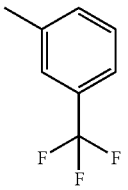 | 52 |
| 54 | 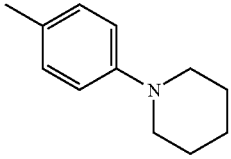 | 53 |
| 55 | 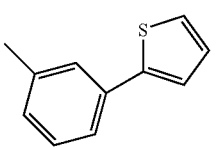 | 54 |
| 56 | | 55 |
| 57 | | 56 |

TABLE 1-continued

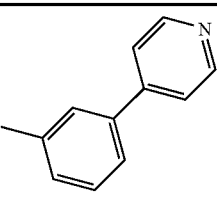

| Ex. No. | Ar₁ | Note |
|---|---|---|
| 58 | (3-(pyridin-4-yl)phenyl) | 57 |

1) HPLC/MS: (M+H)⁺ m/z 378.4. R𝑓=0.39 (50% EtOAc/Hex). ¹H NMR (DMSO): δ13.1 (s, 1H), 9.8 (s, 1H), 8.3-8.4 (m, 2H), 8.2 (d, J=5.7 Hz, 1H), 8.1 (s, 2H), 7.5-7.7 (m, 5H)

2) HPLC/MS: (M+H)⁺ m/z 421.4. R𝑓=0.25 (50% EtOAc/Hex). ¹H NMR (CD₃OD): δ8.7 (m, 1H), 8.4 (d, J=8.4 Hz, 2H), 8.2-8.3 (m, 7H), 7.6-7.7 (m, 4H)

3) HPLC/MS: (M+H)⁺ m/z 450.4. R𝑓=0.50 (1/1, EtOAc/Hex).

4) HPLC/MS: (M+H)⁺ m/z 438.4. R𝑓=0.40 (1/1, EtOAc/Hex).

5) HPLC/MS: (M+H)⁺ 420.4 m/z. R𝑓=0.33 (1/1, EtOAc/Hex). ¹H NMR (DMSO): δ13.0 (s, 1H), 9.6 (s, 1H), 8.7 (s, 1H), 8.4 (d, J=8.7, 1H), 8.3 (s, 1H), 8.2 (d, J=5.7, 1H), 8.0 (s, 1H), 7.8-7.4 (m, 10H)

6) HPLC/MS: (M+H)⁺ m/z 378.4. R𝑓=0.62 (1/1, EtOAc/Hex). ¹H NMR (DMSO and CH₂Cl₂): δ12.9 (s, 1H), 9.7 (s, 1H), 8.3-8.4 (m, 3H), 8.0-8.1 (m, 4H), 7.3-7.7 (m, 3H)

7) HPLC/MS: (M+H)⁺ m/z 421.4. R𝑓=0.24 (1/1, EtOAc/Hex). ¹H NMR (CD₃OD): δ 9.1 (s, 1H), 8.7 (m, 1H), 8.6 (dd, 1H), 8.4-8.5 (d, J=8.1 Hz, 2H), 8.3 (d, J=6.0 Hz, 1H), 8.2 (s, 1H), 8.1 (m, 1H), 8.0 (m, 2H), 7.9 (m, 1H), 7.6-7.7 (m, 2H), 7.6 (d, J=5.1, 1H)

8) HPLC/MS: (M+H)⁺ m/z 438.4. R𝑓=0.41 (1/1, EtOAc/Hex). ¹H NMR (CD₃OD): δ 8.3-8.4 (.J=8.4 Hz, 2H), 8.3 (d, J=5.4 Hz, 1H), 8.2 (s, 1H), 8.1 (s, 1H), 7.8-7.9 (d, J=8.4 Hz, 2H), 7.6-7.8 (m, 4H), 7.5-7.6 (d, J=5.4, 1H), 7.2-7.3 (m, 2H)

9) HPLC/MS: (M+H)⁺ m/z 454.4. R𝑓=0.33 (1/1, EtOAc/Hex).

10) HPLC/MS: (M+H)⁺ m/z 454.5. R𝑓=0.40 (1/1, EtOAc/Hex).

11) HPLC/MS: (M+H)⁺ m/z 454.4. R𝑓=0.42 (1/1, EtOAc/Hex).

12) HPLC/MS: (M+H)⁺ m/z 488.4. R𝑓=0.43 (1/1, EtOAc/Hex).

13) HPLC/MS: (M+H)⁺ m/z 465.4. R𝑓=0.36 (1/1, EtOAc/Hex). ¹H NMR (CD₃OD): δ 8.6 (t, J=1.8 Hz, 1H), 8.4 (d, J=8.7, 2H), 8.3 (m, 2H), 8.1-8.2 (m, 3H), 8.0 (d, J=10.5, 2H), 7.7-7.8 (m, 3H), 7.5-7.6 (d, J=5.4 Hz, 1H)

14) HPLC/MS: (M+H)⁺ m/z 468.4. R𝑓=0.38 (1/1, EtOAc/Hex).

15) HPLC/MS: (M+H)⁺ m/z 480.4. R𝑓=0.37 (1/1, EtOAc/Hex).

16) HPLC/MS: (M+H)⁺ m/z 480.4. R𝑓=0.30 (1/1, EtOAc/Hex).

17) HPLC/MS: (M+H)⁺ m/z 470.5. R𝑓=0.36 (1/1, EtOAc/Hex). ¹H NMR (CD₃OD): δ 8.3-8.4 (m, 2H, 1H), 8.2 (s, 1H), 8.1 (s, 1H), 7.9-8.0 (m, 2H), 7.8-7.9 (m, 1H), 7.7-7.8 (m, 4H), 7.4-7.6 (m, 6H)

18) HPLC/MS: (M+H)⁺ m/z 477.5. R𝑓=0.13 (1/1, EtOAc/Hex).

19) HPLC/MS: (M+H)⁺ m/z 462.5. R𝑓𝑓=0.33 (1/1, EtOAc/Hex).

20) HPLC/MS: (M+H)⁺ m/z 479.3. R𝑓=0.39 (1/1, EtOAc/Hex).

21) HPLC/MS: (M+H)⁺ m/z 434.4. Retention time (HPLC): Rt=4.73. ¹H NMR (CD₃OD): δ 8.1-8.4 (m, 6H), 7.4-7.7 (m, 7H)

22) HPLC/MS: (M+H)⁺ m/z 465.3. Retention time (HPLC, CH₃CN/H₂O/0.1% TFA): Rt=2.79

23) HPLC/MS: (M+H)⁺ m/z 426.4. Retention time (HPLC): Rt=2.55

24) HPLC/MS: (M+H)⁺ m/z 480.4. Retention time (HPLC): Rt=2.31

25) HPLC/MS: (M+H)⁺ m/z 421.4. R𝑓=0.13 (1/1, EtOAc/Hex). ¹H NMR (CD₃OD): δ 9.0 (s, 1H), 8.8 (s, 1H), 8.7 (t, J=1.8 Hz, 1H), 8.5-8.6 (m, 1H), 8.4 (m, 1H), 8.3 (d, J=6.0 Hz, 1H), 8.1 (m, 1H), 8.0 (m, 1H), 7.6-7.9 (m, 4H), 7.5-7.6 (d, J=5.7 Hz, 2H)

26) R𝑓=0.33 (CH₂Cl₂/MeOH, 95/5). ¹H NMR (CD₃OD) δ 8.2 (1H, s), 8.2 (1H, s), 8.1 (1H, s), 8.0 (1H, dd, J=1.8, 6.0 Hz), 7.9-7.8 (1H, m), 7.8-7.7 (1H, d, J=9.3 Hz), 7.7-7.6 (2H, m), 7.6-7.5 (1H, m), 7.4 (1H, dd, J=5.4, 2.1 Hz), 7.4-7.3 (1H, m).

27) R𝑓=0.33 (CH₂Cl₂/MeOH, 95/5). ¹H NMR (CD₃OD) δ 9.1 (1H, d, J=2.4 Hz), 8.6 (1H, dd, J=2.4, 8.7 Hz), 8.1-8.0 (2H, m), 8.0-7.9 (1H, d, J=5.4 Hz), 7.7 (1H, dd, J=2.2, 8.7 Hz), 7.6 (1H, d, J=8.7 Hz), 7.42 (1H, d, J=5.4 Hz), 6.8 (1H, d, J=9.3 Hz).

28) R𝑓=0.47 (Hexane/EtOAc=1/1). ¹H NMR (CD₃OD) δ 9.7 (1H, d, J=1.4 Hz), 9.2 (1H, d, J=8.7 Hz), 8.24-8.20 (2H, m), 8.1 (1H, d, J=2.2 Hz), 7.8 (1H, d, J=2.8 Hz), 7.71 (1H, d, J=1.4 Hz), 7.66-7.56 (4H, m), 7.21-7.19 (2H, m), 709-7.07 (1H, m).

29) R𝑓=0.28 (Hexane/EtOAc, 1/2). ¹H NMR (CD₃OD) δ 8.60 (2H, d, S=5.7 Hz), 8.53 (2H, dd, J=1.5, 6.9 Hz), 8.15 (1H, d, J=1.0 Hz), 8.10 (1H, d, J=2.2 Hz), 8.01 (1H, d, J=5.4 Hz), 7.88 (2H, dd, J=1.8, 6.6 Hz), 7.79 (2H, dd, J=1.8, 4.5 Hz), 7.74 (1H, dd, J=2.1, 9.0 Hz), 7.76 (1H, d, J=8.7 Hz), 7.48 (1H, d, J=6.5 Hz).

30) R𝑓=0.38 (Hexane/EtOAc, 1/1). ¹H NMR (DMSO-d₆) δ 13.08 (1H, s), 9.02 (1H, s), 8.40 (2H, dd, J=2.4, 5.7 Hz), 8.15 (1H, d, J=6.0 Hz), 8.18.-8.09 (2H, m), 7.68 (1H, dd, J=2.1, 9.3 Hz), 7.60 (1H, d, J=9.0 Hz), 7.46 (1H, d, J=5.7 Hz), 7.29 (2H, t, J=7.2 Hz)

31) ¹H NMR (DMSO-d₆) δ 11.01 (1H, s), 9.34 (1H, s), 8.72 (1H, d. J=5.7 Hz), 8.18 (1H, s), 8.12 (1H, J=6.6 Hz), 7.97-7.90 (4H, m), 7.87 (1H, s), 7.56 (1H, d, J=3.0 Hz), 7.47 (1H, d, J=6.0 Hz), 7.36-7.34 (1H, m)

32) R𝑓=0.42 (Hexane/EtOAc, 1/1). (CD₃OD) δ 8.91 (1H, d, J=6.3 Hz), 8.37 (1H, d, J=6.3 Hz), 8.30 (1H, dd, J=1.2, 9.0 Hz), 8.25 (1H, dd, J=1.5, 6.3 Hz), 8.20 (1H, d, J=0.60 Hz), 8.12 (1H, d, J=1.0 Hz), 7.86 (1H, t J=6.2 Hz), 7.80 (1H, s), 7.80-7.78 (1H, m), 7.76 (1H, d, J=1.8 Hz), 7.71 (1H, d, J=6.0 Hz), 7.65-7.62 (1H, m), 7.54-7.46 (2H, m).

33) HPLC/MS: (M+H) m/z 462, R𝑓=0.28 (EtOAc/Hexanes 10:90).

34) Purified by silica gel column chromatography (gradient, EtOAc in hexanes from 20% to 70%); Rf=0.22 (EtOAc/hexanes, 1/1); (3.18 g, 68% yield); LCMS m/z 374 (M+H)+; $^1$H NMR (DMSO-d6) δ13.0 (s, 1H), 9.67 (s, 1H), 8.3 (d, 2H), 8.1 (m, 3H), 7.62 (d, 1H), 7.55 (d, 1H), 7.4 (d, 1H), 6.94 (d, 2H), 3.78 (s, 3H).
35) Purified by silica gel column chromatography (gradient, EtOAc in hexanes from 20% to 70%) (2.8 g, 70% yield); LCMS m/z 344 (M+H)+; Rf=0.24 (EtOAc/hexanes, 1/1); $^1$H NMR (300 MHz, CD$_3$OD) δ 8.35 (d, 2H), 8.15 (s, 1H), 8.05 (s, 1H), 7.95 (d, 1H), 7.7 (d, 1H), 7.55 (d, 1H), 7.46 (s, 4H).
36) Purified by silica gel column chromatography (gradient, EtOAc in hexanes from 10% to 70%); Rf=0.19 (EtOAc/hexanes, 3/2); (55 mg, 15% yield); LCMS m/z 429 (M+H)+; $^1$H NMR (DMSO-d6) δ 13.07 (s, 1H), 9.65 (s, 1H), 8.24 (d, 2H), 8.1 (m, 2H), 7.66 (d, 1H), 7.56 (d, 1H), 7.4 (d, 1H), 3.73 (s, 4H), 3.21 (4H).
37) Purified by silica gel column chromatography (gradient, EtOAc in hexanes from 10% to 50%); Rf=0.3 (EtOAc/hexanes, 1/1); (194 mg, 70% yield); LCMS m/z 420 (M+H)+; $^1$H NMR (DMSO-d6) δ 13.1 (s, 1H), 9.8 (s, 1H), 8.44 (d, 2H), 8.15 (m, 3H), 7.8 (m, 5H), 7.6 (d, 1H), 7.47 (m, 3H), 7.36 (m, 1H).
38) Crude 7e was purified by filtration and washed with methanol; Rf=0.16 (MeOH/CH$_2$Cl$_2$, 5/95); (0.36 g, 61% yield); LCMS m/z 401 (M+H)+; $^1$H NMR (DMSO-d6) δ 13.09 (s, 1H), 9.97 (s, 1H), 9.17 (s, 1H), 8.42 (d, 1H), 8.3 (s, 1H), 8.18 (m, 2H), 8.14 (s, 1H), 8.06 (d, 1H), 7.73 (d, 1H), 7.62 (d, 1H), 7.49 (d, 1H).
39) N-BOC protected boronic acid used in step 3; BOC group was removed by TFA in CH$_2$CL$_2$ at rt. Purified by silica gel column chromatography (gradient, EtOAc in hexanes from 10% to 75%); (45 mg, 19% yield); LCMS m/z 528 (M+M)+).
40) The residue was purified by column chromatography (dry mount, gradient from 20% to 75% EtOAc/Hex) to afford product. HPLC/MS: (M+H)+ m/z 428.2. Retention time (HPLC/MS, CH$_3$CN/H$_2$O/0.1% TFA). Rt=3.27.
41) The residue was purified by column chromatography (dry mount, gradient from 20% to 75% EtOAc/Hex) to afford product. HPLC/MS: (M+H)+ m/z 380.1. Retention time (HPLC/MS, CH$_3$CN/H$_2$O/0.1% TFA): (t=3.26
42) The residue was purified by column chromatography (dry mount, gradient from 20% to 75% EtOAc/Hex) to afford product. HPLC/MS: (M+H)+ m/z 388.2. Retention time (HPLC/MS, CH$_3$CN/H$_2$O/0.1% TFA): Rt=2.52.
43) The residue was purified by column chromatography (dry mount, gradient from 20% to 75% EtOAc/Hex) to afford product. HPLC/MS: (M+H)+ m/z 362.1. Retention time (HPLC/MS, CH$_3$CN/H$_2$O/0.1% TFA): Rt=2.69.
44) The residue was purified by column chromatography (dry mount, gradient from 20% to 75% EtOAc/Hex) to afford product. HPLC/MS: (M+H)+ m/z 374.1. Retention time (HPLC/MS, CH$_3$CN/H$_2$O/0.1% TFA): Rt=2.43.
45) The residue was purified by column chromatography (dry mount, gradient from 20% to 75% EtOAc/Hex) to afford product. HPLC/MS: (M+H)+ m/z 358.2. Retention time (HPLC/MS, CH$_3$CN/H$_2$O/0.1% TFA): Rt=2.46.
46) The residue was purified by column chromatography (dry mount, gradient from 20% to 75% EtOAc/Hex) to afford product. HPLC/MS: (M+H)+ m/z 358.2. Retention time (HPLC/MS, CH$_3$CN/H$_2$O/0.1% TFA): Rt=2.50.
47) The residue was purified by column chromatography (dry mount, gradient from 20% to 75% EtOAc/Hex) to afford product. HPLC/MS: (M+H)+ m/z 372.2. Retention time (HPLC/MS, CH$_3$CN/H$_2$O/0.1% TFA): Rt=2.61.
48) The residue was purified by column chromatography (dry mount, gradient from 20% to 75% EtOAc/Hex) to afford product. HPLC/MS: (M+H)+ m/z 370.2. Retention time (HPLC/MS, CH$_3$CN/H$_2$O/0.1% TFA): Rt=2.67.
49) The residue was purified by column chromatography (dry mount, gradient from 20% to 75% EtOAc/Hex) to afford product. HPLC/MS: (M+H)+ m/z 400.2. Retention time (HPLC/MS, CH$_3$CN/H$_2$O/0.1% TFA): Rt=2.81.
50) The residue was purified by column chromatography (dry mount, gradient from 20% to 75% EtOAc/Hex) to afford product. HPLC/MS: (M+H)+ m/z 386.2. Retention time (HPLC/MS, CH$_3$CN/H$_2$O/0.1% TFA): Rt=2.73.
51) The residue was purified by column chromatography (dry mount, gradient from 20% to 75% EtOAc/Hex) to afford product. HPLC/MS: (M+H)+ m/z 386.2. Retention time (HPLC/MS, CH$_3$CN/H$_2$O/0.1% TFA): Rt=2.79.
52) The residue was purified by column chromatography (dry mount, gradient from 20% to 75% EtOAc/Hex) to afford product. HPLC/MS: (M+H)+ m/z 374.2. Retention time (HPLC/MS, CH$_3$CN/H$_2$O/0.1% TFA): Rt=2.06.
53) The residue was purified by column chromatography (dry mount, gradient from 20% to 75% EtOAc/Hex) to afford product, HPLC/MS: (M+H)+ m/z 374.3. Retention time (HPLC/MS, CH$_3$CN/H$_2$O/0.1% TFA): Rt=2.17.
54) The residue was purified by column chromatography (dry mount, gradient from 20% to 75% EtOAc/Hex) to afford product. HPLC/MS: (M+H)+ m/z 412.1. Retention time (HPLC/MS, CH$_3$CN/H$_2$O/0.1% TFA): Rt=3.28. HPLC/MS: (M+H)+ 412.1 m/z. $^1$H NMR (DMSO-d6): 13.12(s, 1H, NH); 9.95 (s, 1H, NH); 8.71(s, 1H); 8.66(d, 1H); 8.21(d, 1H); 8.16(s,1H); 8.07 (s,1H); 7.85(s, 1H); 7.74(t, 1H); 7.65(d, 1H); 7.60(s, 1H); 7.55(d, 1H).
55) The residue was purified by column chromatography (gradient from 35-50% EtOAc/Hexane) to afford the pure product. HPLC/MS: (M+H)+ 427. Rf=0.64 (EtOAc/Hexanes, 80/20). $^1$H-NMR (300 MHz, CD$_3$OD) δ=8.23 (d, 2H), 8.16-8.14 (m, 1H), 8.08 (s, 1H), 7.95 (d, 1H), 7.73 (dd, 1H), 7.61 (d, 1H), 7.40 (d, 1H), 7.01 (d, 2H), 3.32-3.23 (m, 4H), 1.72-1.60 (m, 6H).
56) HPLC/MS: (M+H)+ m/z 426.4, Retention time (HPLC): Rt=2.55, Rf=0.68 in (EtOAc/Hex, 80/20). $^1$H-NMR (300 MHz, DMSO d6) δ 8.17-7.43 (m, 13H).
57) HPLC/MS: (M+H)+ m/z 421.4, Rf=0.46 in (MeOH/EtOAc, 07/93). $^1$H-NMR (300 MHz, CD$_3$OD) δ=7.5-6.25 (m, 14H).

Example 59

Preparation of 4-(N-5-aminoindazole)-2-(4-phenol)-thieno[3,2-d]pyrimidine

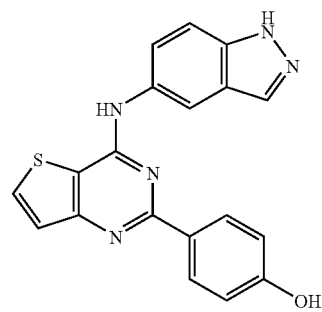

To a slurry of (N-5-aminoindazole)-2-(4-methoxyphenyl)thieno[3,2-d]-pyrimidine (Example 35, 0.86 g, 2.3 mmol) in anhyd $CH_2Cl_2$ was added $BBr_3$ at −78° C. The mixture was stirred overnight and warmed to room temperature. The reaction was cooled to 78° C. and treated with aqueous $NH_4Cl$ slowly to form precipitate. The solvent was concentrated by rotary evaporation and co-evaporated with toluene. The residue was treated with mixed solvent of MeOH and $CH_2Cl_2$, and then filtered. The filtrate was added to 6 g of silica gel and the solvent was removed by rotary evaporation. The residue was poured onto a silica gel column and eluted with a gradient mobile phase containing EtOAc and hexane to afford the product (0.42 g, 1.17 mmol, 51% yield). LC/MS m/z 360 (M+H)+, 1H NMR (DMSO-$d_6$): δ 13.15 (s, 1H), 9.8 (s, 1H), 9.7 (s, 1H), 8.2 (d, 2H), 8.1 (d, 3H), 7.7 (dd, 1H), 7.6 (dd, 1H), 7.4 (d, 1H), 6.8 (d, 2H); mp 297-299° C.

Example 60

Preparation of N-(1H-indazol-5-yl)-2-{4-[2-(4-morpholinyl)ethoxy]-phenyl}thieno[3,2-d]pyrimidin-4-amine

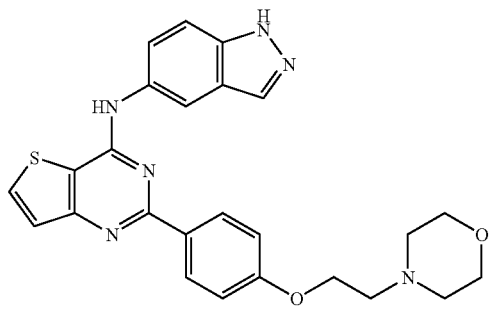

To a mixture of (Example 56, 62 mg, 0.17 g), $CsCO_3$ (100 mg, 0.3 mmol) in acetone (3 mL) was added N-(2-bromoethylene)-morpholine (34 mg in 1 mL of acetone). The solution was stirred at room temperature for 4 h and was filtered. The filtrate was added to 0.4 g of silica gel and the solvent was removed by rotary evaporation. The residue was poured onto a silica gel column and eluted with a gradient of EtOAc in hexane (from 50% to 100%) to afford a white precipitate (30 mg, 37% yield). Rf=0.18 (MeOH/$CH_2Cl_2$, 5/95). HPLC/MS: m/z 473 (M+H)+; 1H NMR (DMSO-$d_6$): δ13.07 (s, 1H), 9.71 (s, 1H), 8.30 (d, 2H), 8.09 (m, 3H), 7.70 (d, 1H), 7.57 (d, 1H), 7.43 (d, 1H), 7.02 (d, 2H), 4.14 (t, 2H), 3.57 (t, 4H), 2.68 (t, 2H), 2.46 (t, 4H).

Example 61

Preparation of N-(1H-indazol-5-yl)-N-(5-{4-[(2-pyridinylamino)methyl]phenyl}-1-benzothien-7-yl)amine

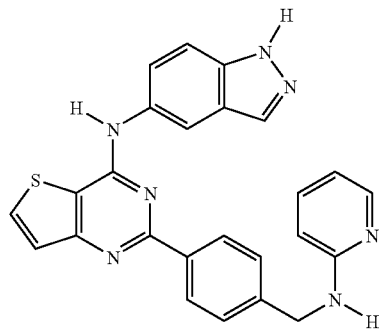

Step 1: Preparation of 4-[(2-pyridinylamino)methyl]phenylboronic acid

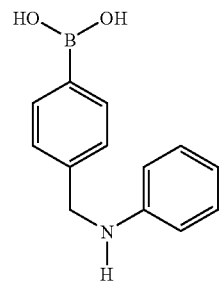

A mixture of 4-formylphenylboronic acid (1 g, 6.67 mmol) and 2-pyridinylamine (2.51 g, 26.7 mmol) in dichloroethane (25 mL) was stirred under argon at room temperature. To this mixture was added $NaB(OAc)_3$ (1.84 g, 8.67 mmol). The reaction mixture was quenched with $H_2O$ after 3 h. The solvent was removed under reduced pressure and the residue was dissolved in EtOAc and washed with water. The organic layer was then dried and concentrated in vacuo. The crude product was then purified by column chromatography (gradient from 20% to 80% EtOAc/hexane) to give product as colorless liquid (0.39 g, 30%). HPLC/MS: (M+H)+ 229.1 m/z. Retention time (LC-MS)=4.54 min. 1H NMR ($CD_3OD$): 7.90 (1H, d); 7.59 (2H, s); 7.43 (1H, m); 7.30(2H, d); 6.55 (2H, m); 4.47 (2H Step 2: Preparation of N-(1H-indazol-5-yl)-N-(5-{4-[(2-pyridinylamino)methyl]-phenyl}-1-benzothien-7-yl)amine

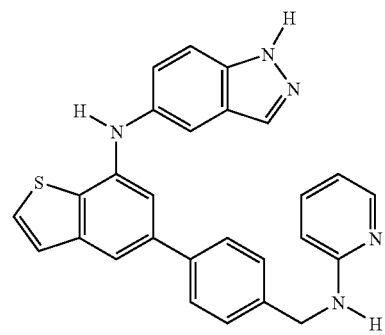

To a mixture of N-(2-chlorothieno[3,2-d]pyrimidin-4-yl)-N-(1H-indazol-5-yl)amine (50 mg, 0.16 mmol), $Na_2CO_{3(aq)}$ (2 M, 1.0 mL) in butanol/toluene (1:1, 4 mL) a stream of argon was bubbled through for 15 min. To the mixture was added 4-[(2-pyridinylamino)methyl]phenylboronic acid (0.15 g, 0.66 mmol) and tetrakis(triphenylphosphine)palladium(0) (0.06 g, 0.08 mmol) in a single portion. The resulting reaction mixture was heated to reflux for 24 h. On cooling, the solution was concentrated, taken up in EtOAc and washed with water. The organic layers were dried over anhyd sodium sulfate and concentrated in vacuo. The crude product was purified by silica gel column chromatography (gradient from 20% to 80% EtOAc/hexane) to give the product (25 mg). HPLC/MS: (M+H)+ 450.1 m/z. Retention time (LC-MS)= min. 1H NMR ($CD_3OD$): 8.31 (2H, d); 8.11 (1H, s); 8.05 (1H, s); 7.96(1H, d); 7.91 (1H, d); 7.71(1H, d); 7.58 (1H, d); 7.47(4H, m); 6.61(2H, m); 4.55 (2H, s).

Example 62

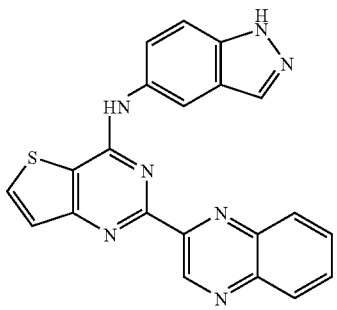

Step 2: Preparation of methyl 3-[(2-quinoxalinylcarbonyl)amino]-2-thiophenecarboxylate

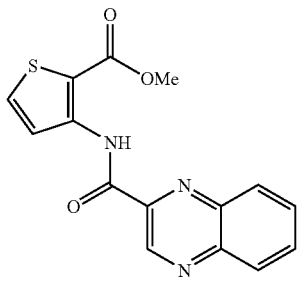

To a solution of methyl 3-amino-2-thiophenecarboxylate (0.82 g, 5.2 mmol) and 2-quinoxalinecarbonyl chloride at 0° C. was added pyridine (1 mL) dropwise. The resulting solution was stirred at room temperature overnight. The solvent was removed under reduced pressure and the residue was dissolved in EtOAc, washed with saturated $NH_4Cl$, and $NaHCO_3$. The organic layer was the dried and concentrated in vacuo. The crude product was used directly in the next step without further purification.

Step 2: Preparation of 3-[(2-quinoxalinylcarbonyl)amino]-2-thiophenecarboxylic acid

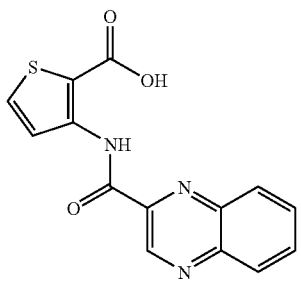

Methyl 3-[(2-quinoxalinylcarbonyl)amino]-2-thiophenecarboxylate (0.5 g, 1.6 mmol) was dissolved in $CH_2Cl_2$ (100 mL) at 0° C. and $BBr_3$ (4.8 mL, 1M solution in $CH_2Cl_2$) was added dropwise. The solution was stirred at room temperature overnight. The reaction was quenched with $NH_4Cl$ at 0° C. The organic layer washed with $NaHCO_3$ and separated. The resulting organic layer was treated slowly with dil HCl until the solution became acidic. The mixture was concentrated and redissolved in EtOAc. This solution washed with water, The solvent was removed under reduced pressure and the crude product was re-crystallized from methanol to give the desired product (0.2 g, 42%). HPLC/MS: $(M+H)^+$ 300.1 m/z. Retention time (LC-MS)=2.65 min. $^1H$ NMR (DMSO-D6): 13.75 (s, 1H, broad); 12.43(s, 1H); 9.61(s, 1H); 8.26(m, 2H); 8.17(m, 1H); 8.07(m, 2H); 7.99(d, 1H).

Step 3: Preparation of N-[2-(aminocarbonyl)-3-thienyl]-2-quinoxalinecarboxamide

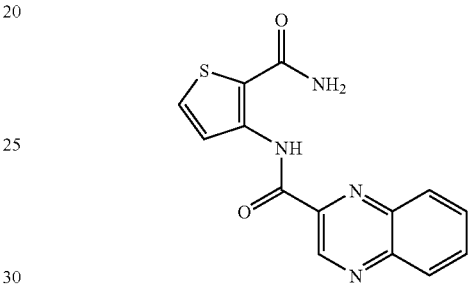

A mixture of 3-[(2-quinoxalinylcarbonyl)amino]-2-thiophenecarboxylic acid (0.70 g, 2.3 mmol), 1-[3-(dimethylamino)propyl]-3-ethylcarbodiimide hydrochloride (EDC, 2.24 g, 11.5 mmol), and 4-(dimethylamino)pyridine (DMAP, 1.43 g, 11.5 mmol) in $CH_2Cl_2$ (100 mL) was stirred at room temperature for 2 h. To the reaction mixture was added aqueous ammonia (40%, 5 mL), and the stirring continued for another 12 h. The solvent was evaporated to dryness and the resulting solid was washed with satd $NH_4Cl$ solution (3×), $NaHCO_3$ solution and $H_2O$. The organic phase was evaporated to dryness resulting in a white powder (0.32 g, 46%). HPLC/MS: $(M+H)^+$ 299.4 m/z Retention time (LC-MS)=2.74 min.

Step 4: Preparation of 2-(2-guinoxalinyl)thieno[3,2-d]pyrimidin-4-ol

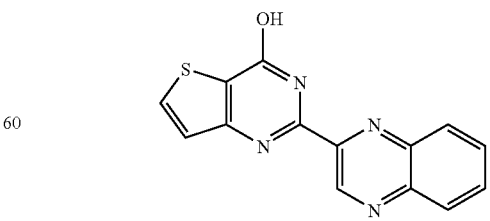

To a solution of N-[2-(aminocarbonyl)-3-thienyl]-2-quinoxalinecarboxamide (0.24 g, 0.8 mmol) in ethanol (15 mL)

was added aqueous NaOH (1.0 M, 2.4 mL). The resulting mixture was stirred at reflux temperature overnight. The mixture cooled to rt and the solvent was removed under reduced pressure. The residue was dissolved in water and acidified with HCl. The white precipitate was filtered and washed thoroughly with water to give product as yellow powder (0.17 g, 77%). HPLC/MS (M+H)+ 281.1 m/z Retention time (LC-MS)=2.78 min. ¹H NMR (DMSO-D6) 12.65 (s, 1H, broad); 9.77(s, 1H); 8.32(d, 1H); 8.28(m, 1H); 8.23(m, 1H); 8.01(m, 2H); 7.63 (d, 1H).

Step 5: Preparation of 2-(4-chlorothieno[3,2-d]pyrimidin-2-yl)quinoxaline

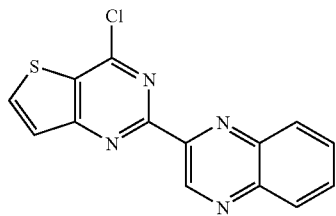

A solution of 2-(2-quinoxalinyl)thieno[3,2-d]pyrimidin-4-ol (150 mg, 0.54 mmol) in POCl₃ (5 mL) was heated to reflux and maintained at reflux overnight. After cooling to rt, excess POCl₃ was removed under reduced pressure to give the crude product which was used in the next step without further purification.

Step 6: Preparation of N-(1H-indazol-5-yl)-2-(2-guinoxalinyl)thieno[3,2-d]-pyrimidin-4-amine

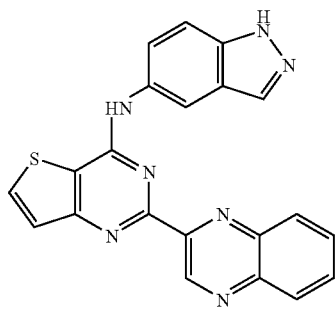

Bg9 procedure similar to Example 1, step 2, 2-(4-chlorothieno[3,2-d]pyrimidin-2-yl)quinoxaline and 5-aminoindoazole were allowed to react in THF. After the removal of the solvent, the crude product was purified through column (gradient from 20% to 80% EtOAc/hexane) to afford the product. HPLC/MS: (M+H)+ 396.1 m/z. Retention time (LC-MS)= 2.42 min.

Utilizing the method described above for Example 62 and using the appropriate starting materials, the examples shown below in Table 2 were prepared.

TABLE 2

| Ex. No. | Structure | RT (min) (LC-MS) | MS [M + H]+ |
|---|---|---|---|
| 63 | 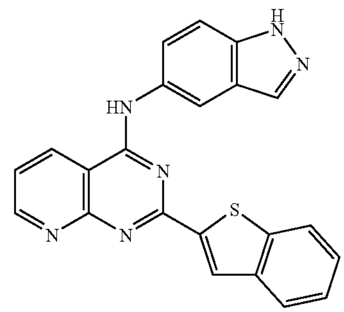 | 2.76 | 395 |
| 64 | 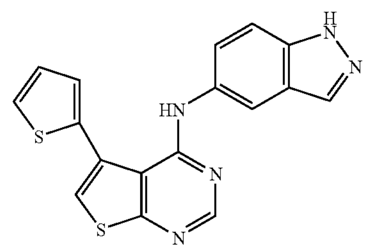 | 3.42 | 350 |
| 65 | 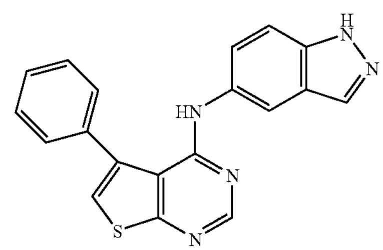 | 3.42 | 344 |

Example 66

Preparation of N-(1H-indazol-5-yl)-2-(3-methoxyphenyl)-5-methylfuro[2,3-d]-pyrimidin-4-amine

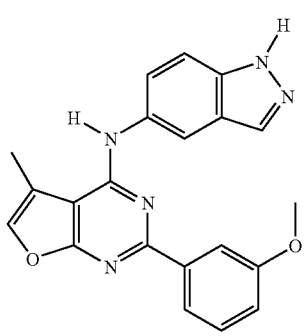

Step 1: Preparation of 2-amino-4-methyl-3-furonitrile

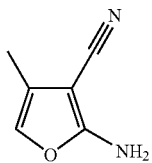

To a mixture of malononitrile (0.96 g, 14.6 mmol), acetol (1.08 g, 14.6 mmol) in methanol (10 mL) at 0° C. was added, dropwise, triethylamine (2.0 mL). The reaction mixture was stirred at room temperature overnight. After removal of solvent under reduced pressure the crude solid washed with cold isopropanol to give product as white powder (0.54 g, 30%). HPLC/MS: (M+H)$^+$ 123.3 m/z. Retention time (LC-MS)= 1.81 min. $^1$H NMR (CD$_3$OD): 6.58(s, 1H,); 1.95 (s, 3H).

Step 2: Preparation of 4-chloro-2-(3-methoxyphenyl)-5-methylfuro[2,3-d]-pyrimidine

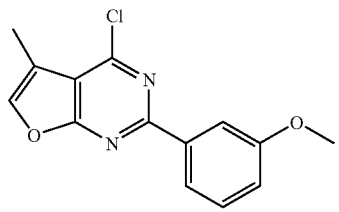

The Vilsmeier Reagent was prepared by stirring of 3-methoxy-N,N-dimethylbenzamide (1.17 g, 7.9 mmol) and POCl$_3$ (3.0 g, 19.7 mmol) at 0° C. for 30 minutes. To this reagent was added 2-amino-4-methyl-3-furonitrile (1.0 g, 6.6 mmol) and dry dichloroethane (5.0 ml). The reaction mixture was heated to 40° C. and stirred at this temperature for 18 h. The mixture was then poured into ice water. After adjusting the pH of the solution to 9 via treatment with NaHCO$_3$ solution, the solution was extracted with dichloromethane. The organic layer was then dried and concentrated. The crude product was purified by silica gel column chromatography (10/90, ethyl acetate/hexane). HPLC/MS: (M+H)$^+$ 275.1 m/z. Retention time (LC-MS)=3.99 min. $^1$H NMR (DMSO-D6): 8.10 (s, 1H,); 7.98(d, 1H); 7.86 (m, 1H); 7.49 (t, 1H); 7.15 (m, 1H); 3.85 (s, 3H).

Step 3: Preparation of N-(1H-indazol-5-yl)-2-(3-methoxyphenyl-5-methylfuro[2,3-d]pyrimidin-4-amine

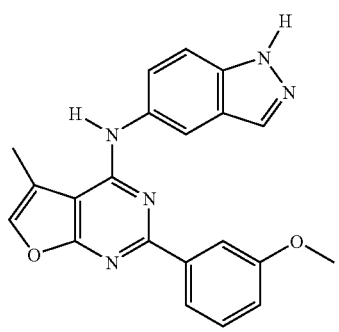

A mixture of 4-chloro-2-(3-methoxyphenyl)-5-methylfuro[2,3-d]pyrimidine and 5-Aminoindazole in butanol (2.0 ml) was heated to 100° C. overnight. After the removal of the solvent, the crude product was purified through column (gradient from 20% to 80% ethyl acetate/hexane) to give product Bay 59-8843 (15.2 mg). HPLC/MS: (M+H)$^+$ 372.4 m/z. Retention time (LC-MS)=2.53 min. $^1$H NMR (DMSO-D6): 13.10(s, 1H, NH); 8.70(s, 1H, NH); 8.11(s, 2H); 7.90(m, 2H); 7.75(m, 2H); 7.63(d, 1H); 7.41(t, 1H); 7.05(m, 1H); 3.80 (s, 3H).

Utilizing a similar procedure to that described above and substituting the appropriate 4-chloro-2-substituted phenyl 5-methylfluoro[2.3 mL]pyrimidine, the following compounds were prepared.

TABLE 3

| Example No | R1 | R2 | RT (min) (from LC-MS) | Mass Spec [electrospray] |
|---|---|---|---|---|
| 67 | 5-Me | H | 3.31 | MH+ 342.1 |
| 68 | 5-Me | 4-OMe | 3.42 | MH+ 372.2 |
| 69 | 5,6-Di-Me | H | 3.65 | MH+ 356.3 |
| 70 | 5,6-Di-Me | 3-OCH3 | 3.49 | MH+ 386.1 |

LC-MS system: Acetonitrile/Water/0.1% TFA
LC-MS Detector: UV and ELSD

Example 71

Preparation of 3-[4-(1H-indazol-5-ylamino)-5-methylfuro[2,3-d]pyrimidin-2-yl]phenol

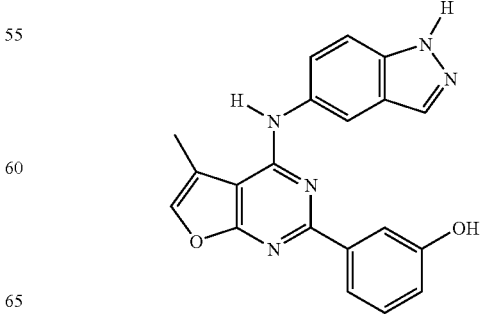

To a solution of N-(1H-indazol-5-yl)-2-(3-methoxyphenyl)-5-methylfuro[2,3-d]pyrimidin-4-amine (50.0 mg, 0.13 mmol) in CH$_2$Cl$_2$ (20 ml) cooled to −78° C. was added BBr$_3$ (0.7 mL, 2.83 mmol, 1M solution in CH$_2$Cl$_2$) drop-wise. The mixture warmed to rt and was stirred overnight. The reaction was quenched with water and the organic and aqueous phases were separated. The organic layer was dried and concentrated under reduced pressure. The crude product was purified by silica gel column chromatography (gradient from 20% to 80% EtOAc/hexane) to afford are product (8.4 mg, 17.5%). HPLC/MS: (M+H)$^+$ 358.1 m/z. Retention time (LC-MS)= 3.01 min. $^1$H NMR (DMSO-D6): 8.54(s, NH); 8.11 (d, 1H); 8.07(s, 1H); 7.75(m, 3H); 7.60(d, 1H); 7.47(d, 1H); 7.20(t, 1H); 6.83(m, 1H).

Example 72

Preparation of N-{3-[4-(1H-indazol-5-ylamino)thieno[3,2-d]pyrimidin-2-yl}isonicotinamide

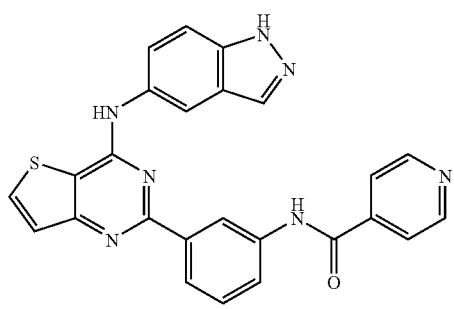

Step 1: Preparation of 2-(3-aminophenyl)-N-(1H-indazol-5-yl)thieno[3,2-d]-pyrimidin-4-amine 2-Chloro-N-(1H-indazol-5-yl)thieno[3,2-d]pyrimidin-4-amine (10 mmol, 1 equivalent) was suspended in dimethyl ethylene glycol (60 mL) and Na$_2$CO$_3$ solution (2M, 10 mL) and flushed with argon for 20 min. To this suspension 3-aminophenyl boronic acid (25 mmol, 2.5 eq) and Pd(PPh$_3$)$_4$ (2.5 mmol, 0.25 eq) were added. The reaction mixture was refluxed under AR at 100° C. for 48 h. The solvent was evaporated off in vacuo. The residue was taken into THF (100 mL) plus EtOAc/water. (100 mL, 1:1). The organic layer was evaporated to dryness. The residue was separated by silica gel column chromatography (0–5% MeOH in CH$_2$Cl$_2$). The product was obtained as yellow powder (2.04 g, 57%). (M+H)$^+$=359, RT (LC-MS)=1.93.

Step 2: Preparation of 2-(3-aminophenyl)-N-(1H-indazol-5-yl)thieno[3,2-d]-pyrimidin-4-amine

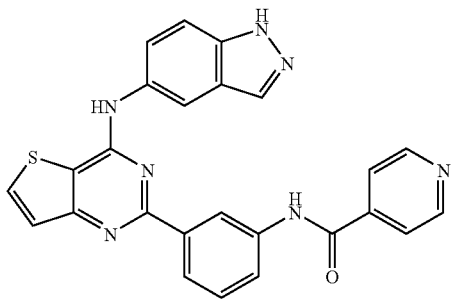

To a cold solution of the product of step 1 (3.35 mmol, 1 eq) in dry pyridine (50 mL) was added isonicotonic anhydride (6.7 mmol, 2 eq) in two portions. A precipitate formed shortly after the addition. The reaction mixture was stirred at room temperature for 4 h and poured into ice and was stirred continued. The solid was collected by filtration and washed with water. This crude product was further purified by silica gel column chromatography (0–4% MeOH/CH$_2$Cl$_2$) to afford a pale yellow solid (0.8 g, 50%). (M+H)$^+$=464, RT (LC-MS)=2.12.

Example 73

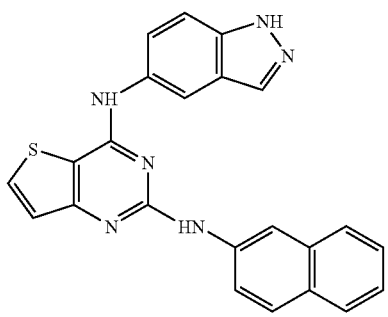

Preparation of N-(1H-indazol-5-yl)-N-[2-(2-napthylamino)thieno[3,2-d]pyrimidin-4-yl]amine To a solution of 2-chloro-N-(1-H-indazol-5-yl)thieno[3,2-d]pyrimidin-4-amine (0.166 mmol) in n-BuOH (1.5 mL) was added 2-aminonaphthylene (0.5 mmol, 3 equivalent) and was stirred at 100° C. for two days. The resulted solid was collected on funnel, washed with isopropanol and ether to give a pale gray crystalline product (74%). (M+H)$^+$=409, RT (LC-MS)=2.56.

Utilizing this method and substituting the appropriate starting materials, the compounds shown in Table 5 were also prepared.

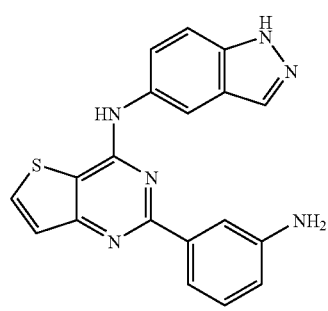

TABLE 5

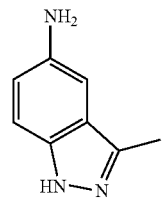

| Ex. No | Ar | LC-MS RT (min) | Mass Spec (source) |
|---|---|---|---|
| 73 | 3-aminophenyl | 1.93 | 359 |
| 74 | 3-isonicotinamido-phenyl | 2.12 | 464 |
| 75 | 5-(1H-indolyl)amino | 2.34 | 398 |
| 76 | 4-phenoxyanilino | 2.78 | 451 |

Example 77

Preparation of 2-(1,1'-biphenyl-3-yl)-N-(3-methyl-1H-indazol-5-yl)thieno[3,2-d]-pyrimidin-4-amine

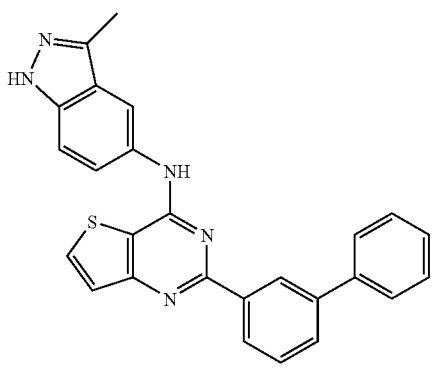

Step 1: Preparation of 3-methyl-5-nitro-1H-indazole

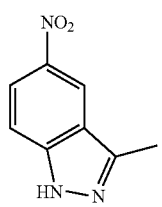

A solution of 2-fluoro-5-nitroacetophenone (1.57 g, 8.6 mmol) in ethylene glycol (50 mL) was added hydrazine (0.29 g, 9.0 mmol) was stirred for 2 h at room temperature and then heated at 165° C. for 24 h. The reaction mixture was cooled to room temperature, poured over EtOAc (100 mL), and extracted with H₂O (2×100 mL). The organic layers was dried over Na₂SO₄ and the solvent was removed in vacuo. The crude product was purified by silica gel chromatography to afford a light yellow solid (0.8 g, 53%) Rf=0.2 (EtOAc/hexane, 1/3). $^1$H NMR CDCl₃ δ 8.63 (s, 1H), 8.23 (d, 2H, J=3 Hz), 7.46 (d, 1H, J=3 Hz), 2.60 (s, 3H).

Step 2: Preparation of 3-methyl-1H-indazol-5-amine

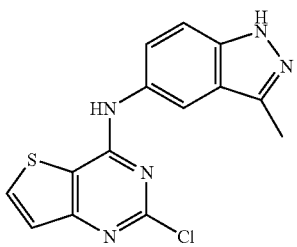

To a stirred solution of the compound prepared in step 1 (0.8 g, 4 mmol) in methanol was added Pd/C catalyst (0.1 g) The resulting reaction mixture was stirred under a hydrogen atmosphere (1 atm) at room temperature overnight. The mixture was filtered and the filtrate was concentrated in vacuo to afford crude product (0.7 g) as light yellow solid that was not further purified. Rf=0.50 (EtOAc/hexane, 1/1). $^1$H NMR CDCl₃ δ 7.20 (s, 1H), 6.90-6.80 (m, 2H), 2.41 (s, 3H).

Step 3: Preparation of 2-chloro-N-(3-methyl-1H-indazol-5-yl)thieno[3,2-d]-pyrimidin-4-amine

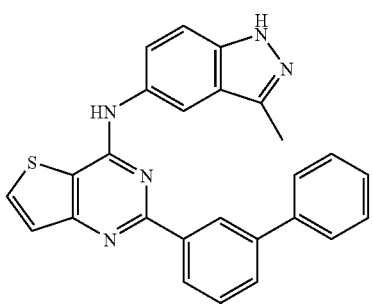

A mixture of the compound in step 2 (0.7 g, 4.8 mmol), Example 1, step 1, (0.98 g, 4.8 mmol) and potassium acetate (0.66 g, 6.7 mmol) in THF/H₂O (75 mL, 2/1) was stirred at room temperature for 16 h. The mixture was extracted with EtOAc, washed with brine, and dried over NaSO₄. The solvent was filtered and evaporated to dryness. The residue was purified by silica gel column chromatography to afford a yellow solid (1.2 g, 80% yield). Rf=0.3 (EtOAc/hexane, 1/1). $^1$H NMR (Methanol-d₄) δ 7.95-7.80 (m, 2H), 7.63-7.50 (m, 2H), 7.19 (d, 1H, J=3 Hz), 2.40 (s, 3H).

Step 4: Preparation of 2-(1,1'-biphenyl-3-yl)-N-(3-methyl-1H-indazol-5-yl)thieno[3,2-d]pyrimidin-4-amine A procedure analogous for that of Example 1, step 3 was followed. A mixture of the step 3 product (0.4 g, 1.3 mmol), 3-phenylphenylboronic acid, (0.3 g, 1.5 mmol) and sodium bicarbonate (0.33 g, 3.9 mmol) in DME/H$_2$O (3/1, 56 mL) was flushed with Ar for 1 h, and Pd(dppf)Cl$_2$ was added. The solution was heated to reflux for 48 h at 100° C. After removal of solvent in vacuo, the crude product was purified by silica gel chromatography to afford a white solid (0.35 g, 65%). Rf=0.2 (EtOAc/hexane, 1/1). $^1$H NMR (Methanol-d$_4$) δ 8.69 (s, 1H), 8.35 (d, 1H, J=3 Hz), 8.25 (s, 1H), 8.00 (d, 1H, J=3 Hz), 7.70-7.60 (m, 4H), 7.51-7.31 (m, 6H), 2.42 (s, 3H).

Example 78

Preparation of 2-(1-benzothien-2-yl)-N-(1H-indazol-5-yl)period[2,3-d]pyrimidin-4-amine

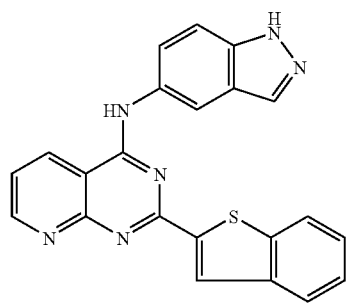

Step 1: preparation of 2-[(1-benzothien-2-ylcarbonyl)amino]nicotinic acid

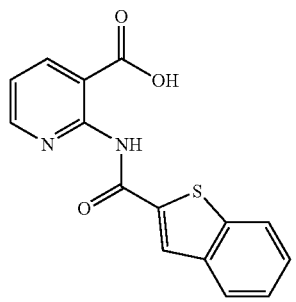

To a solution of 2-aminonicotinic acid (91.1 g, 8.0 mmol), triethylamine (2.7 mL, 19.1 mmol) and acetone/H$_2$O (3:1, 100 mL) was added 1-benzothiophene-2-carbonyl chloride (2.04 g, 10.4 mmol) at 0° C. The resulting solution was allowed to warm to rt and stir overnight. The volatile solvent was removed under reduced pressure and the aqueous solution was acidified with HCl (conc.). The resulting precipitate was filtered and then washed with EtOAc and dried under reduced pressure to afford the product. (1.2 g, 52%). NMR (DMSO): 11.7(1H, broad), 8.60(1H, m); 8.36(1H, s); 8.25 (1H, d); 8.07(1H, d); 8.02(1H, d); 7.51(2H, m); 7.36(1H, m).

Step 2: preparation of 2-[(1-benzothien-2-ylcarbonyl)amino]nicotinamide

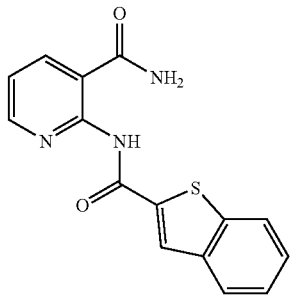

A mixture of 2-[(1-benzothien-2-ylcarbonyl)amino]nicotinic acid (112 g, 4.0 mmol), EDC (2.3 g, 12.0 mmol) and DMAP (1.46 g, 12.0 mmol) in anhyd dichloromethane (50 mL) was stirred at room temperature for 2 h. To this mixture was added 40% aqueous ammonia (4.0 mL), and the resulting solution stirred at room temperature overnight. The solvent was removed in vacuo and the resulting solid was washed with satd NH$_4$Cl solution, NaHCO$_3$ solution, and water. The solid was dried to give product as white powder (0.92 g, 77%). HPLC/MS: (M+H)$^+$298.15 m/z Retention time (LC-MS)= 2.44 min. $^1$H NMR (DMSO-D6): 12.25 (1H, s); 8.54(1H, m); 8.21(1H, s); 8.18(1H, d); 8.07(2H, m); 7.52(2H, m); 7.32(1H, m).

Step 3: Preparation of 2-(1-benzothien-2-yl)pyrido[2,3-d]pyrimidin-4-ol

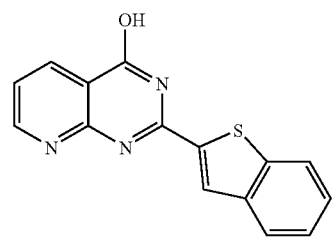

To a solution of 2-[(1-benzothien-2-ylcarbonyl)amino] nicotinamide (0.3 g, 1.0 mmol) in ethanol (20 mL) was added NaOH (10 N, 0.3 mL, 3.0 mmol). The resulting solution was heated to reflux overnight. On cooling to rt the solvent was removed under reduced pressure. The residue was dissolved in excess of water and acidified with HCl. The resulting precipitate was filtered and washed with water to afford the product as yellow powder (0.16 g, 57%). HPLC/MS: (M+H)$^+$ 280.0 m/z; Retention time (LC-MS)=2.66 min; $^1$H NMR (DMSO-D6): 13.17 (1H, s); 8.94(1H, m); 8.61(1H, s); 8.50 (1H, d); 8.08(1H, d); 7.97(1H, d); 7.52(3H, m).

Step 4: Preparation of 2-(1-benzothien-2-yl)-4-chloropyrido[2,3-d]pyrimidine

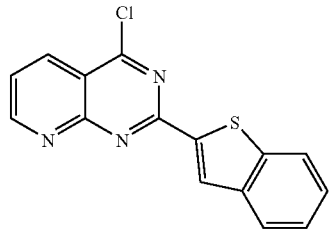

To a suspension of 2-(1-benzothien-2-yl)pyrido[2,3-d]pyrimidin-4-ol (150 mg, 0.54 mmol) in chloroform (10 mL) was added thionyl chloride (0.47 mL, 6.4 mmol) and a catalytic amount of DMF. The reaction was heated to reflux for 4 h and allowed to cool to rt. The solvent was removed under reduced pressure and the resultant product was (18.2 mg, 12%) used directly in the next step without further purification. HPLC/MS: $(M+H)^+$ 298.2 m/z; Retention time (LC-MS)=3.76 min; $^1$H NMR (DMSO)-D6): 9.24(1H, m); 8.73(1H, d); 8.55(1H, s); 8.10(2H, t); 7.86(1H, m); 7.50(2H, m).

Step 5: Preparation of N-[2-(1-benzothien-2-yl)pyrido[2,3-d]pyrimidin-4-yl]-N-(1H-indazol-5-yl)amine

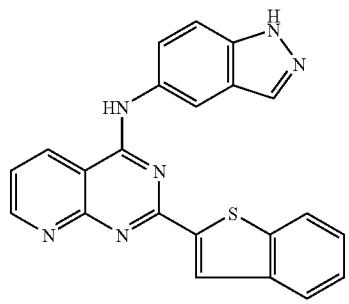

A mixture of 2-(1-benzothien-2-yl)-4-chloropyrido[2,3-d]pyrimidine (18.2 mg, 0.06 mmol), 5-aminoindazole (40 mg, 0.3 mmol) and potassium carbonate (83 mg, 0.6 mmol) in dioxane (20 mL) was heated to 100° C. and continued for 24 h. After removal of the solvent, the crude product was purified by silica gel column chromatography (gradient from 20% to 80% EtOAc/hexane) to give the product (1.0 mg, 4.0%); HPLC/MS: $(M+H)^+$ 395.2 m/z; Retention time (LC-MS)= 2.75 min.

The following compounds are prepared analogously:

| Example No. | Structure | MS (Exact Mass) | MW (calcd) |
|---|---|---|---|
| 79 | 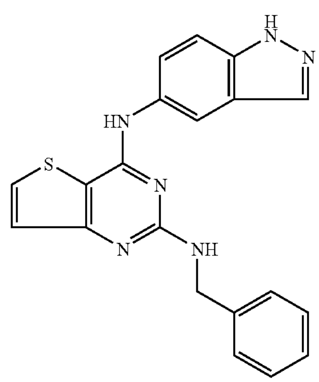 | 372.12 | 372.45 |
| 80 | 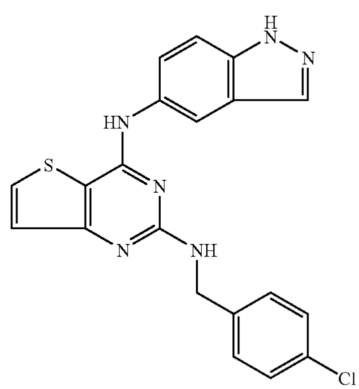 | 406.08 | 406.90 |

-continued

| Example No. | Structure | MS (Exact Mass) | MW (calcd) |
|---|---|---|---|
| 81 | 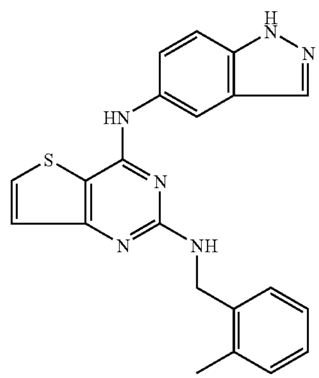 | 386.13 | 386.48 |
| 82 | 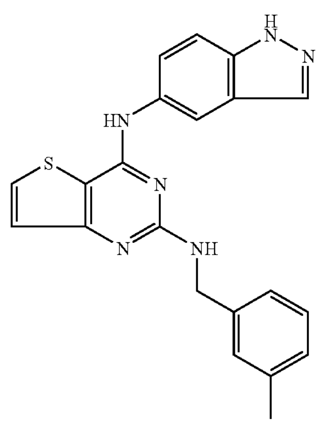 | 386.13 | 386.48 |
| 83 | 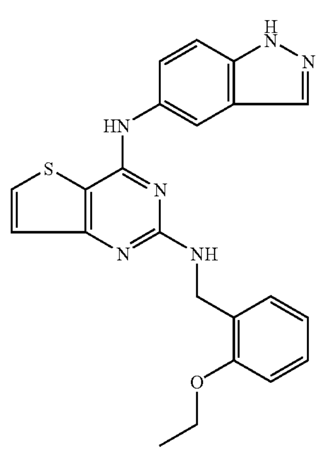 | 416.14 | 416.51 |

-continued

| Example No. | Structure | MS (Exact Mass) | MW (calcd) |
|---|---|---|---|
| 84 | 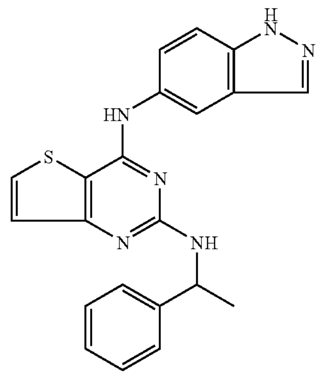 | 386.13 | 386.48 |
| 85 | 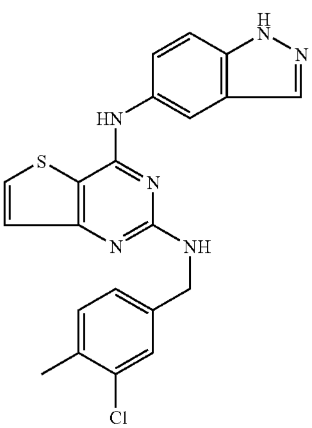 | 420.09 | 420.93 |
| 86 | 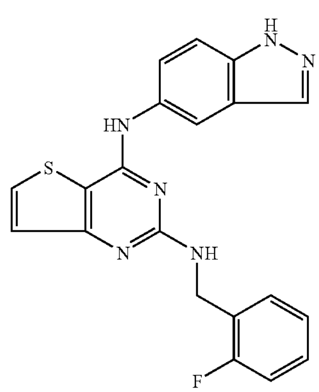 | 390.11 | 390.44 |

-continued

| Example No. | Structure | MS (Exact Mass) | MW (calcd) |
|---|---|---|---|
| 87 | 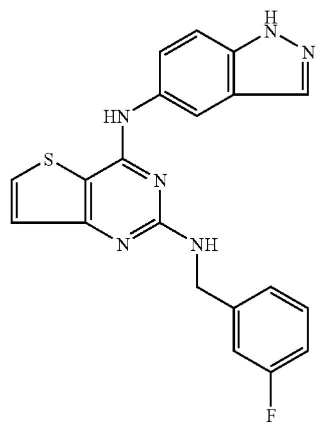 | 390.11 | 390.44 |
| 88 | 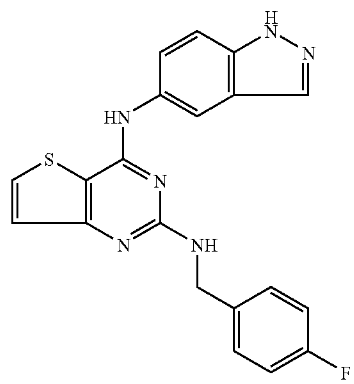 | 390.11 | 390.44 |
| 89 | 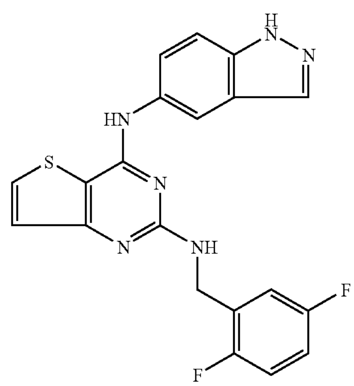 | 408.10 | 408.43 |
| 90 | 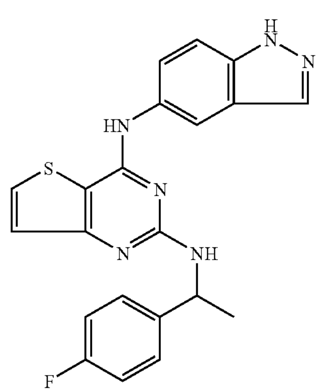 | 404.12 | 404.47 |

| Example No. | Structure | MS (Exact Mass) | MW (calcd) |
|---|---|---|---|
| 91 | 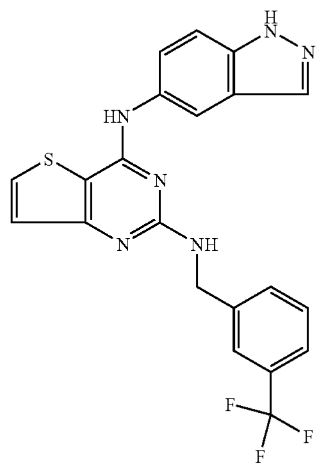 | 440.10 | 440.45 |
| 92 | 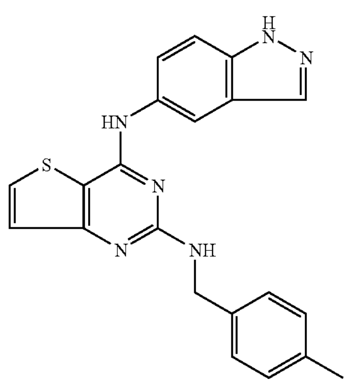 | 386.13 | 386.48 |
| 93 | 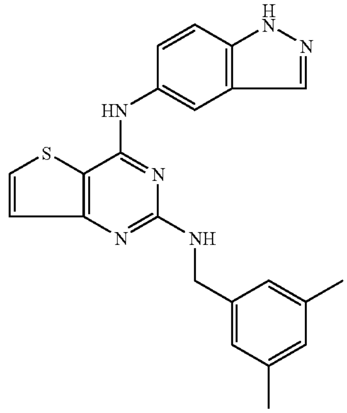 | 400.15 | 400.51 |

-continued

| Example No. | Structure | MS (Exact Mass) | MW (calcd) |
|---|---|---|---|
| 94 | 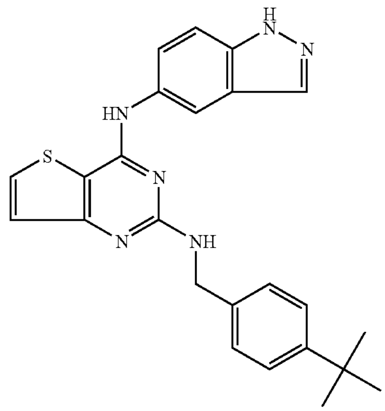 | 428.18 | 428.56 |
| 95 | 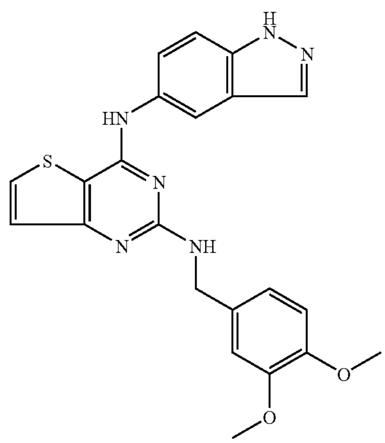 | 432.14 | 432.51 |
| 96 | 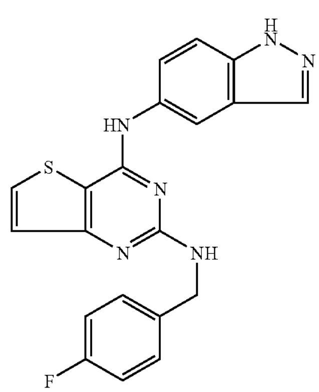 | 390.11 | 390.44 |

-continued

| Example No. | Structure | MS (Exact Mass) | MW (calcd) |
|---|---|---|---|
| 97 | 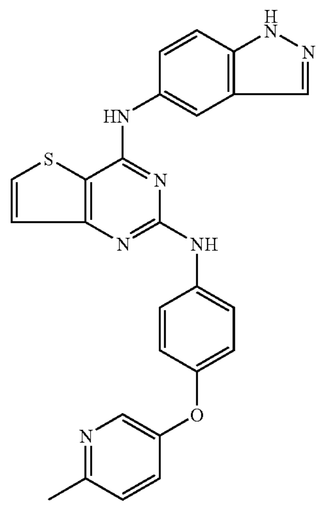 | 465.14 | 465.54 |
| 98 | 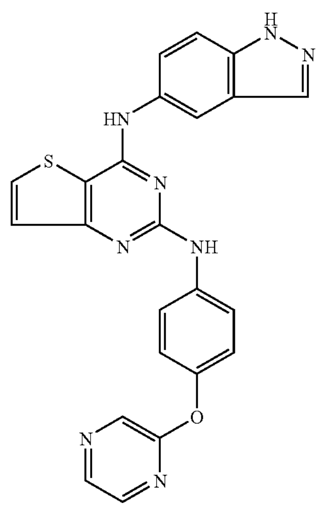 | 452.12 | 452.50 |
| 99 | 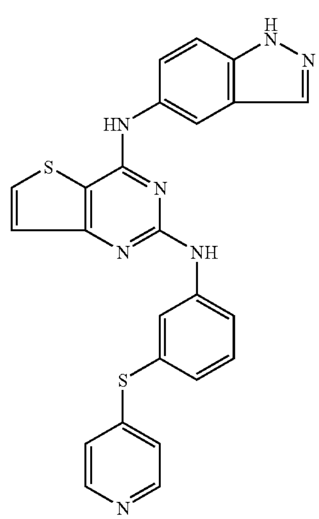 | 467.10 | 467.58 |

-continued
| Example No. | Structure | MS (Exact Mass) | MW (calcd) |
|---|---|---|---|
| 100 | 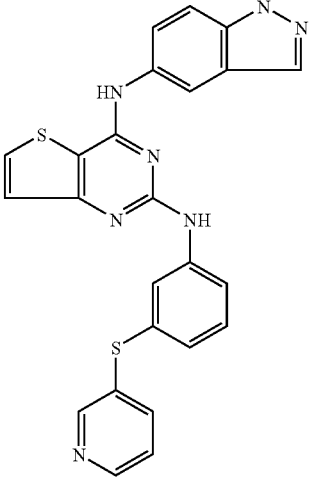 | 467.10 | 467.58 |
| 101 | 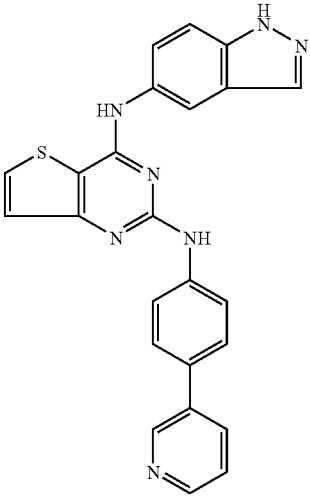 | 435.13 | 435.51 |
| 102 | 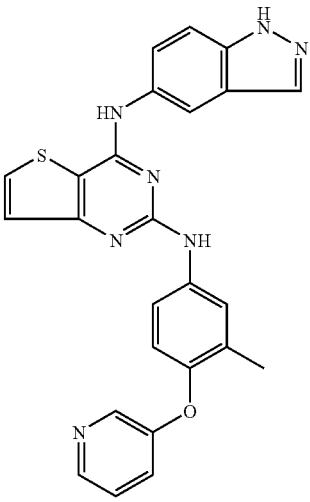 | 465.14 | 465.54 |

-continued
| Example No. | Structure | MS (Exact Mass) | MW (calcd) |
|---|---|---|---|
| 103 | 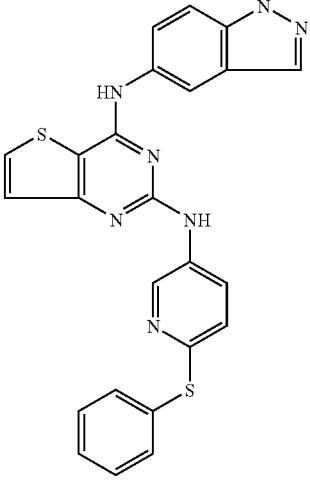 | 467.10 | 467.58 |
| 104 | 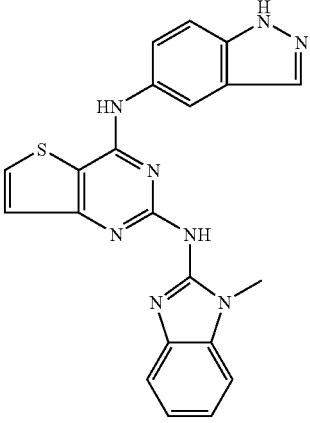 | 412.12 | 412.48 |
| 105 | 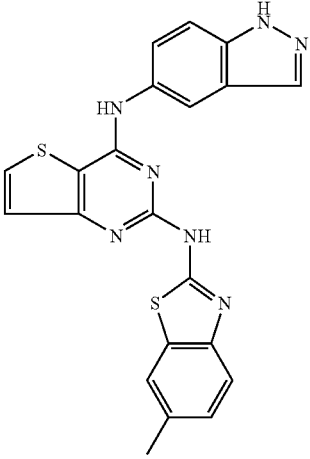 | 429.08 | 429.53 |

-continued

| Example No. | Structure | MS (Exact Mass) | MW (calcd) |
|---|---|---|---|
| 106 | 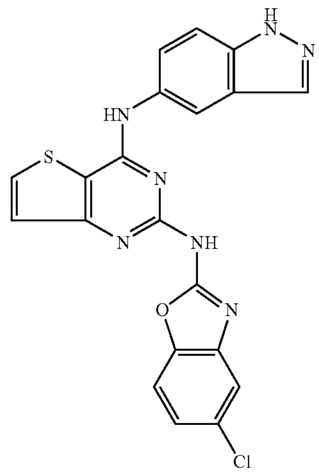 | 433.05 | 433.88 |
| 107 | 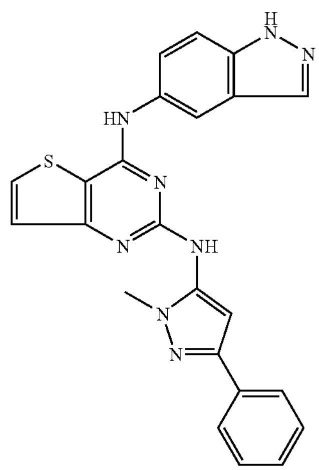 | 438.14 | 438.52 |
| 108 | 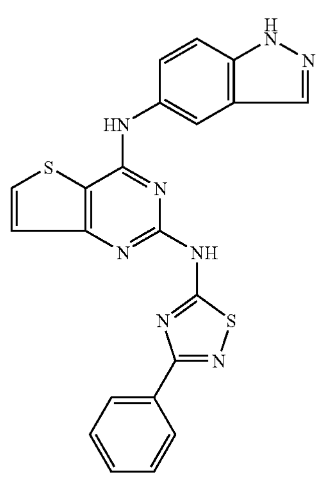 | 442.08 | 442.53 |

-continued

| Example No. | Structure | MS (Exact Mass) | MW (calcd) |
|---|---|---|---|
| 109 | 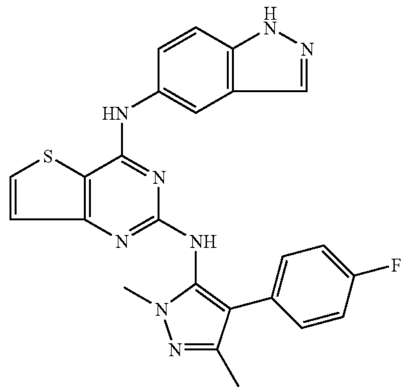 | 470.14 | 470.53 |
| 110 | 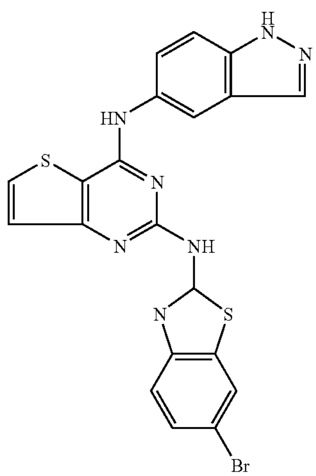 | 492.98 | 494.40 |
| 111 | 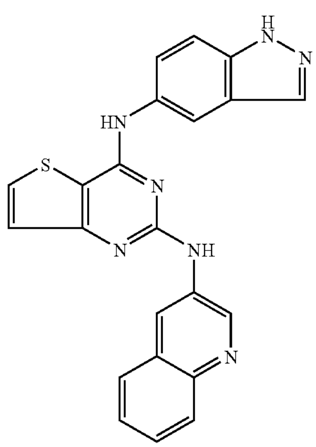 | 409.11 | 409.47 |

-continued

| Example No. | Structure | MS (Exact Mass) | MW (calcd) |
|---|---|---|---|
| 112 | 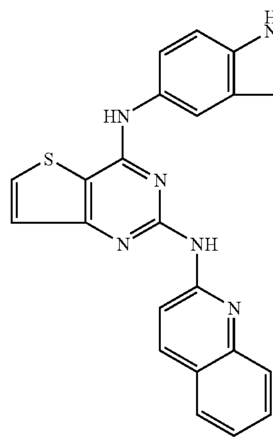 | 409.11 | 409.47 |
| 113 | 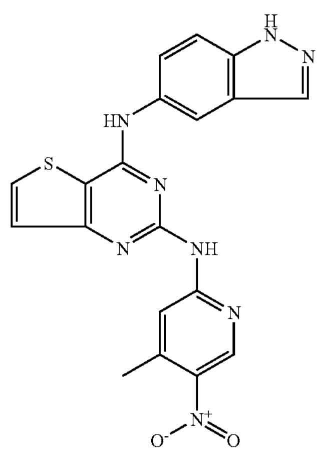 | 418.10 | 418.44 |
| 114 | 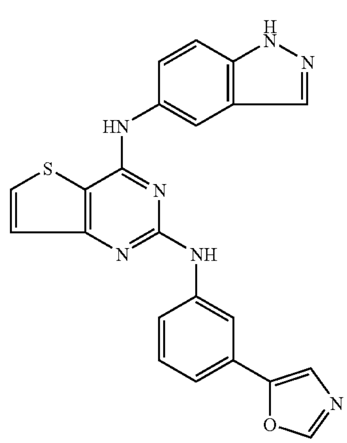 | 425.11 | 425.47 |

-continued

| Example No. | Structure | MS (Exact Mass) | MW (calcd) |
|---|---|---|---|
| 115 | 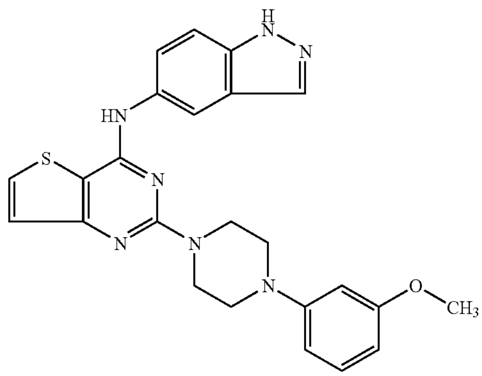 | 457.17 | 457.56 |
| 116 | 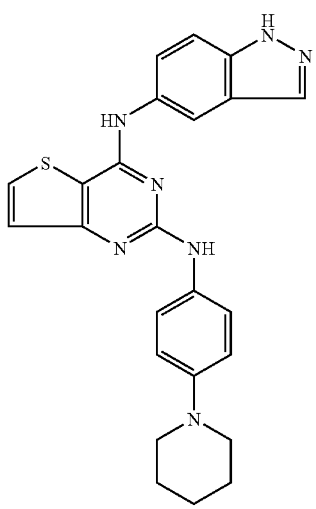 | 441.17 | 441.56 |
| 117 | 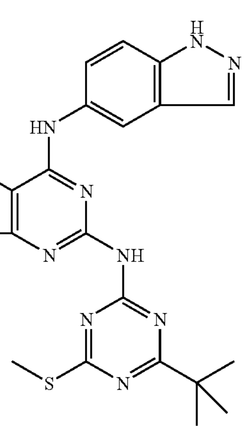 | 463.14 | 463.59 |

| Example No. | Structure | MS (Exact Mass) | MW (calcd) |
|---|---|---|---|
| 118 | 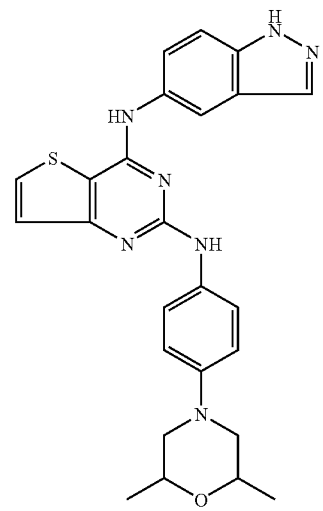 | 471.18 | 471.59 |
| 119 | 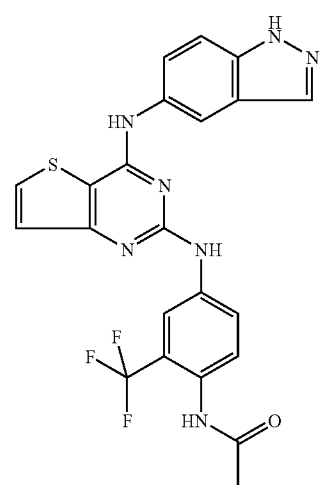 | 483.11 | 483.48 |
| 120 | 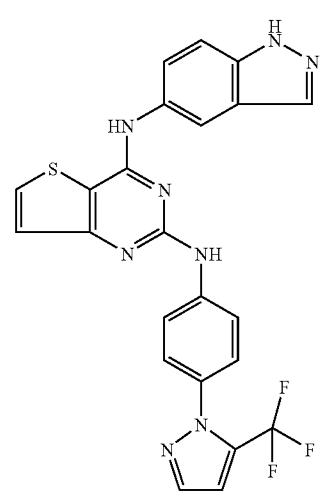 | 492.11 | 492.49 |

-continued

| Example No. | Structure | MS (Exact Mass) | MW (calcd) |
|---|---|---|---|
| 121 | 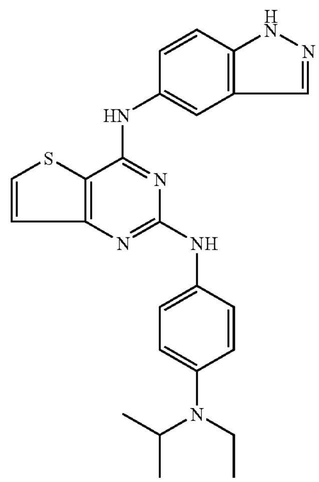 | 443.19 | 443.58 |
| 122 | 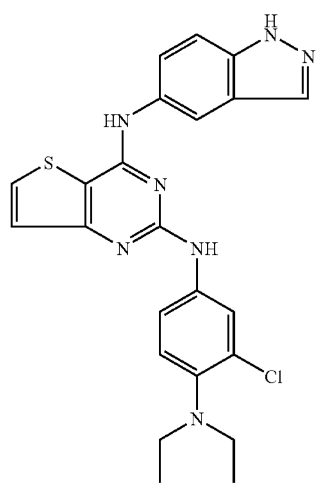 | 463.13 | 463.99 |
| 123 | 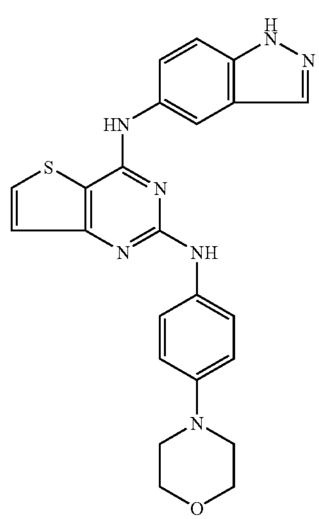 | 443.15 | 443.53 |

| Example No. | Structure | MS (Exact Mass) | MW (calcd) |
|---|---|---|---|
| 124 | 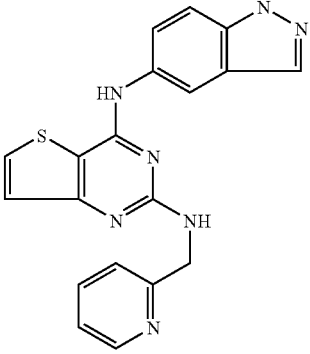 | 373.11 | 373.44 |
| 125 | 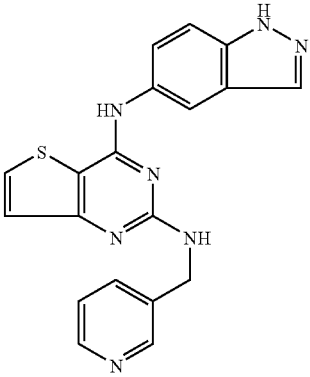 | 373.11 | 373.44 |
| 126 | 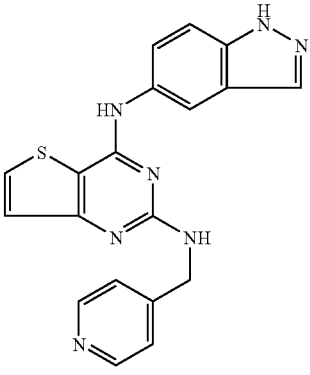 | 373.11 | 373.44 |
| 127 | 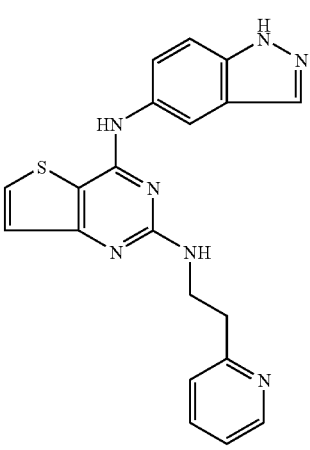 | 387.13 | 387.47 |

-continued

| Example No. | Structure | MS (Exact Mass) | MW (calcd) |
|---|---|---|---|
| 128 | 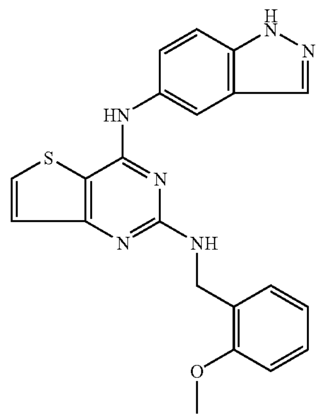 | 402.13 | 402.48 |
| 129 | 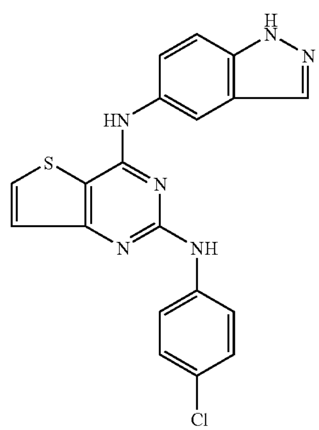 | 392.06 | 392.87 |
| 130 | 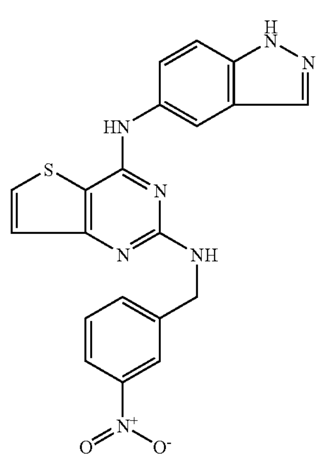 | 417.10 | 417.45 |

-continued
| Example No. | Structure | MS (Exact Mass) | MW (calcd) |
|---|---|---|---|
| 131 | 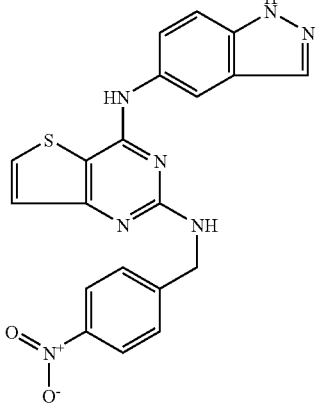 | 417.10 | 417.45 |
| 132 | 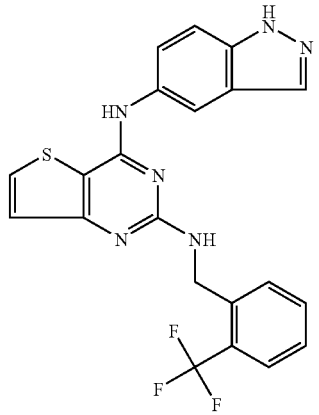 | 440.10 | 440.45 |
| 133 | 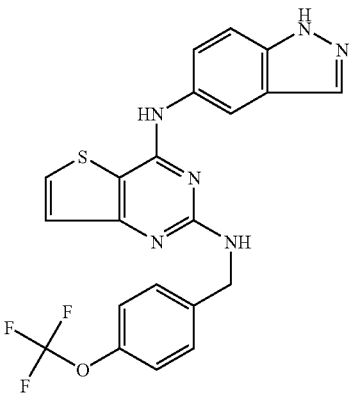 | 456.10 | 456.45 |

| Example No. | Structure | MS (Exact Mass) | MW (calcd) |
|---|---|---|---|
| 134 | *N-(1H-indazol-5-yl)-N'-(3,4-difluorobenzyl)thieno[3,2-d]pyrimidine-2,4-diamine* | 408.10 | 408.43 |
| 135 | *N-(1H-indazol-5-yl)-N'-(3,5-difluorobenzyl)thieno[3,2-d]pyrimidine-2,4-diamine* | 408.10 | 408.43 |
| 136 | *N-(1H-indazol-5-yl)-N'-(3-fluoro-5-(trifluoromethyl)benzyl)thieno[3,2-d]pyrimidine-2,4-diamine* | 458.09 | 458.44 |

-continued

| Example No. | Structure | MS (Exact Mass) | MW (calcd) |
|---|---|---|---|
| 137 | 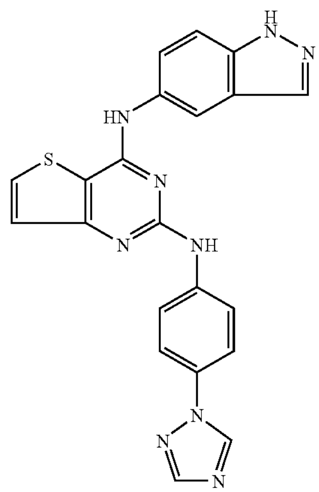 | 425.12 | 425.48 |
| 138 | 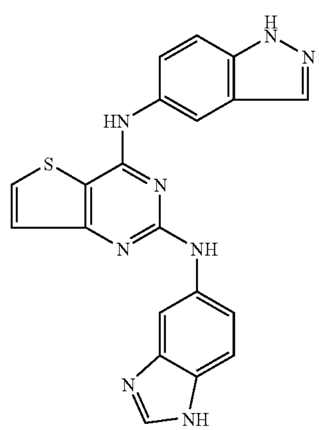 | 398.11 | 398.45 |
| 139 | 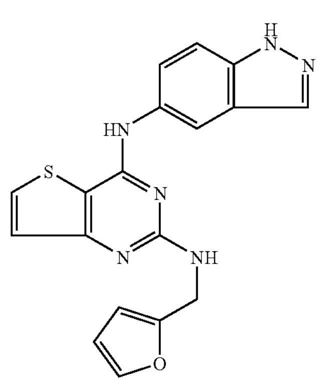 | 362.09 | 362.41 |

| Example No. | Structure | MS (Exact Mass) | MW (calcd) |
|---|---|---|---|
| 140 | 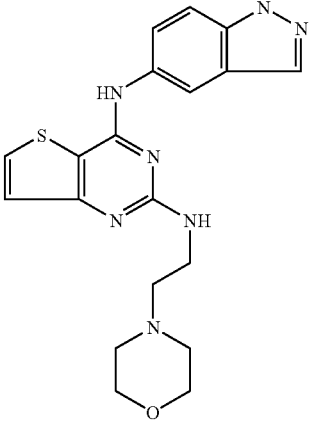 | 395.15 | 395.49 |
| 141 | 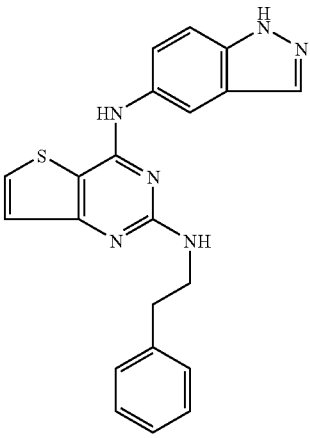 | 386.13 | 386.48 |
| 142 | 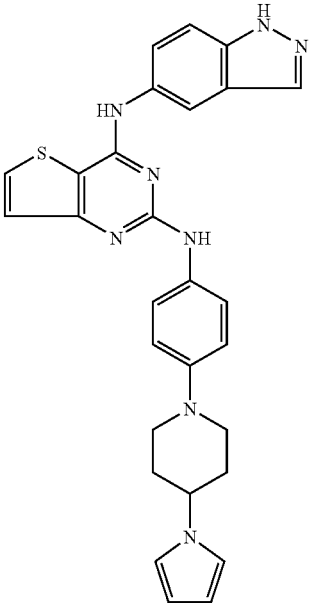 | 506.20 | 506.64 |

-continued
| Example No. | Structure | MS (Exact Mass) | MW (calcd) |
|---|---|---|---|
| 143 | 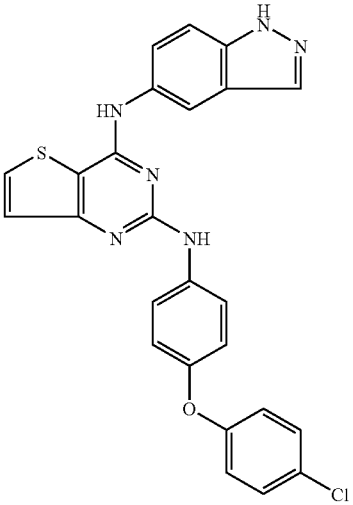 | 484.09 | 484.97 |
| 144 | 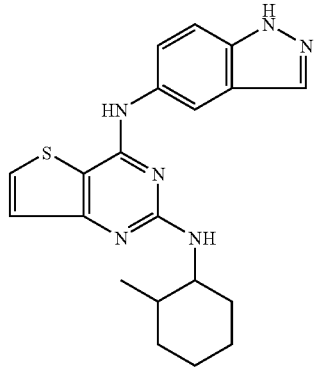 | 378.16 | 378.50 |
| 145 | 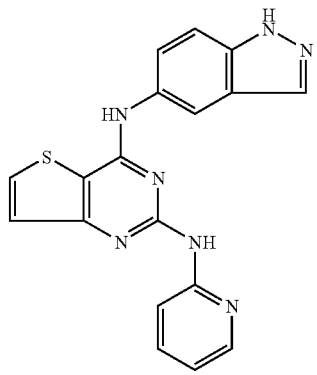 | 359.10 | 359.41 |

-continued
| Example No. | Structure | MS (Exact Mass) | MW (calcd) |
|---|---|---|---|
| 146 | 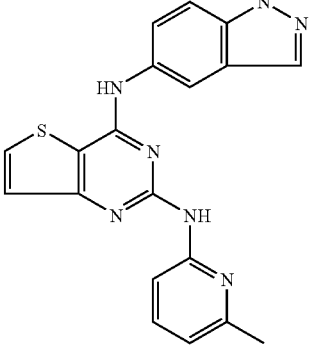 | 373.11 | 373.44 |
| 147 | 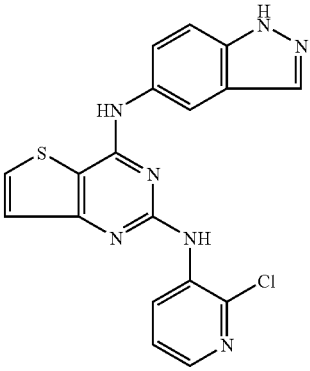 | 393.06 | 393.86 |
| 148 | 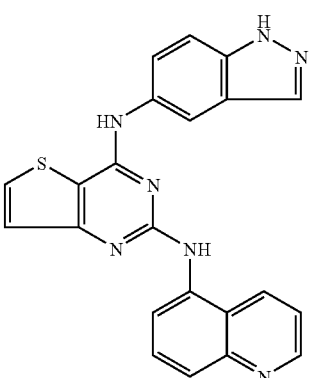 | 409.11 | 409.47 |
| 149 | 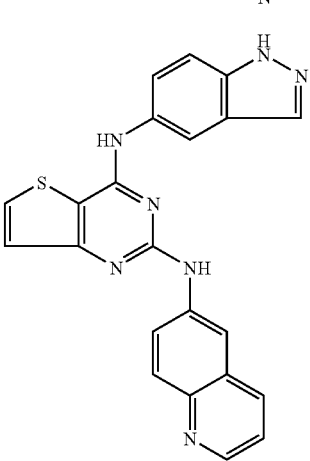 | 409.11 | 409.47 |

| Example No. | Structure | MS (Exact Mass) | MW (calcd) |
|---|---|---|---|
| 150 | 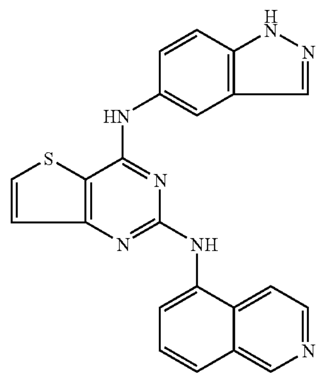 | 409.11 | 409.47 |
| 151 | 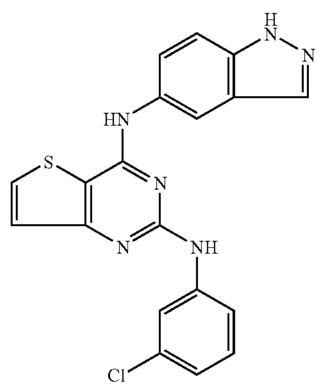 | 392.06 | 392.87 |
| 152 | 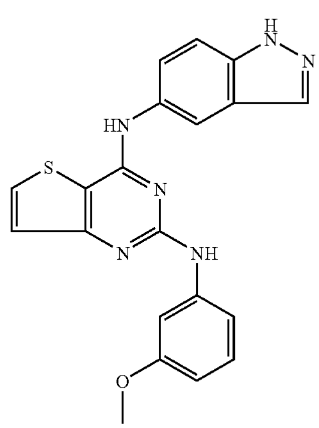 | 388.11 | 388.45 |

-continued

| Example No. | Structure | MS (Exact Mass) | MW (calcd) |
|---|---|---|---|
| 153 | 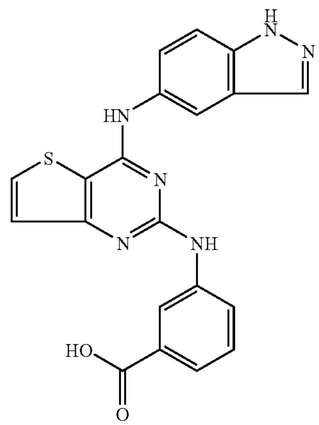 | 402.09 | 402.44 |
| 154 | 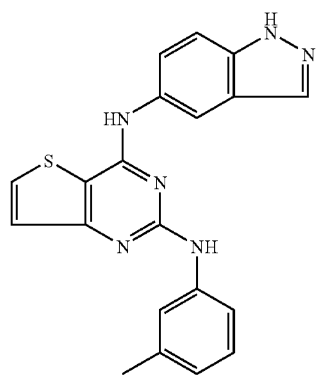 | 372.12 | 372.45 |
| 155 | 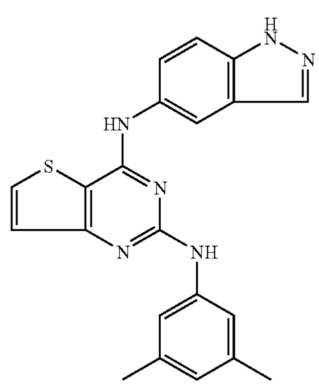 | 386.13 | 386.48 |

-continued
| Example No. | Structure | MS (Exact Mass) | MW (calcd) |
|---|---|---|---|
| 156 | 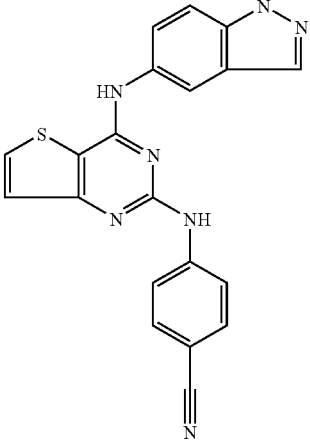 | 383.10 | 383.44 |
| 157 | 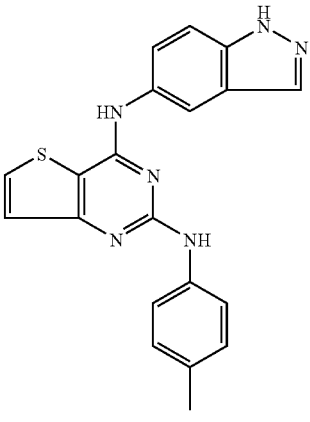 | 372.12 | 372.45 |
| 158 | 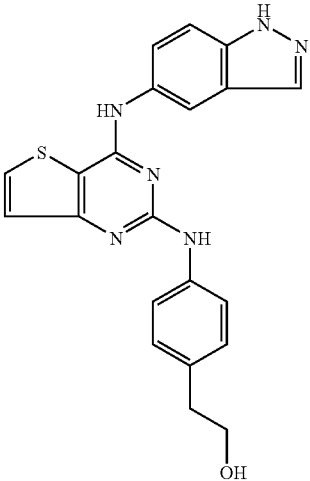 | 402.13 | 402.48 |

-continued

| Example No. | Structure | MS (Exact Mass) | MW (calcd) |
|---|---|---|---|
| 159 | 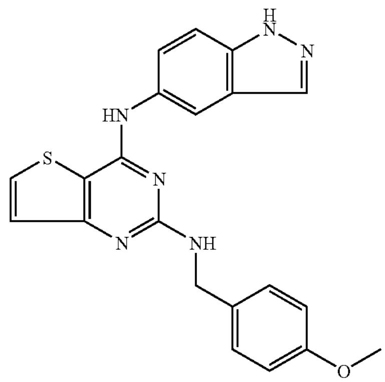 | 402.13 | 402.48 |
| 160 | 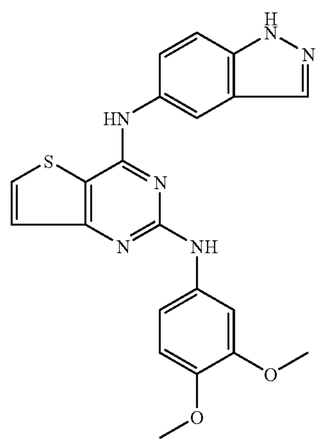 | 418.12 | 418.48 |
| 161 | 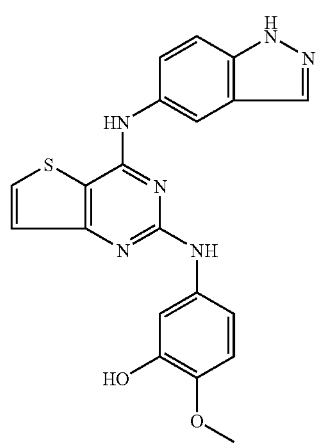 | 404.11 | 404.45 |

-continued

| Example No. | Structure | MS (Exact Mass) | MW (calcd) |
|---|---|---|---|
| 162 | 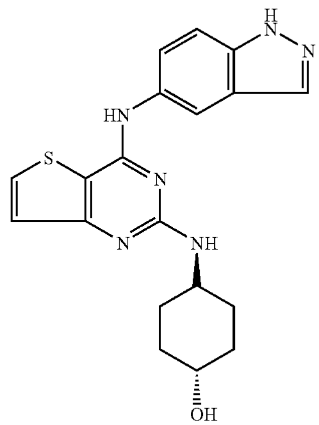 | 380.14 | 380.47 |
| 163 | 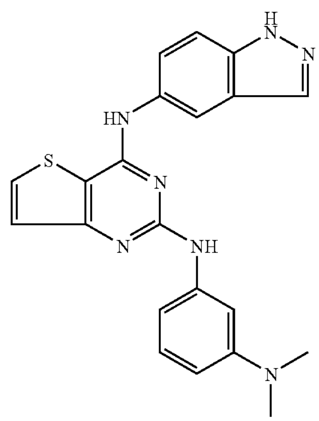 | 401.14 | 401.50 |
| 164 | 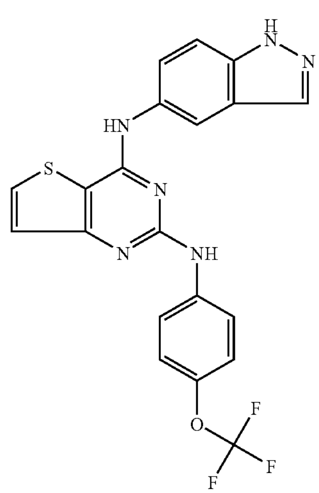 | 442.08 | 442.42 |

-continued

| Example No. | Structure | MS (Exact Mass) | MW (calcd) |
|---|---|---|---|
| 165 | 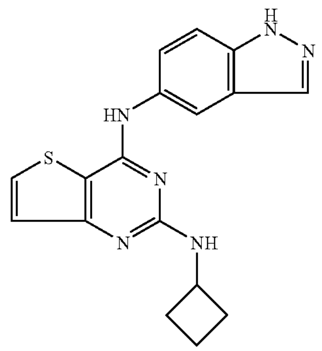 | 336.12 | 336.42 |
| 166 | 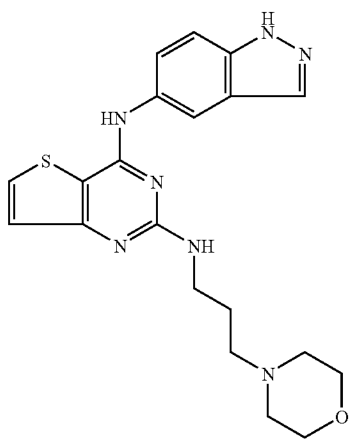 | 409.17 | 409.52 |
| 167 | 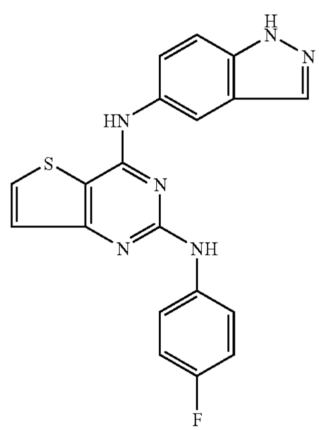 | 376.09 | 376.42 |
| 168 | 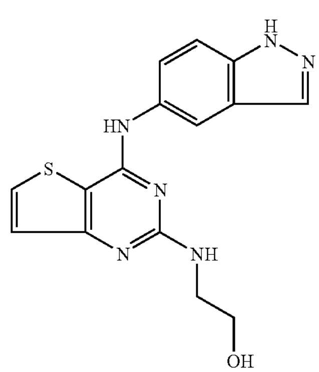 | 326.09 | 326.38 |

-continued

| Example No. | Structure | MS (Exact Mass) | MW (calcd) |
|---|---|---|---|
| 169 | 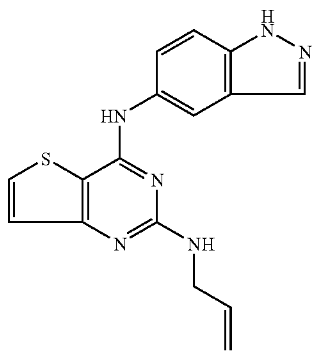 | 322.10 | 322.39 |
| 170 | 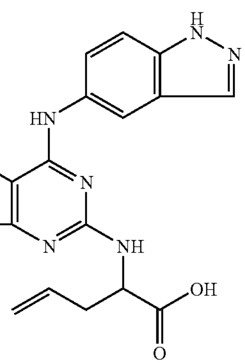 | 380.11 | 380.43 |
| 171 | 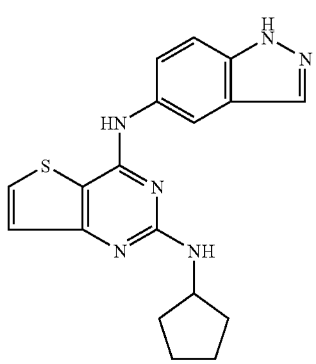 | 350.13 | 350.45 |
| 172 | 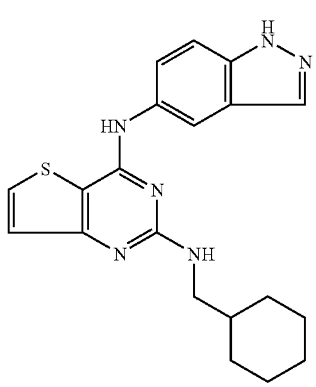 | 378.16 | 378.50 |

-continued

| Example No. | Structure | MS (Exact Mass) | MW (calcd) |
|---|---|---|---|
| 173 | 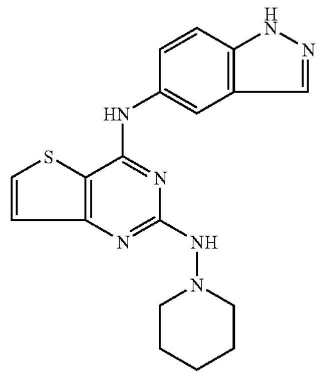 | 365.14 | 365.46 |
| 174 | 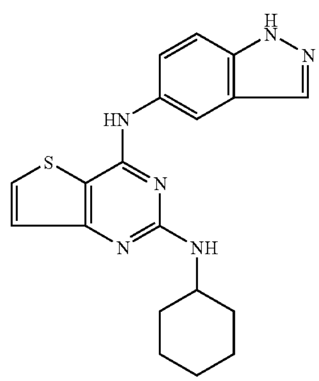 | 364.15 | 364.47 |
| 175 | 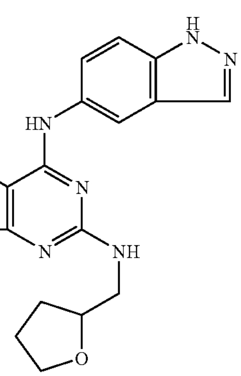 | 366.13 | 366.45 |

| Example No. | Structure | MS (Exact Mass) | MW (calcd) |
|---|---|---|---|
| 176 | 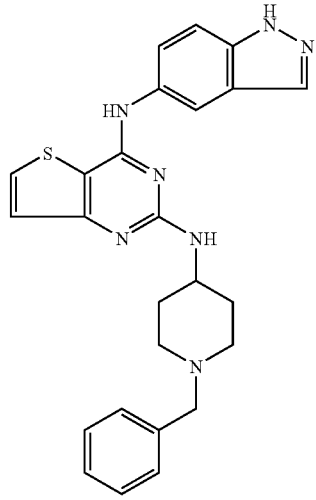 | 455.19 | 455.59 |
| 177 | 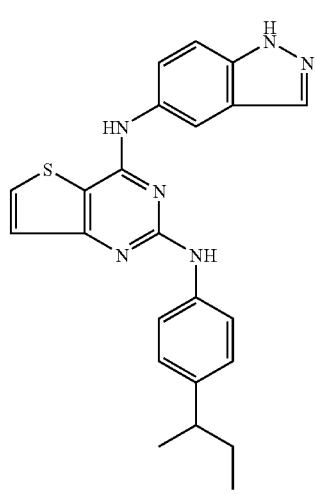 | 414.16 | 414.53 |
| 178 | 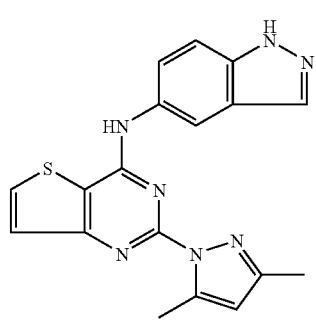 | 361.11 | 361.43 |

| Example No. | Structure | MS (Exact Mass) | MW (calcd) |
|---|---|---|---|
| 179 | 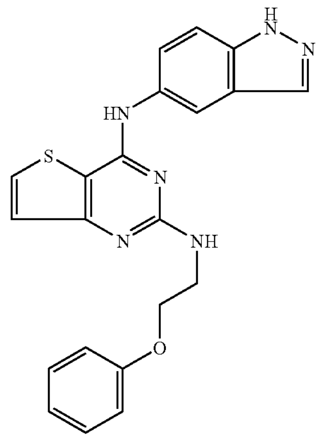 | 402.13 | 402.48 |
| 180 | 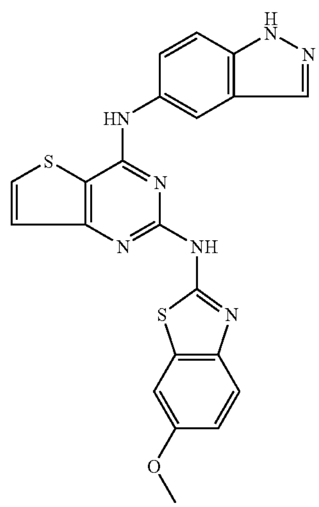 | 445.08 | 445.53 |
| 181 | 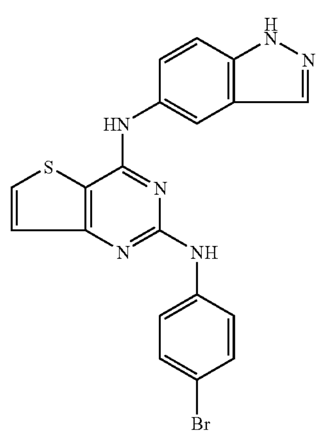 | 436.01 | 437.33 |

| Example No. | Structure | MS (Exact Mass) | MW (calcd) |
|---|---|---|---|
| 182 | 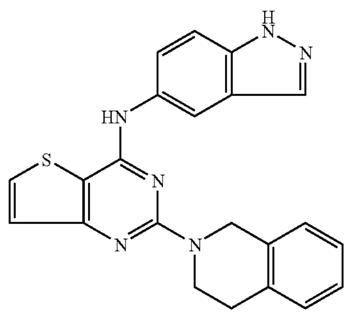 | 398.13 | 398.49 |
| 183 | 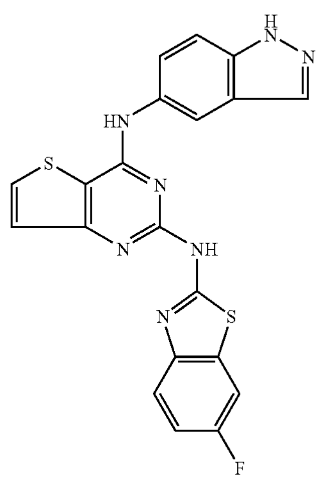 | 433.06 | 433.49 |
| 184 | 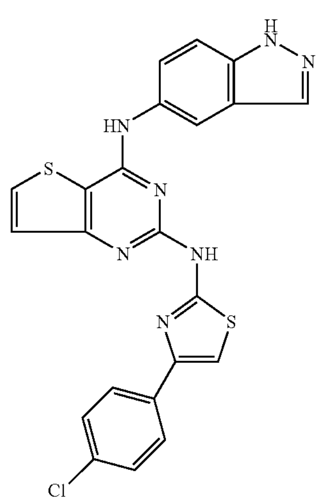 | 475.04 | 475.98 |

-continued

| Example No. | Structure | MS (Exact Mass) | MW (calcd) |
|---|---|---|---|
| 185 | 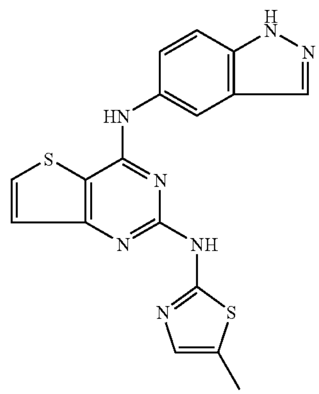 | 379.07 | 379.47 |
| 186 | 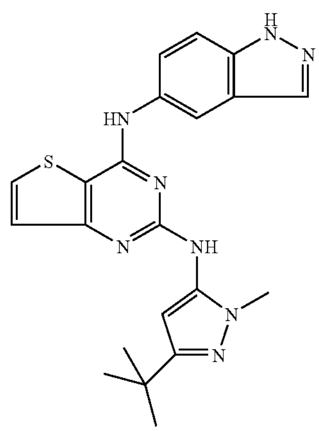 | 418.17 | 418.53 |
| 187 | 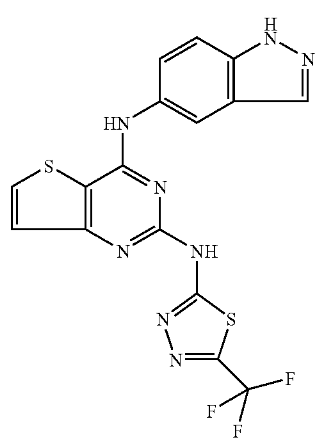 | 434.03 | 434.43 |

| Example No. | Structure | MS (Exact Mass) | MW (calcd) |
|---|---|---|---|
| 188 | 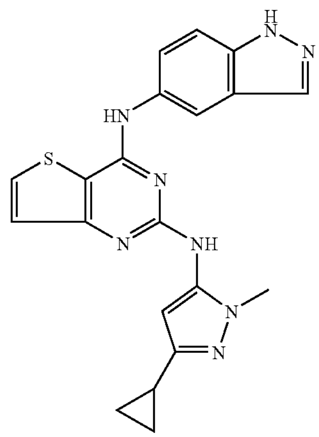 | 402.14 | 402.48 |
| 189 | 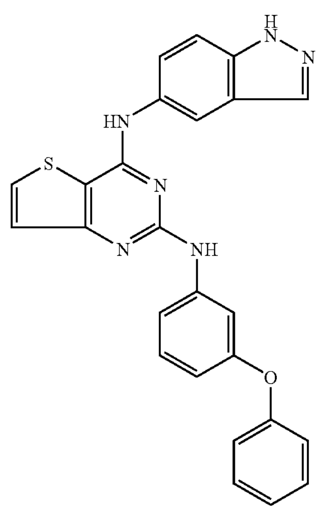 | 450.13 | 450.52 |
| 190 | 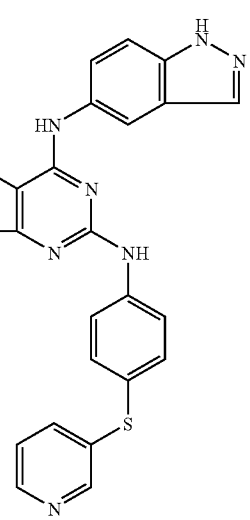 | 467.10 | 467.58 |

-continued

| Example No. | Structure | MS (Exact Mass) | MW (calcd) |
|---|---|---|---|
| 191 | 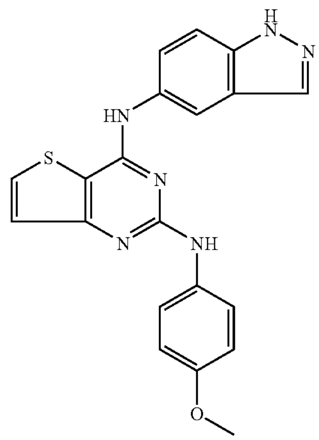 | 388.11 | 388.45 |
| 192 | 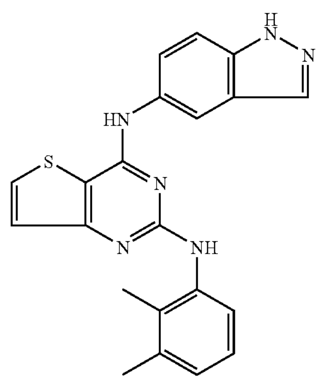 | 386.13 | 386.48 |
| 193 | 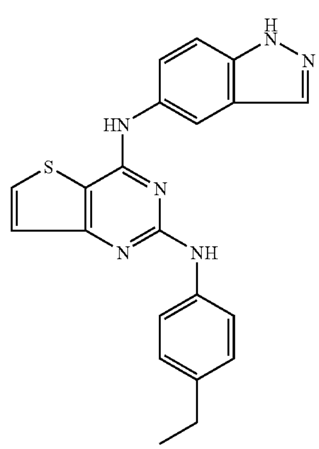 | 386.13 | 386.48 |

-continued
| Example No. | Structure | MS (Exact Mass) | MW (calcd) |
|---|---|---|---|
| 194 | 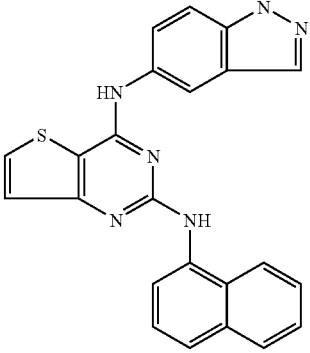 | 408.12 | 408.49 |
| 195 | 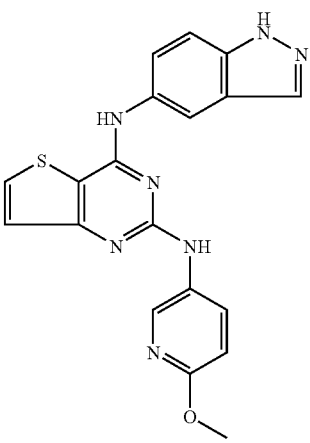 | 389.11 | 389.44 |
| 196 | 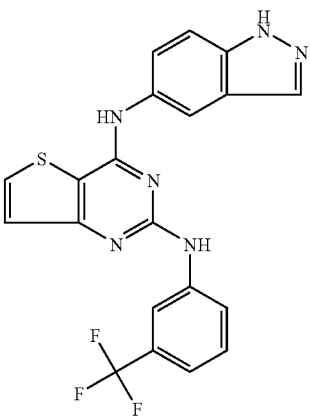 | 426.09 | 426.42 |

| Example No. | Structure | MS (Exact Mass) | MW (calcd) |
|---|---|---|---|
| 197 | 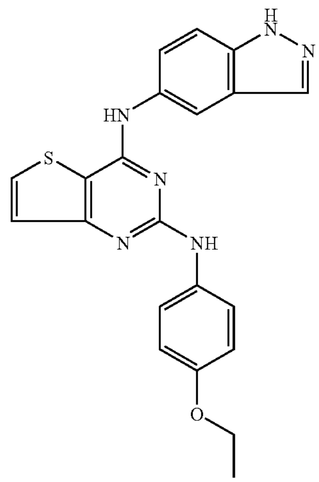 | 402.13 | 402.48 |
| 198 | 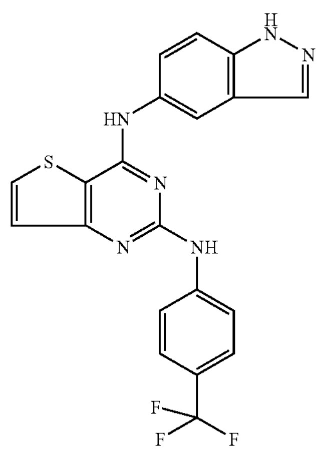 | 426.09 | 426.42 |
| 199 | 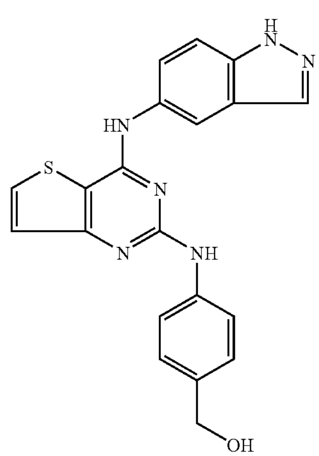 | 388.11 | 388.45 |

-continued
| Example No. | Structure | MS (Exact Mass) | MW (calcd) |
|---|---|---|---|
| 200 | 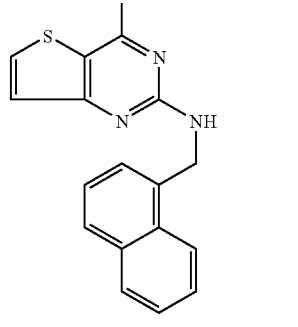 | 422.13 | 422.51 |
| 201 | 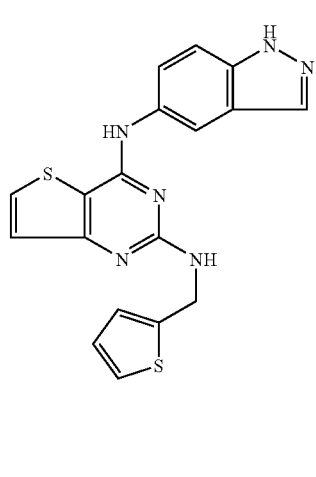 | 378.07 | 378.48 |
| 202 | 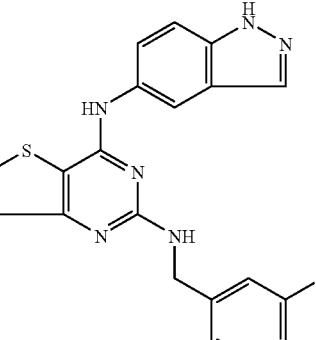 | 440.04 | 441.34 |

-continued
| Example No. | Structure | MS (Exact Mass) | MW (calcd) |
|---|---|---|---|
| 203 | 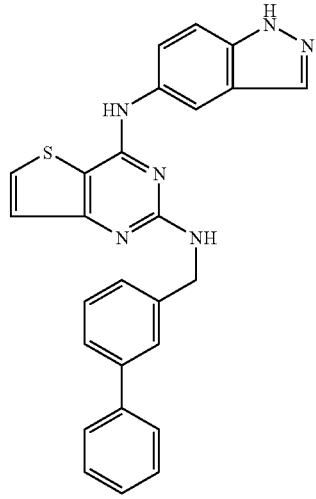 | 448.15 | 448.55 |
| 204 | 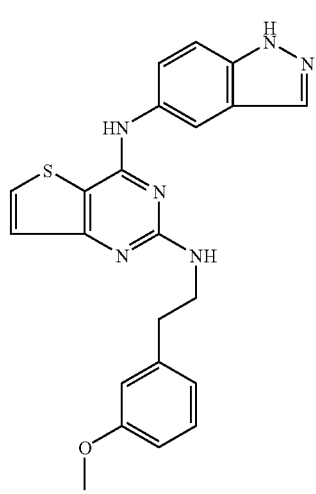 | 416.14 | 416.51 |
| 205 | 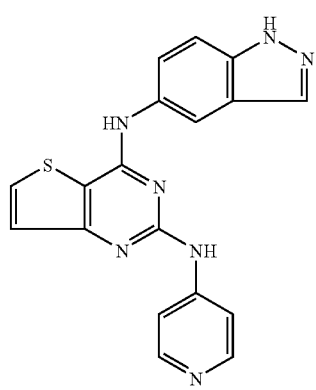 | 359.10 | 359.41 |

-continued

| Example No. | Structure | MS (Exact Mass) | MW (calcd) |
|---|---|---|---|
| 206 | 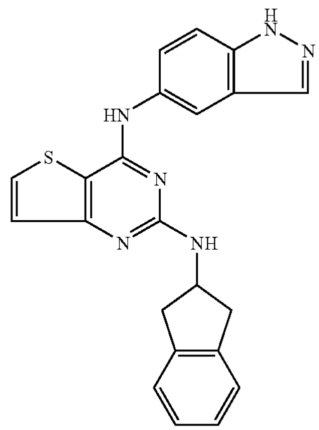 | 398.13 | 398.49 |
| 207 | 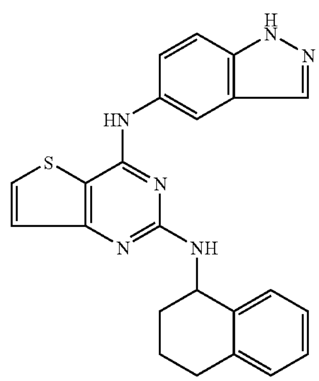 | 412.15 | 412.52 |
| 208 | 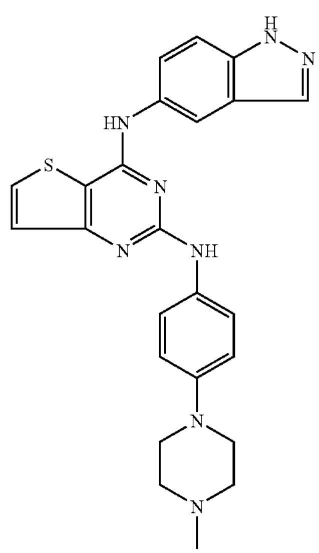 | 456.18 | 456.58 |

-continued

| Example No. | Structure | MS (Exact Mass) | MW (calcd) |
|---|---|---|---|
| 209 | 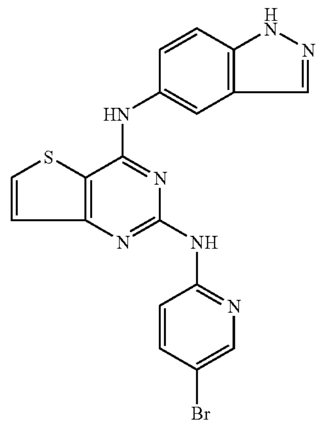 | 437.01 | 438.32 |
| 210 | 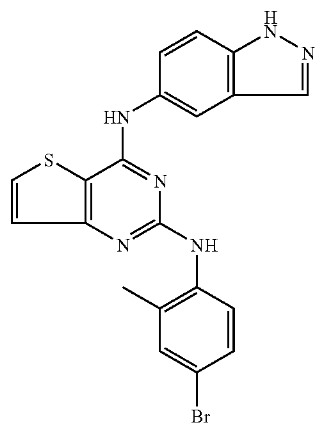 | 450.03 | 451.35 |
| 211 | 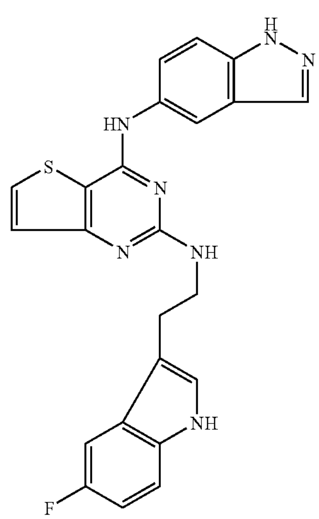 | 443.13 | 443.51 |

| Example No. | Structure | MS (Exact Mass) | MW (calcd) |
|---|---|---|---|
| 212 | 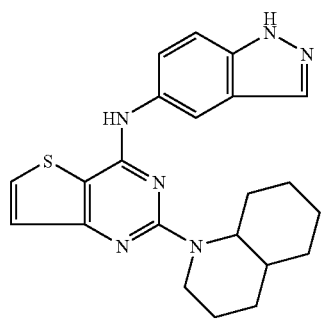 | 404.18 | 404.54 |
| 213 | 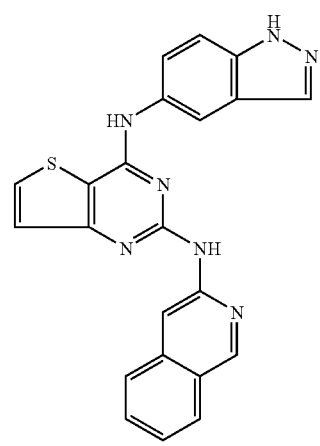 | 409.11 | 409.47 |
| 214 | 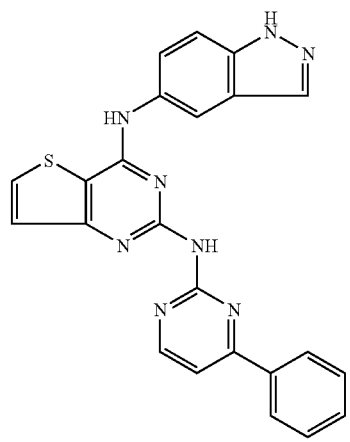 | 436.12 | 436.50 |

| Example No. | Structure | MS (Exact Mass) | MW (calcd) |
|---|---|---|---|
| 215 | 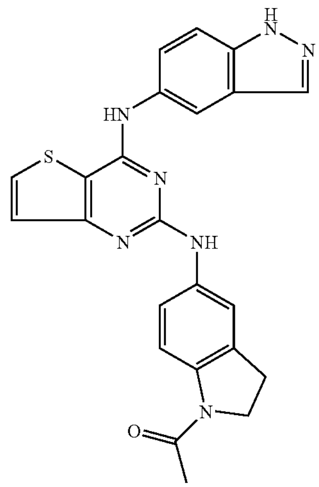 | 441.14 | 441.52 |
| 216 | 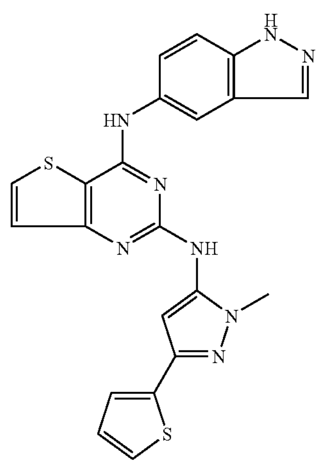 | 444.09 | 444.54 |
| 217 | 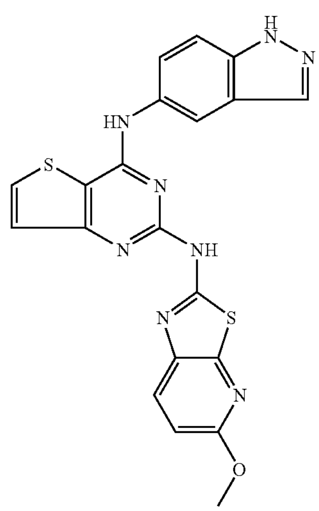 | 446.07 | 446.51 |

-continued

| Example No. | Structure | MS (Exact Mass) | MW (calcd) |
|---|---|---|---|
| 218 | 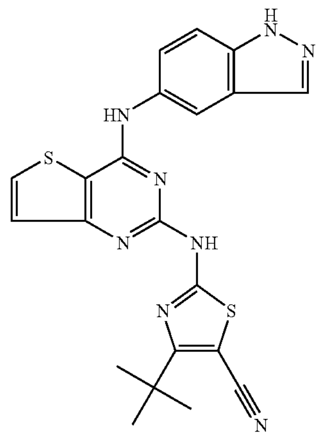 | 446.11 | 446.56 |
| 219 | 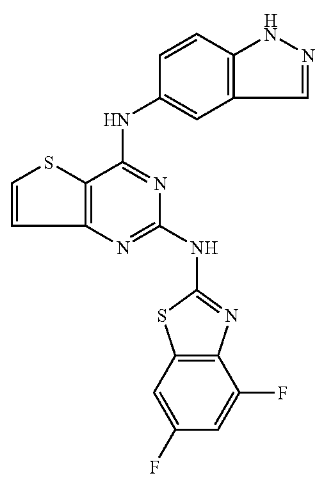 | 451.05 | 451.48 |
| 220 | 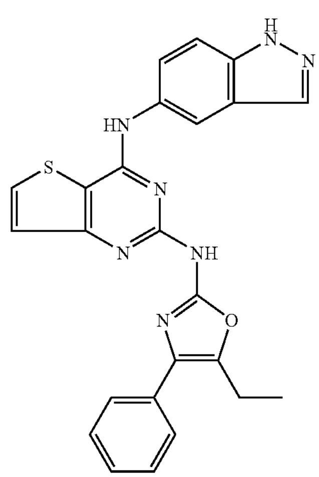 | 453.14 | 453.53 |

-continued

| Example No. | Structure | MS (Exact Mass) | MW (calcd) |
|---|---|---|---|
| 221 | 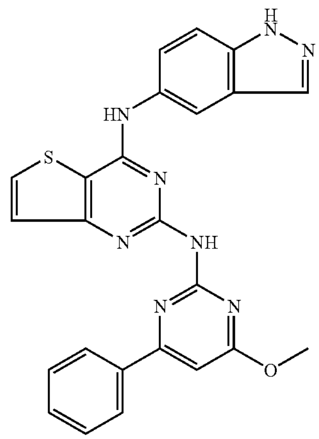 | 466.13 | 466.53 |
| 222 | 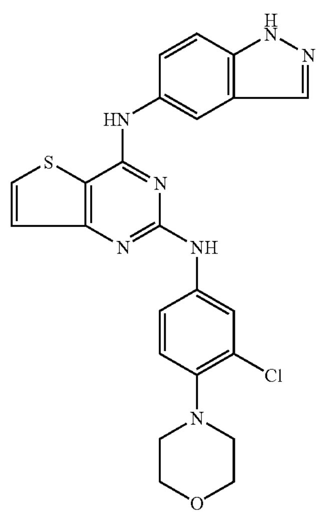 | 477.11 | 477.98 |
| 223 | 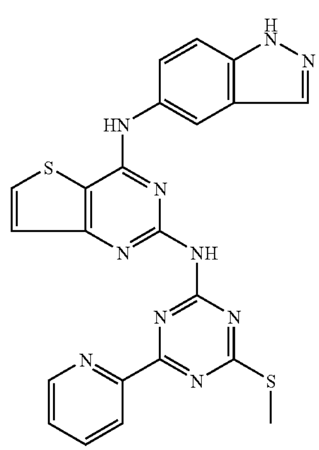 | 484.10 | 484.57 |

| Example No. | Structure | MS (Exact Mass) | MW (calcd) |
|---|---|---|---|
| 224 | 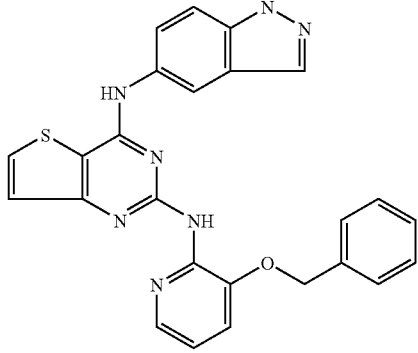 | 465.14 | 465.54 |
| 225 | 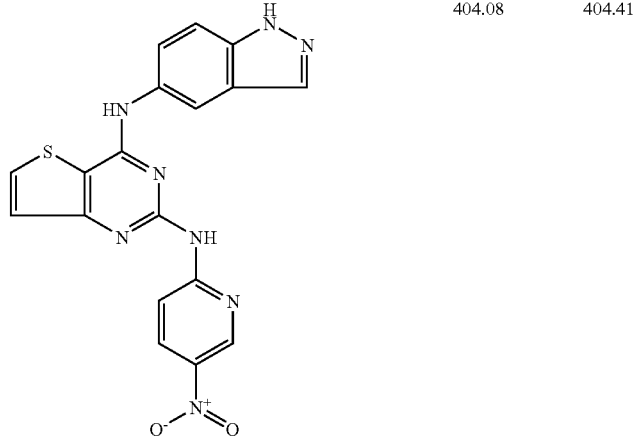 | 404.08 | 404.41 |
| 226 | 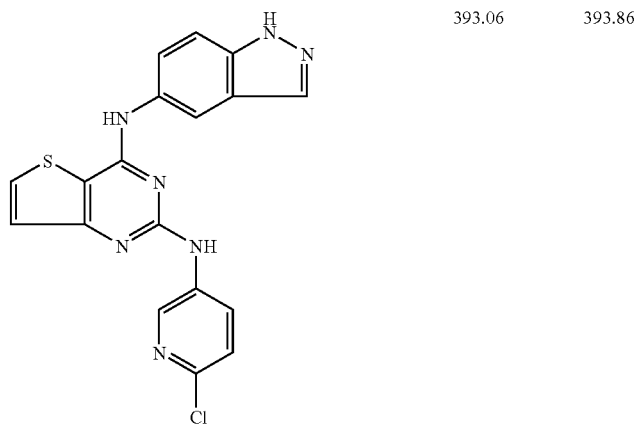 | 393.06 | 393.86 |

| Example No. | Structure | MS (Exact Mass) | MW (calcd) |
|---|---|---|---|
| 227 | 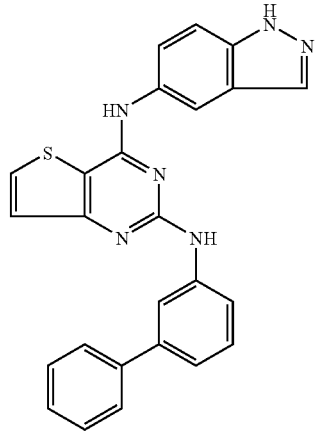 | 434.13 | 434.52 |
| 228 | 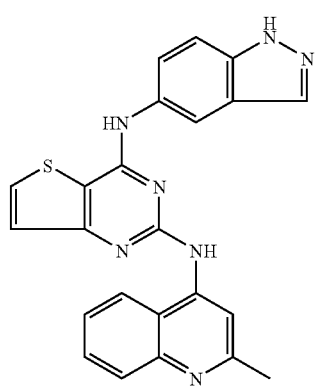 | 423.13 | 423.50 |
| 229 | 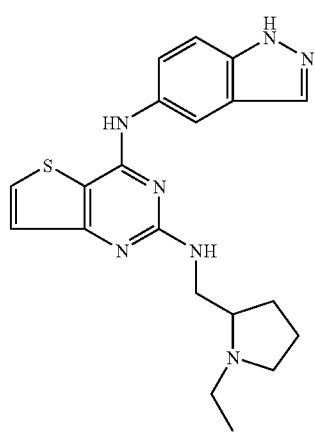 | 393.17 | 393.52 |

| Example No. | Structure | MS (Exact Mass) | MW (calcd) |
|---|---|---|---|
| 230 | 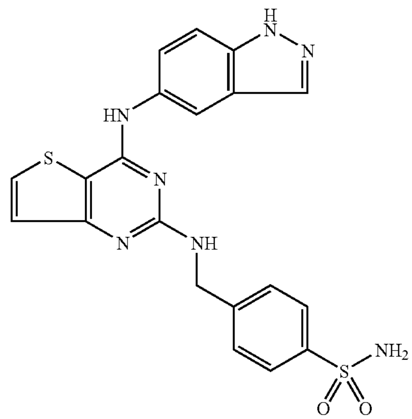 | 451.09 | 451.53 |
| 231 | 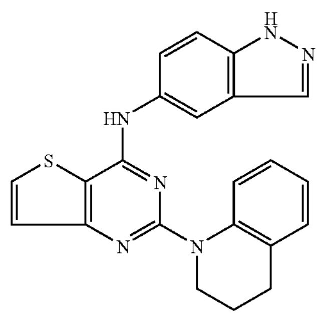 | 398.13 | 398.49 |
| 232 | 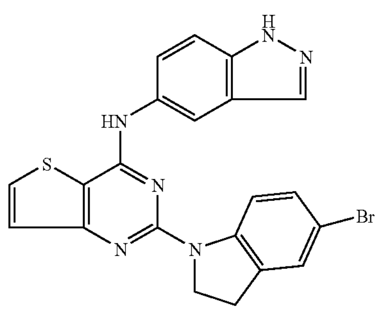 | 462.03 | 463.37 |
| 233 | 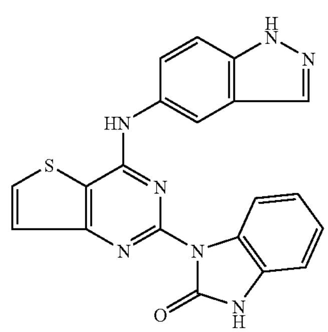 | 399.09 | 399.44 |

-continued

| Example No. | Structure | MS (Exact Mass) | MW (calcd) |
|---|---|---|---|
| 234 | 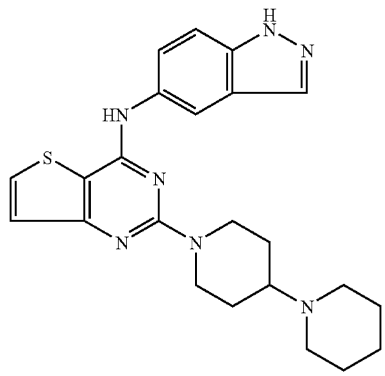 | 433.20 | 433.58 |
| 235 | 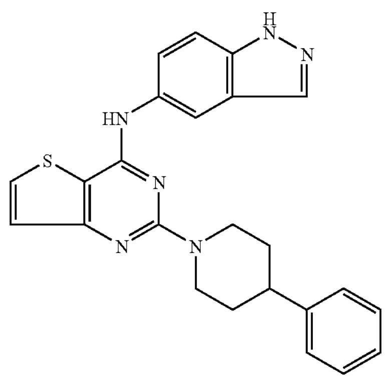 | 426.16 | 426.55 |
| 236 | 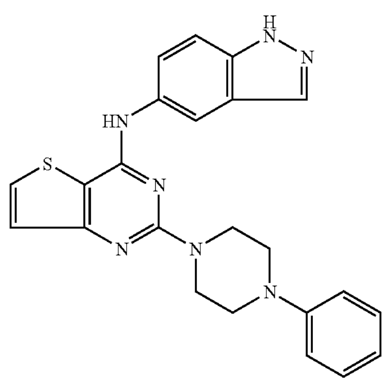 | 427.16 | 427.53 |
| 237 | 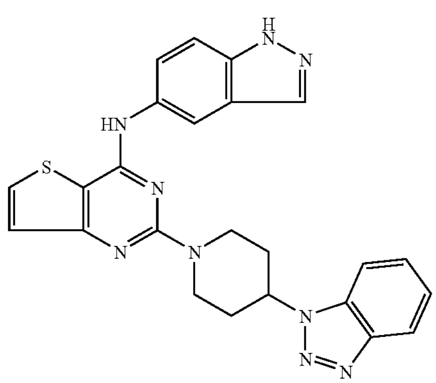 | 467.16 | 467.56 |

-continued

| Example No. | Structure | MS (Exact Mass) | MW (calcd) |
|---|---|---|---|
| 238 | 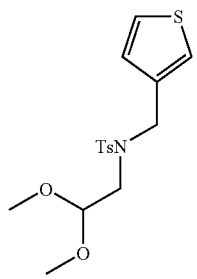 | 457.17 | 457.56 |

INTERMEDIATES

Intermediate A

Preparation of thieno[3,2-c]pyridin-2-ylboronic acid

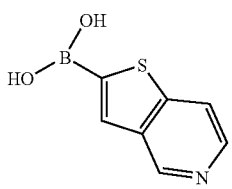
(A)

Step 1: Preparation of 2,2-dimethoxy-N-(3-thienylmethyl)ethanamine

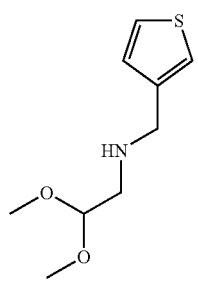

To 3-thiophenecarboxaldehyde (8.75 mL) cooled to 0° C. was added aminoacetaldehyde dimethylacetal (14.2 mL). The clear solution was stirred at room temperature for 60 h. The solution was diluted with ethanol and hydrogenated at 56 psi in the presence of 10% Pd/C (5 g) overnight. The catalyst was filtered off and washed with MeOH. The solvent was removed by rotary evaporation and co-evaporated with toluene to afford an oil (19 g, 94% yield).

Step 2: Preparation of N-(2,2-dimethoxyethyl)-4-methyl-N-3-thienylmethyl)-benzenesulfonamide

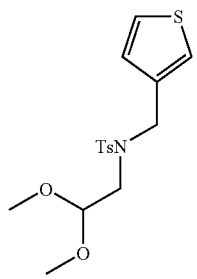

To a solution of the compound prepared in step 1, (19 g, 95 mmol) in EtOAc (50 mL) at 15° C. was added triethylamine (12 mL, 85.5 mmol), followed by p-toluenesulfonyl chloride (16.3 g, 85.5 mmol). After the addition was complete, the solution was stirred at rt overnight. The reaction mixture was diluted with EtOAc and washed with water three times, HCl (1.0 M), and with satd $Na_2CO_3$. The solution was dried over $MgSO_4$, filtered, and concentrated to give a precipitate (31 g, 87 mmol, 91% yield). Rf=0.16 (EtOAc/hexane, 1/9).

Step 3: Preparation of thieno[3,2-c]pyridine

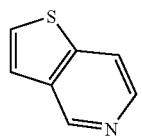

To a solution of the compound from step 2 (31 g, 0.087 mol) in dioxane (80 mL) was added conc HCl (45 mL). The solution was heated to reflux temperature overnight. The mixture was cooled to rt and washed with $CH_2Cl_2$. The aqueous phase was basified with aqueous $NH_4OH$ while cooling with ice and extracted with $CH_2CH_2$. The organic washings were combined and evaporated to dryness. The residue was purified by silica gel column chromatography (25% EtOAc in hexanes) to afford a white precipitate. The precipitate was dissolved with CH$_2$Cl$_2$, dried over MgSO$_4$, filtered, and concentrated to give 5.97 g of white precipitate (50% yield).

Step 4: Preparation of

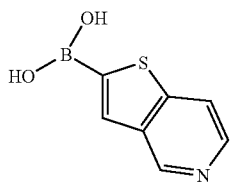

(A)

To a solution of (0.3 g) in THF (15 mL) was added n-BuLi (1.4 mL, 1.6 M in hexane) at −78° C. The solution was stirred at −78° C. for 70 min and triisopropyl borate (0.52 mL, 2.27 mmol) was added. The solution was stirred for an additional 30 min at −78° C., and then at room temperature for 30 min. The solvent was concentrated under reduced pressure and the crude product was used without purification.

Intermediate B

Preparation of 4-(4-morpholinyl)phenylboronic acid

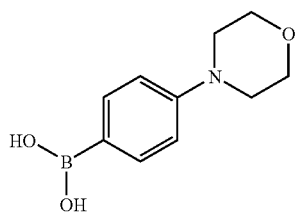

(B)

Step 1: Preparation of 4-(4-bromophenyl)morpholine

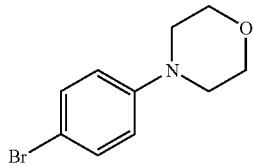

A solution of 1-bromo-4-iodobenzene (5.0 g, 18 mmol), morpholine (1.85 mL, 21 mmol), sodium tert-butoxide (2.4 g, 25 mmol), 18-crown-6 (6.6 g, 25 mmol) in THF (150 mL) was purged with Ar for 20 min, then BINAP (0.11 g, 0.18 mmol) and Pd$_2$(dba)$_3$ (0.16 g, 0.18 mmol) was added. The mixture turned dark after stirring at room temperature overnight. The solvent was concentrated under reduced pressure and the residue was dissolved in diethyl ether and washed with water. The organic phase was mixed with silica gel, and the solvent was evaporated to dryness. The residue was purified by silica gel column chromatography (EtOAc in hexanes 5%) to of white precipitate (250 mg, 5% yield). $^1$H NMR (CDCl$_3$): 7.3 (d, 2H), 6.85 (d, 4H), 3.1 (d, 4H).

Step 2: Preparation of 4-(4-morpholinyl)phenylboronic acid

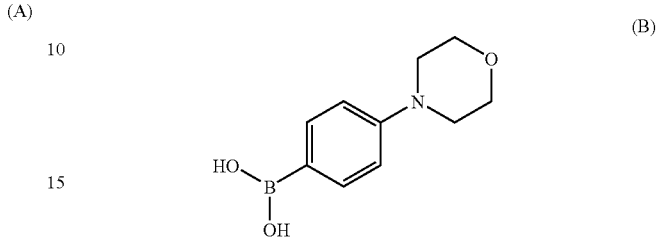

(B)

To a solution of the compound prepared in step 1 (0.3 g) in THF (15 mL) was added n-BuLi (0.74 mL, 2 M in pentane) at 78° C. After 1 h triisopropyl borate (0.86 mL) was added at −78° C. The solution was warmed up slowly from −78° C. to room temperature and was stirred overnight. The solution was added to aqueous NH$_4$Cl, a white precipitate formed, and EtOAc was added. The organic solution was separated, concentrated and co-evaporated with toluene. The residue washed twice with THF and filtered. The filtrate was concentrated and dried under high vacuum to give 0.25 g of light yellow precipitate. LC/MS m/z 208 (M+H)$^+$.

The preceding examples can be repeated with similar success by substituting the generically or specifically described reactants and/or operating conditions of this invention for those used in the preceding examples.

We claim:
1. A compound of the formula

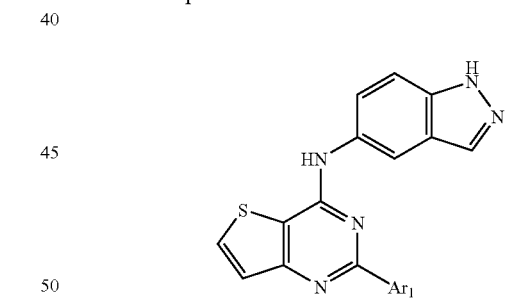

wherein Ar$_1$ is

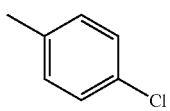

(1)

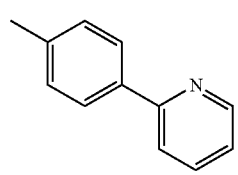

(2)

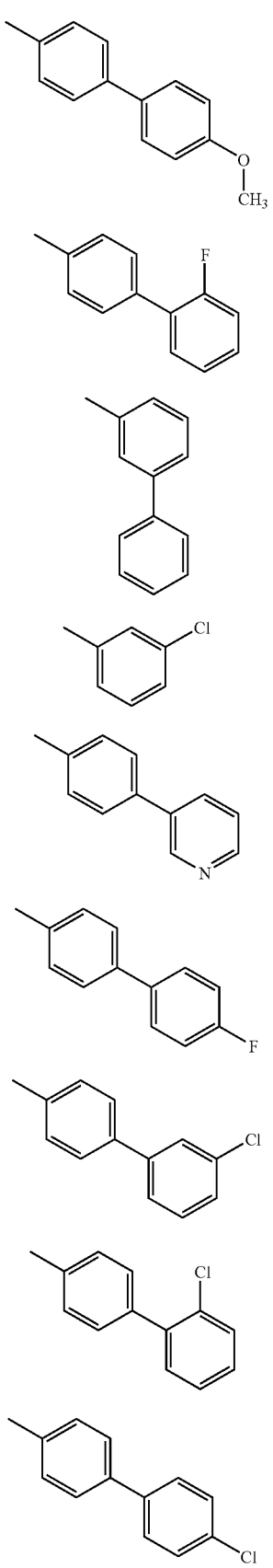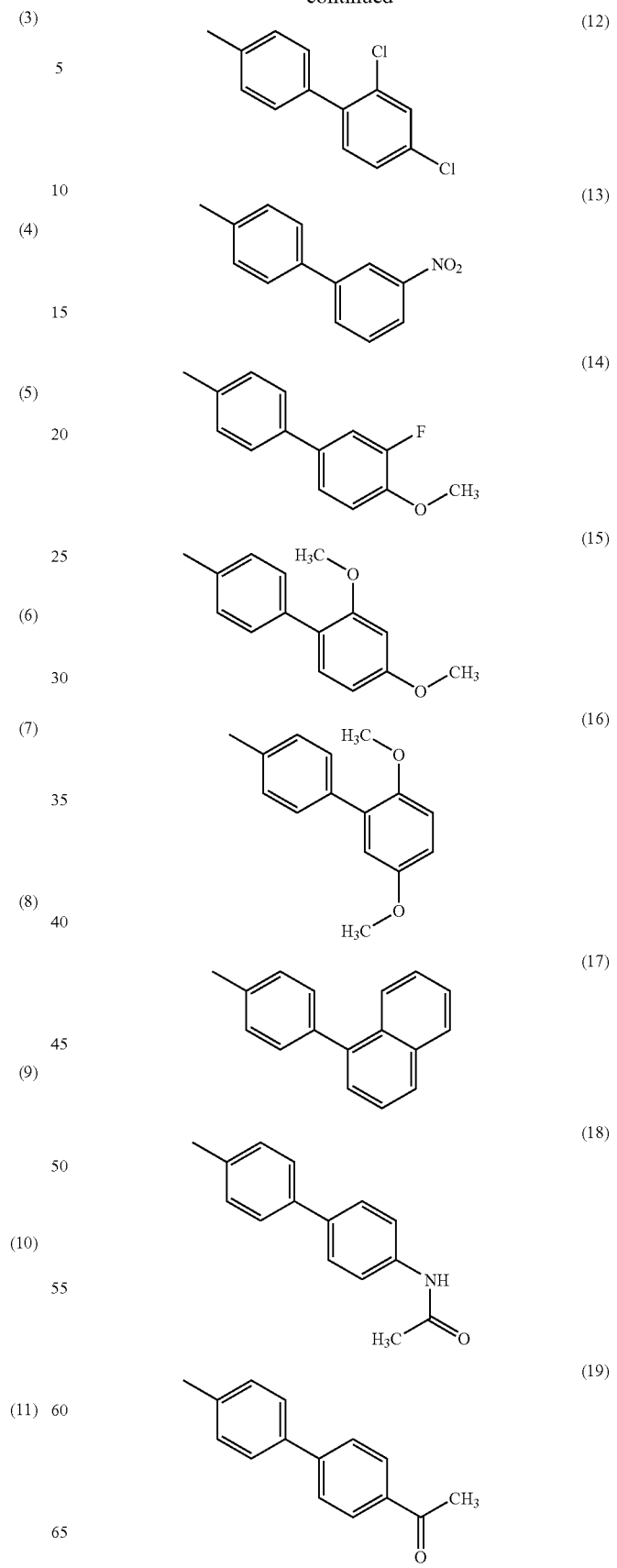

-continued
(20) 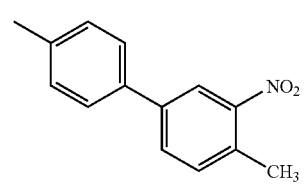
(21) 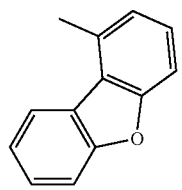
(22) 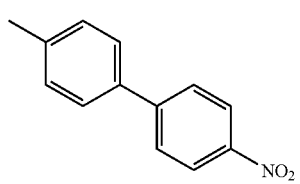
(23) 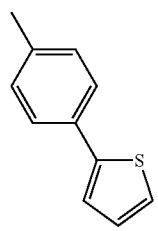
(24) 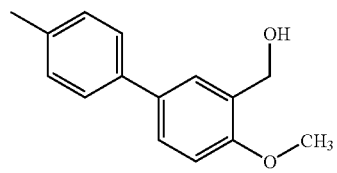
(25) 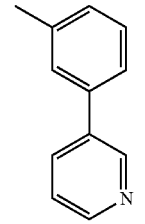
(26) 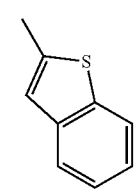
(27) 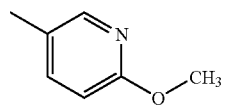
-continued
(28) 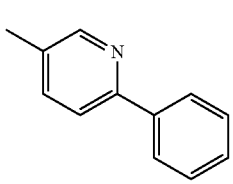
(29) 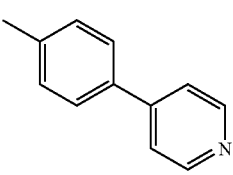
(30) 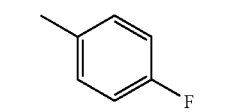
(31) 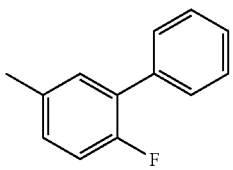
(32) 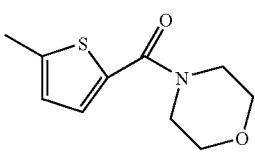
(33) 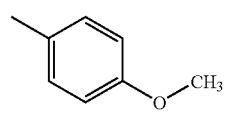
(34) 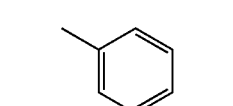
(35) 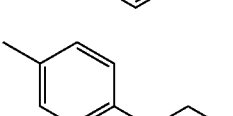
(36) 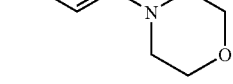
(37) 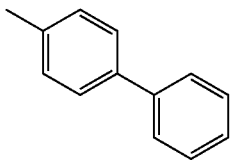
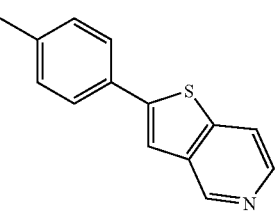

-continued
(38) 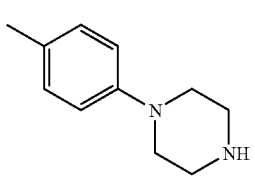
(39) 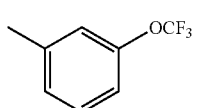
(40) 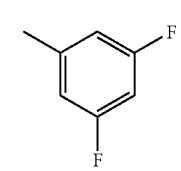
(41) 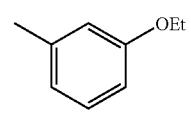
(42) 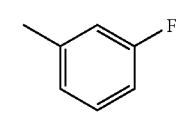
(43) 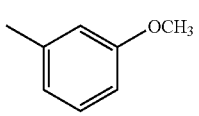
(44) 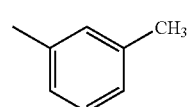
(45) 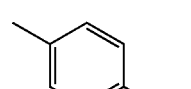
(46) 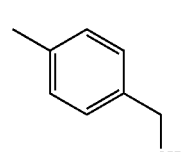
(47) 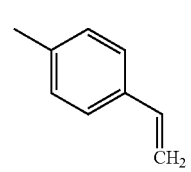
(48) 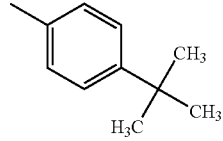
-continued
(49) 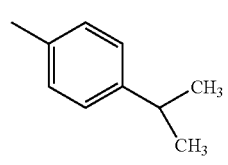
(50) 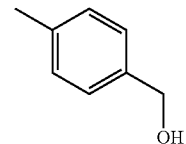
(51) 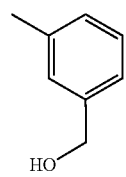
(52) 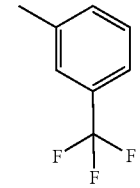
(53) 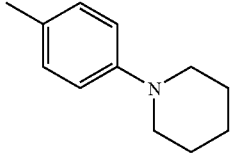
(54) 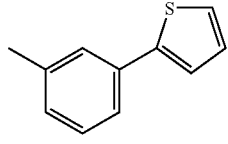
(55) 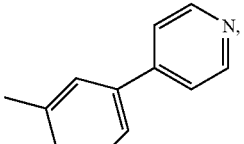
or a pharmaceutically acceptable salt thereof.
2. A compound of the formula
(56) 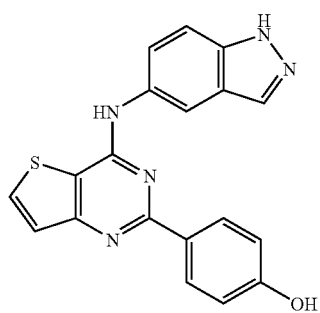

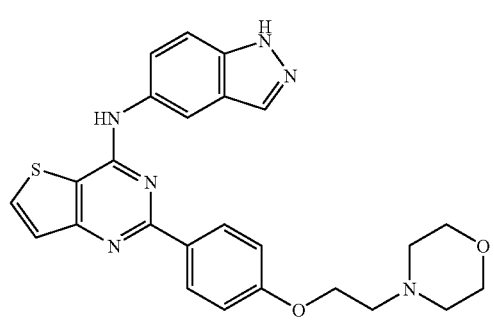 (57)
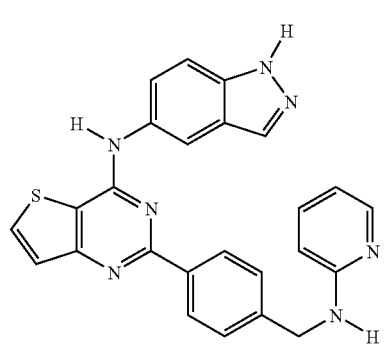 (58)
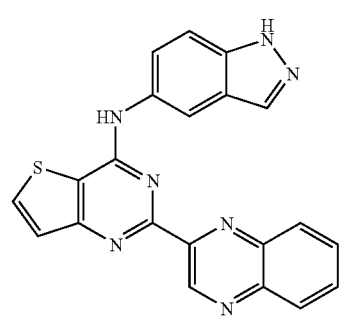 (59)
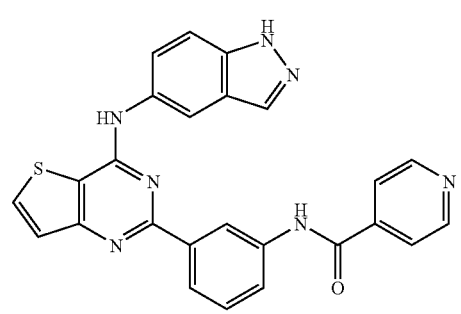 (66)
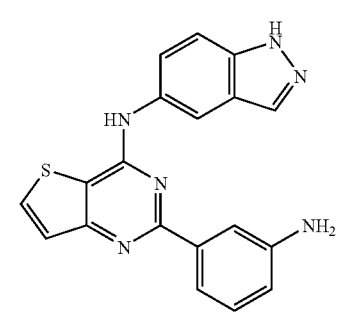 (67)
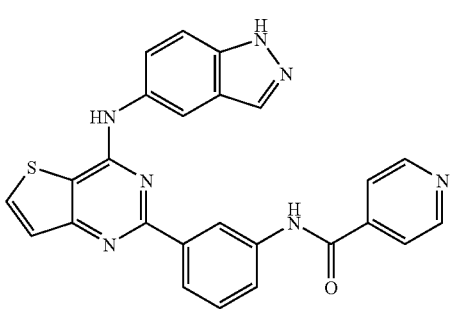 (68)
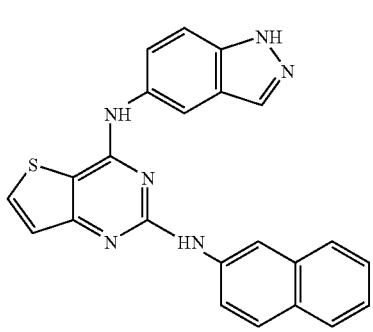 (69)
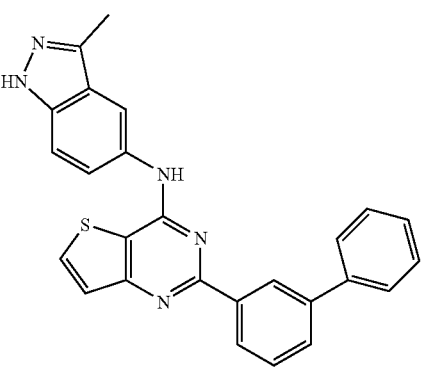 (70)
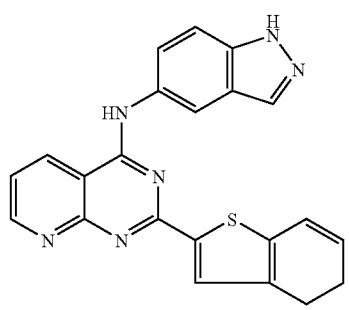 (71)
or a pharmaceutically acceptable salt thereof.

3. A compound of the formula
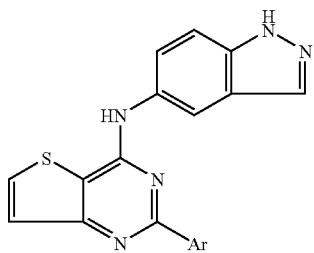
wherein Ar is
3-aminophenyl, 3-isonicotinamido-phenyl, 5-(1H-indolyl)amino, or 4-phenoxyanilino.
4. A compound of the formula
(72)
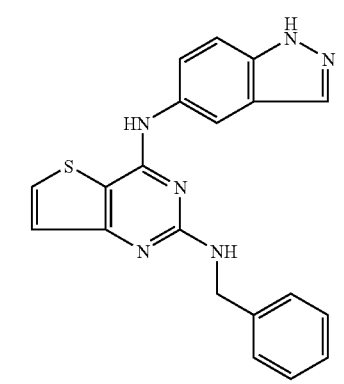
(73)
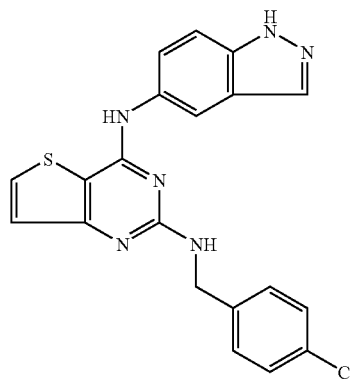
(74)
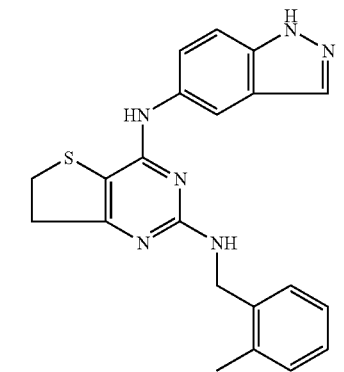
-continued
(75)
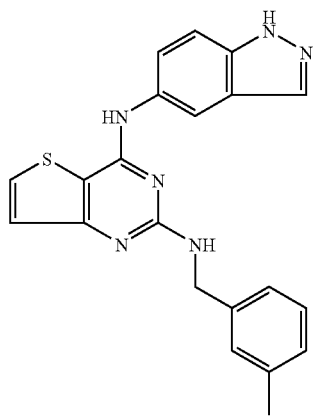
(76)
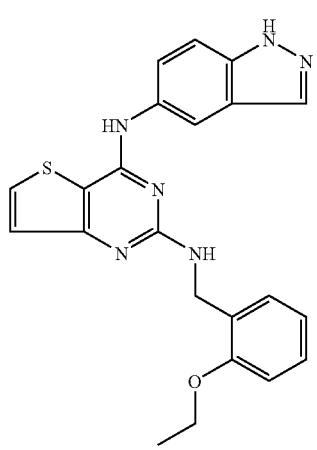
(77)
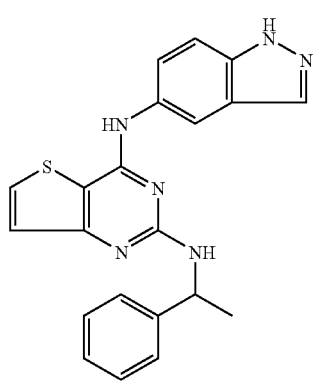

-continued
(78) 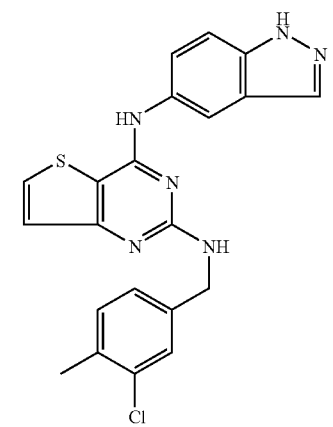
(79) 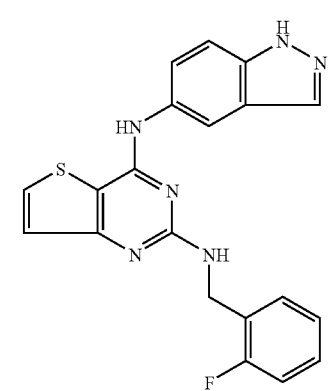
(80) 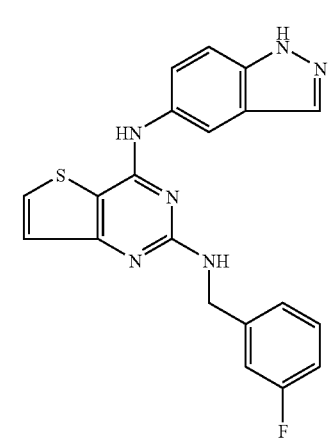
(81) 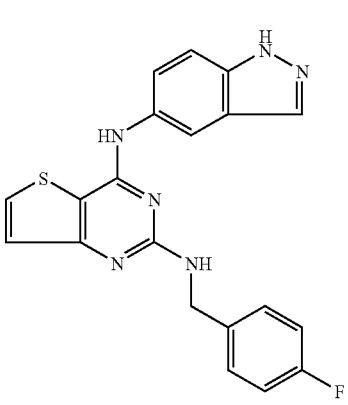
-continued
(82)
(83)
(84)
(85)

-continued
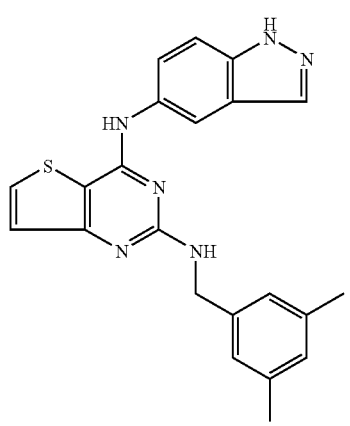
(86)
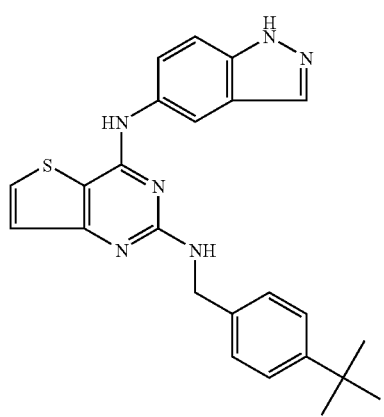
(87)
(88)
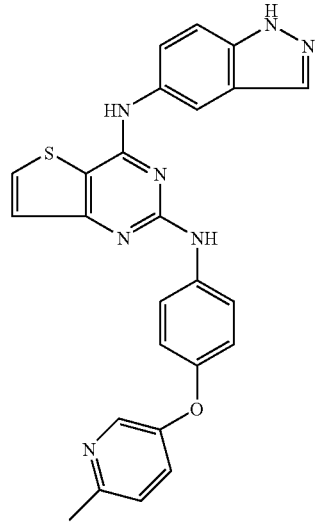
(89)
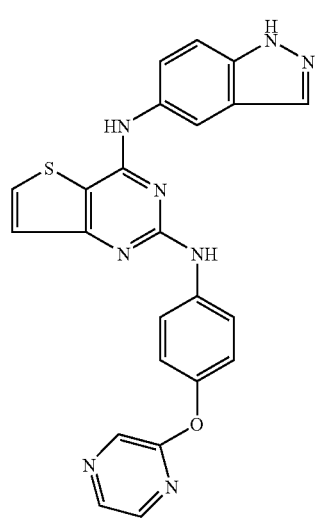
(90)
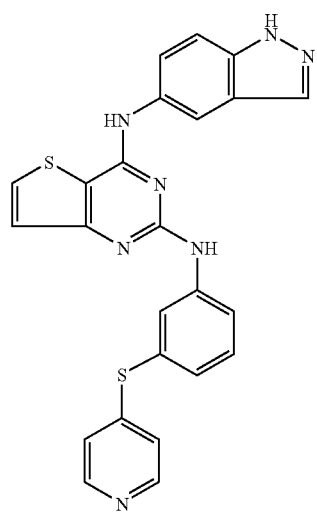
(91)

-continued (92)

(93)

(94)

(95)

(96)

(97)

-continued
(104)
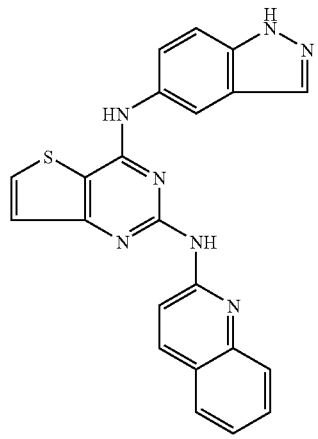
(105)
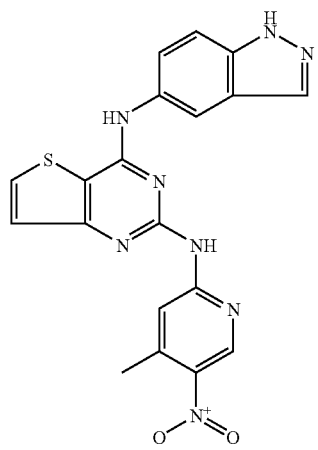
(106)
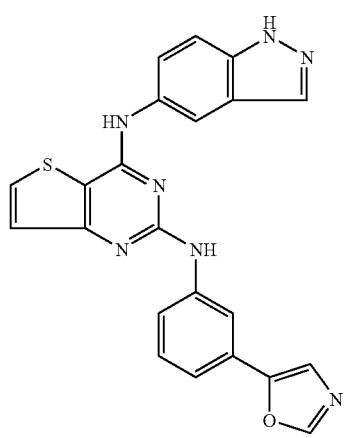
-continued
(107)
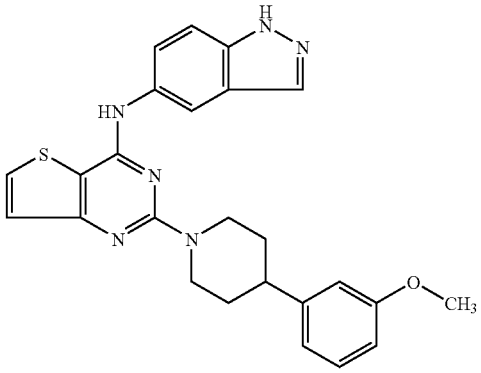
(108)
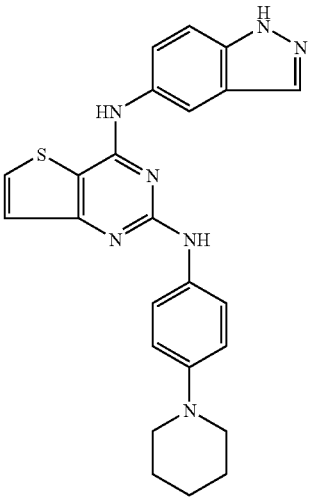
(109)
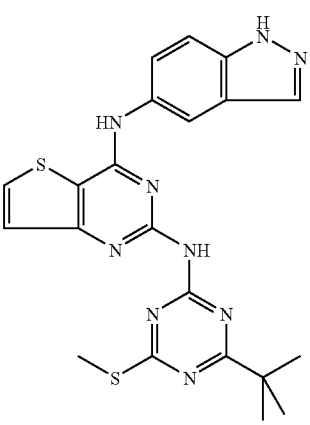

-continued (110)
(111)
(112)
(113)
(114)
(115)

-continued
(116)
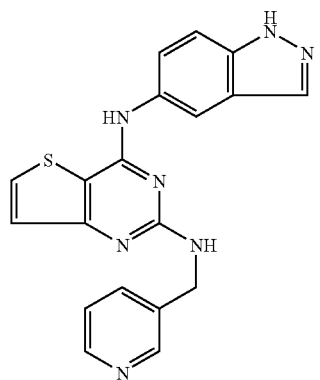
(117)
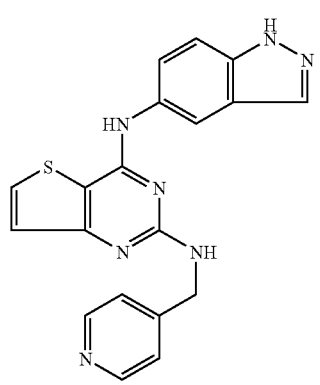
(118)
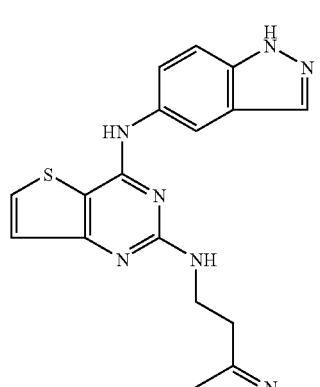
(119)
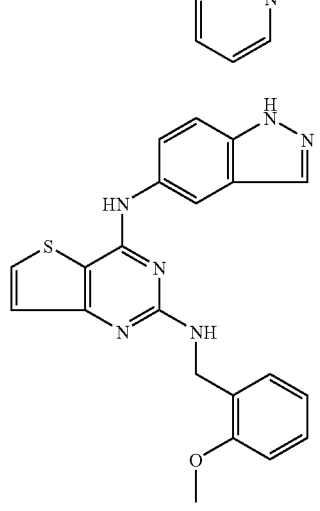
-continued
(120)
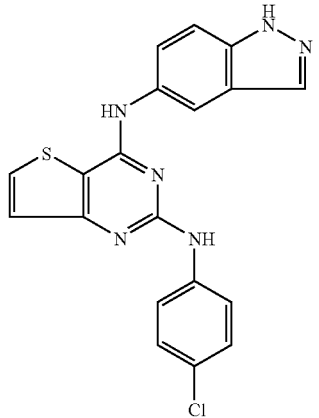
(121)
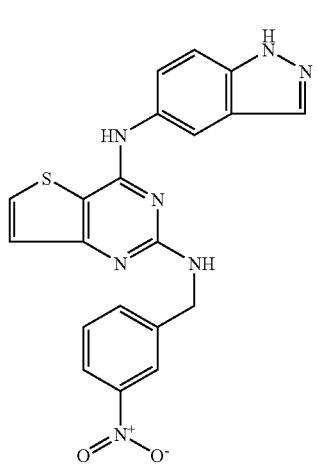
(122)
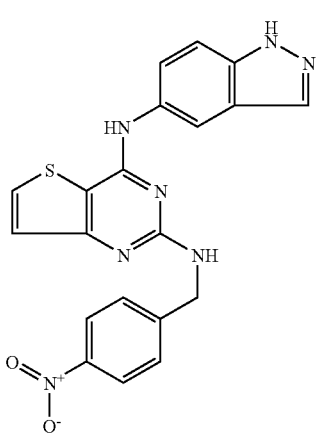

-continued
(123)
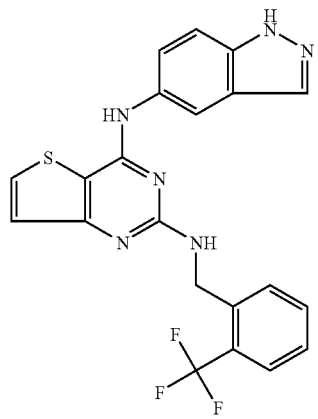
(124)
(125)
-continued
(126)
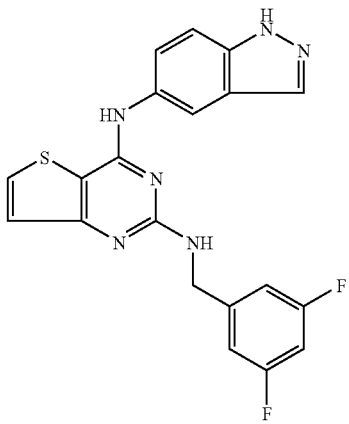
(127)
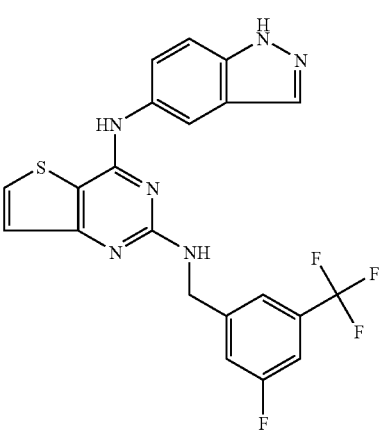
(128)
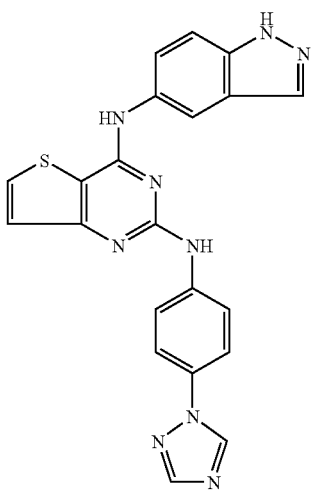

(129) 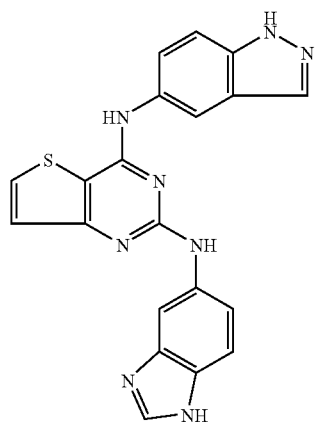
(130) 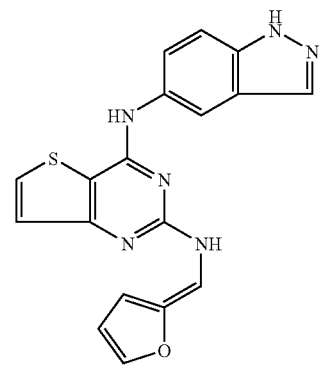
(131) 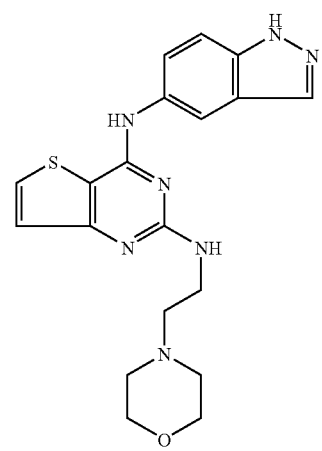
(132) 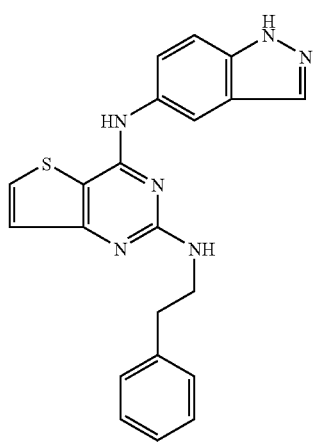
(133) 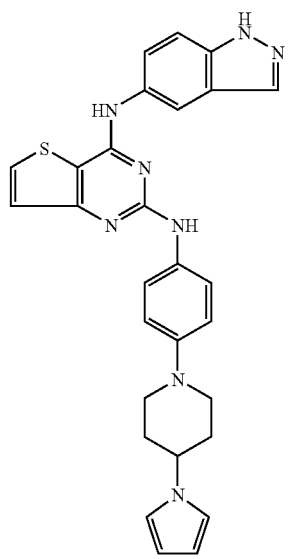
(134) 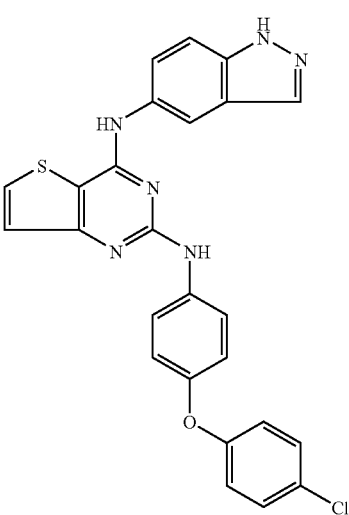

-continued
(135)
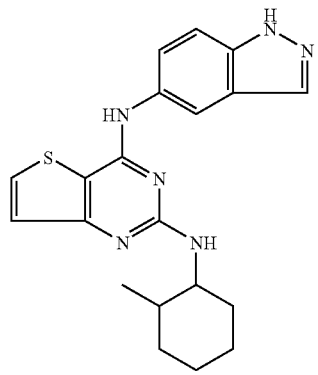
(136)
(137)
(138)
-continued
(139)
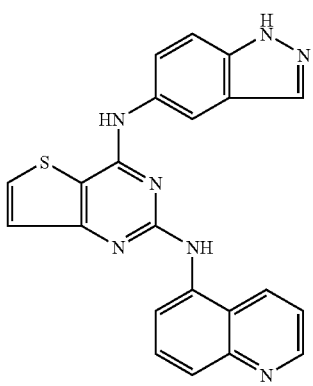
(140)
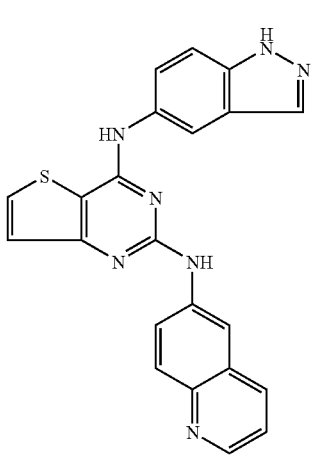
(141)
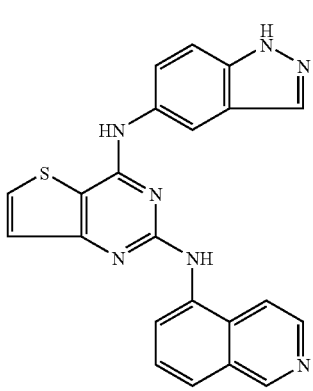
(142)
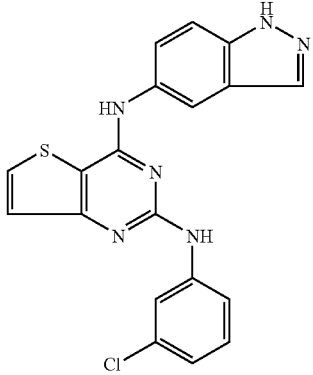

-continued
(143)
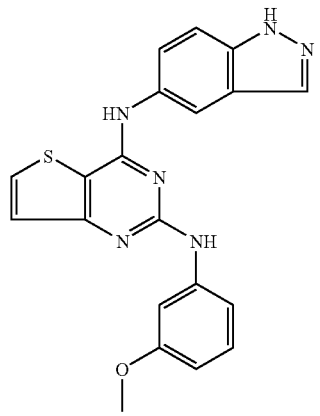
(144)
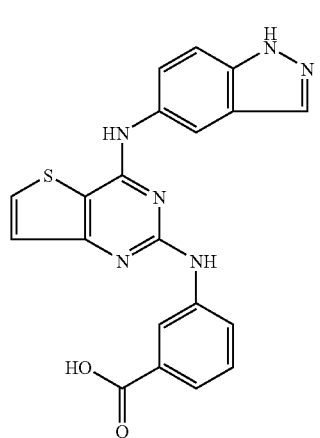
(145)
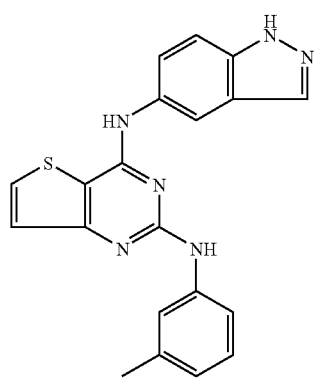
(146)
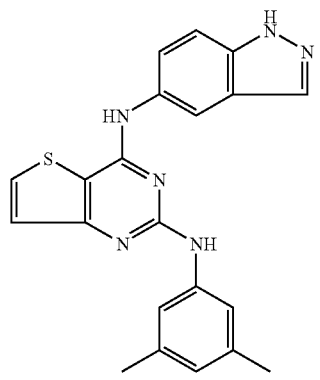
-continued
(147)
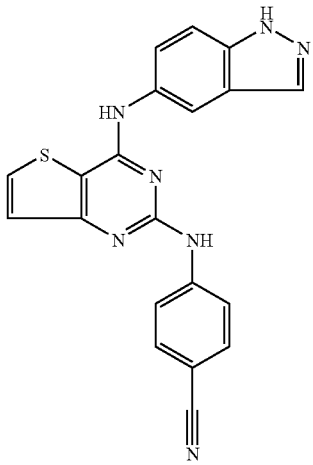
(148)
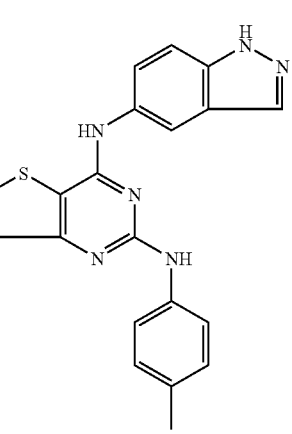
(149)
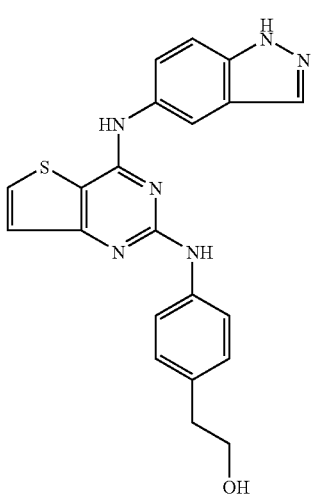

(150) 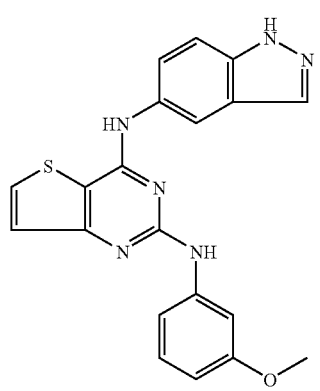
(151) 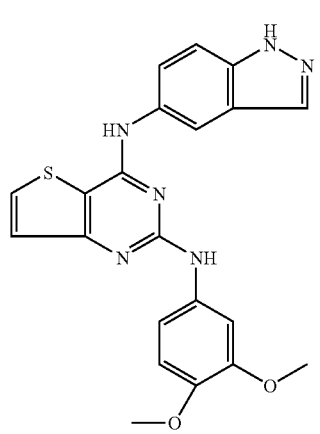
(152) 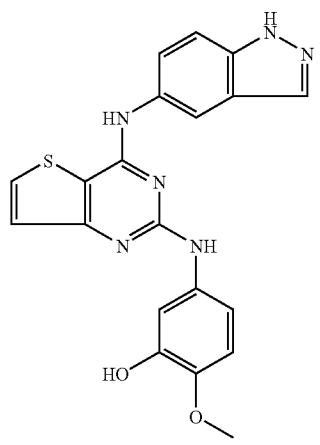
(153) 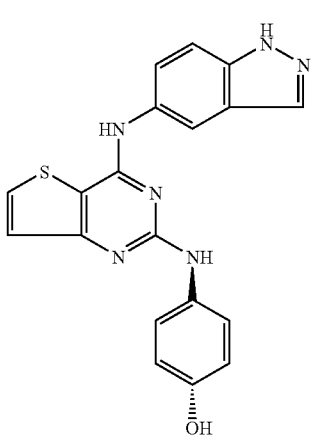
(154) 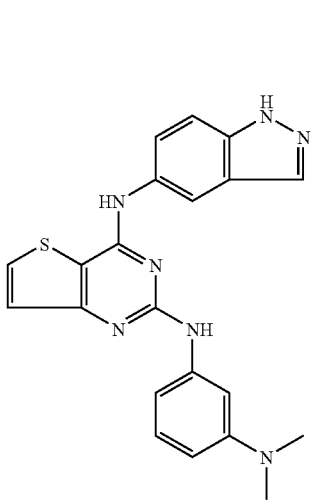
(155) 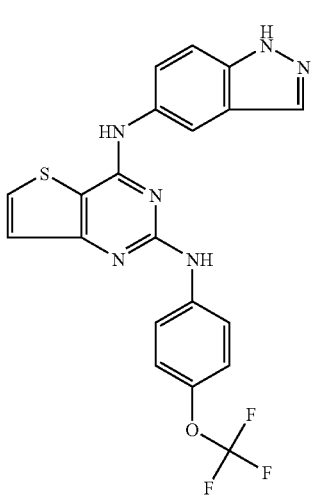

-continued
(156) 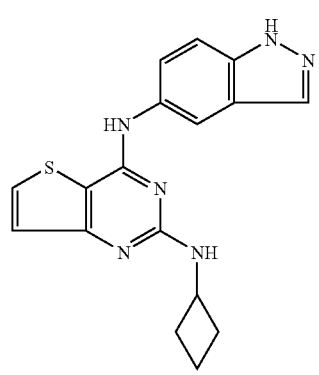
(157) 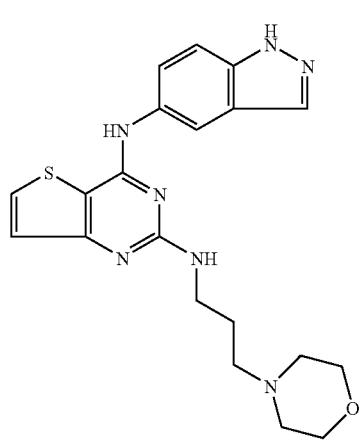
(158) 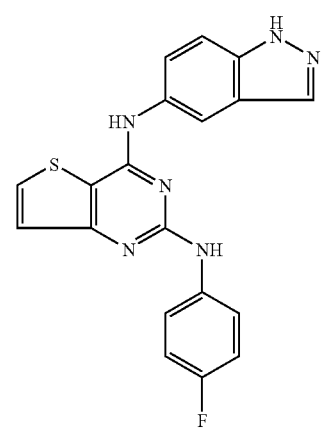
(159) 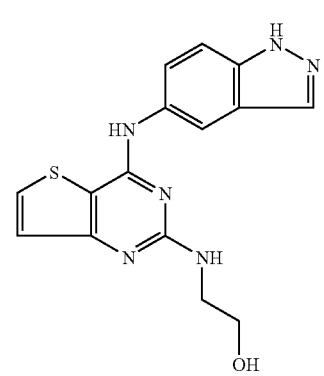
-continued
(160) 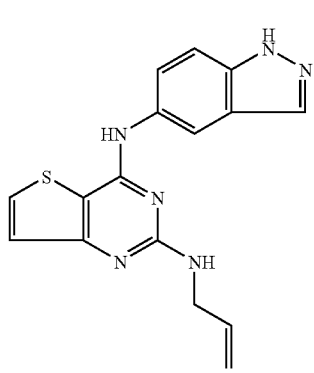
(161) 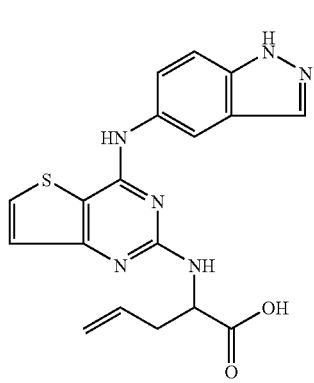
(162) 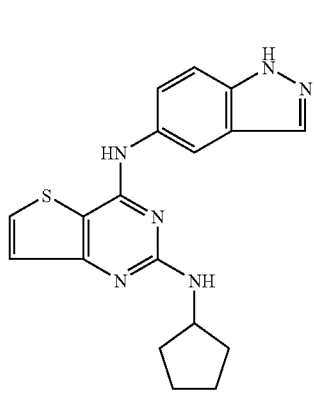
(163) 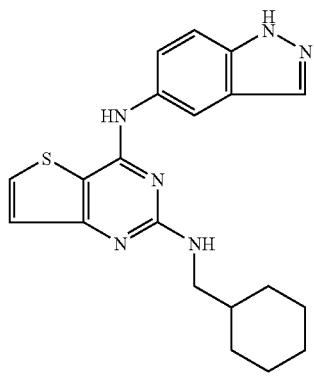

-continued
(164)
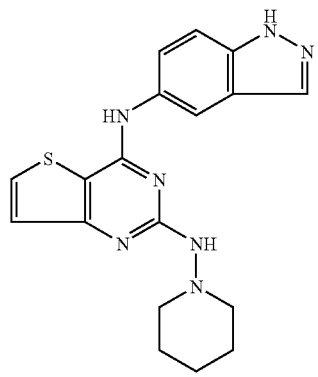
(165)
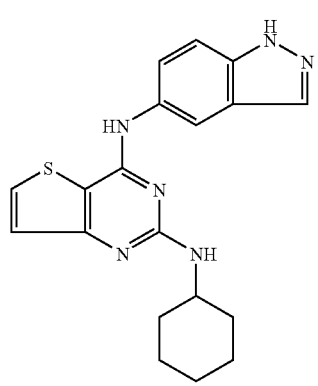
(166)
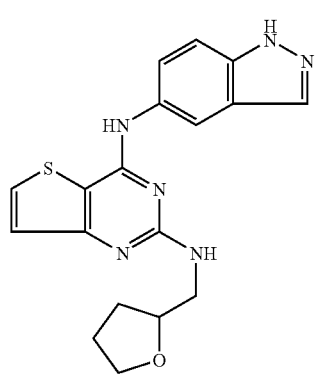
(167)
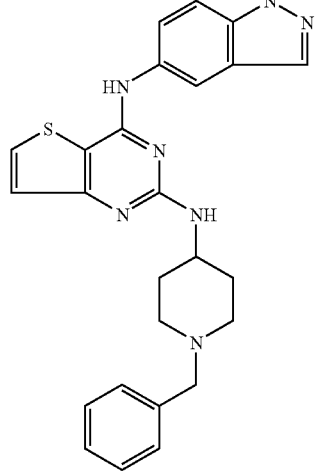
-continued
(168)
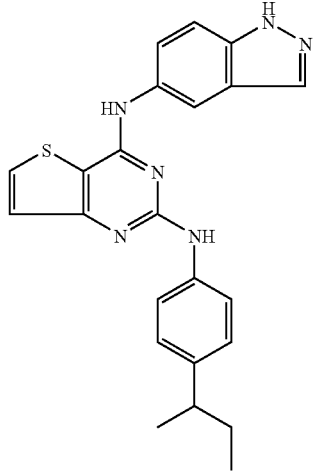
(169)
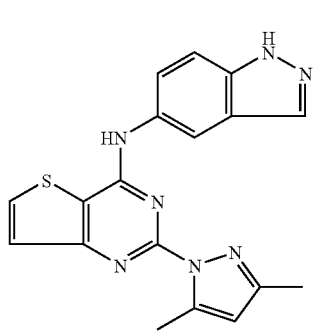
(170)
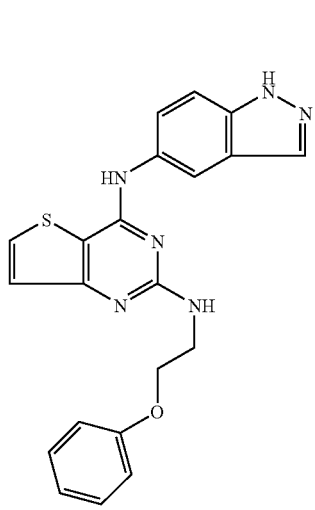

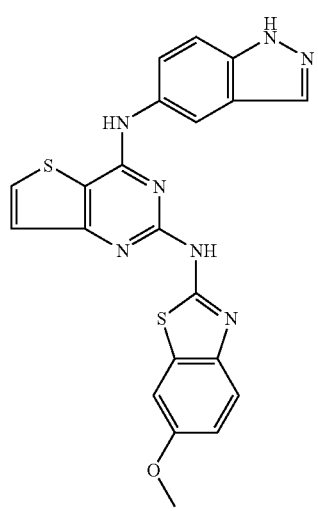
(171)
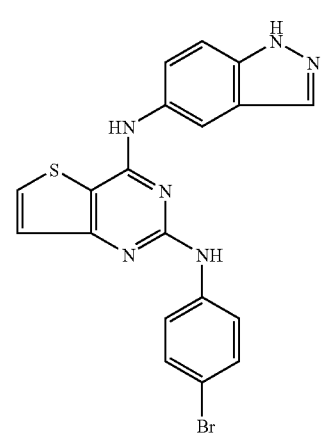
(172)
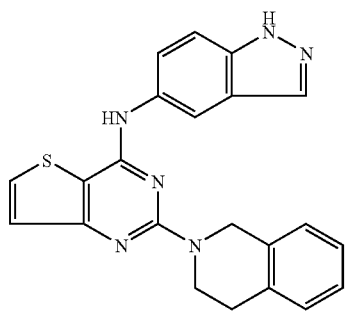
(173)
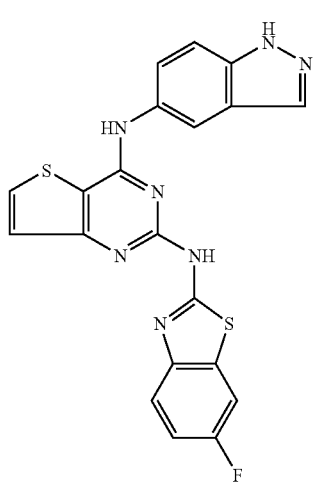
(174)
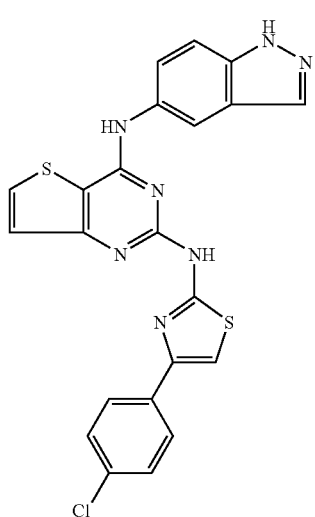
(175)
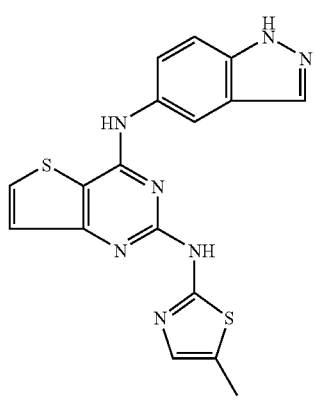
(176)

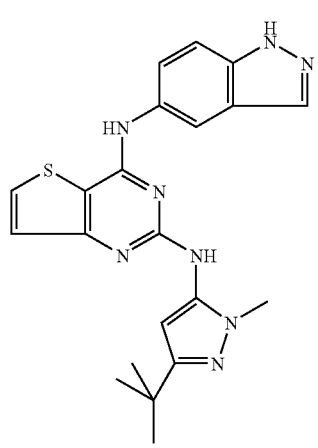
(177)
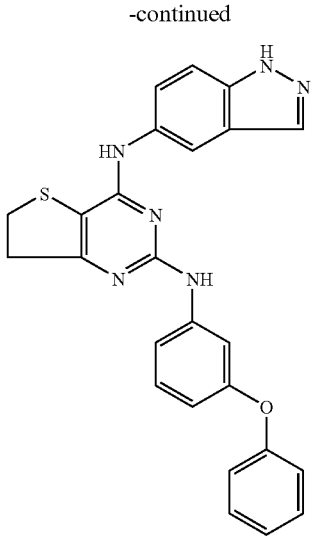
(180)
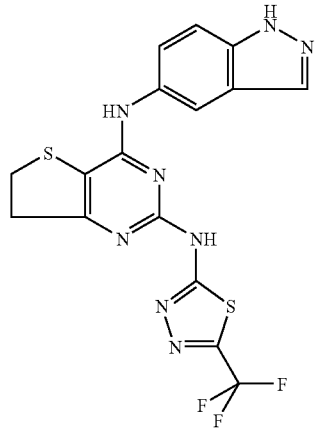
(178)
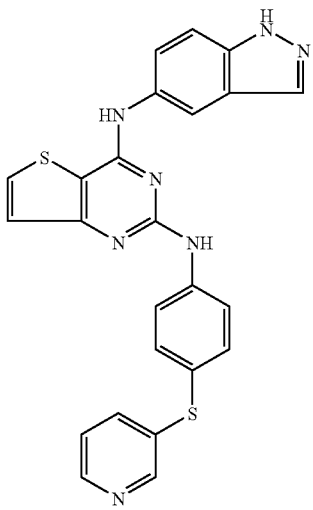
(181)
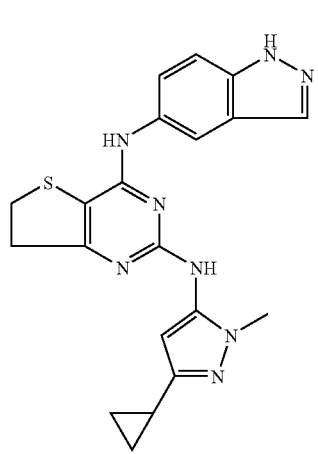
(179)
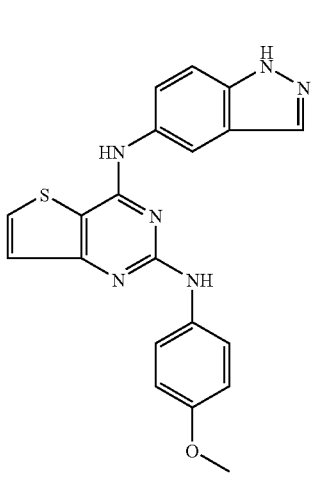
(182)

191
-continued
(183)
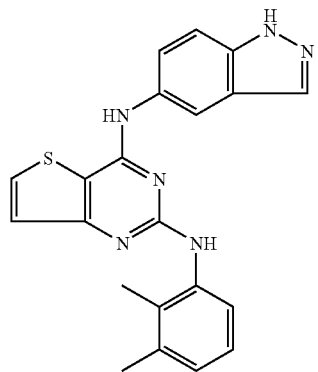
(184)
(185)
(186)
192
-continued
(187)
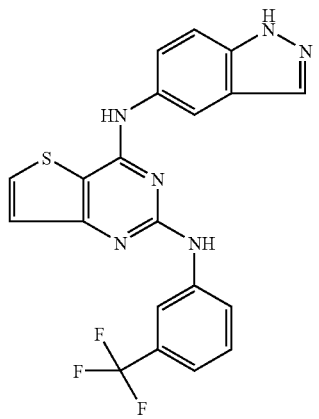
(188)
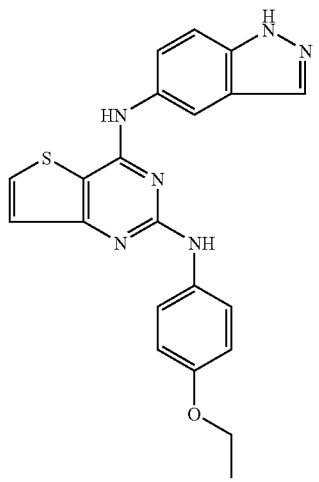
(189)
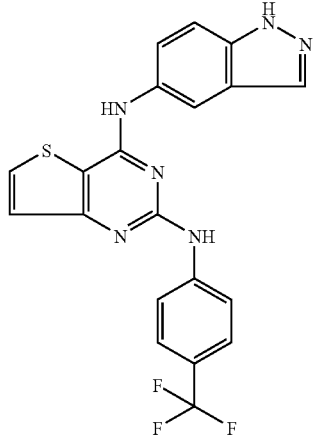

-continued
(190)
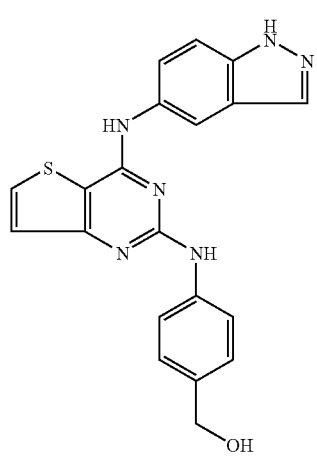
(191)
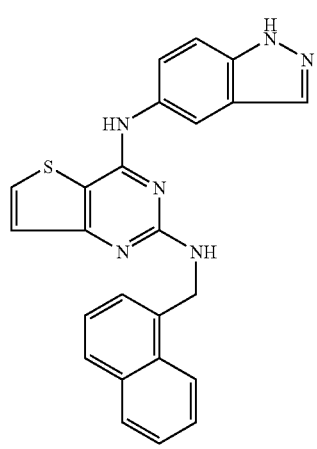
(192)
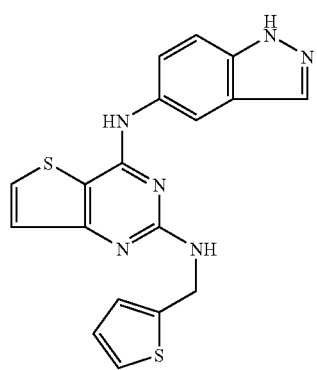
-continued
(193)
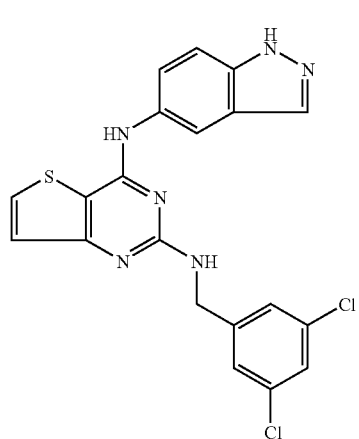
(194)
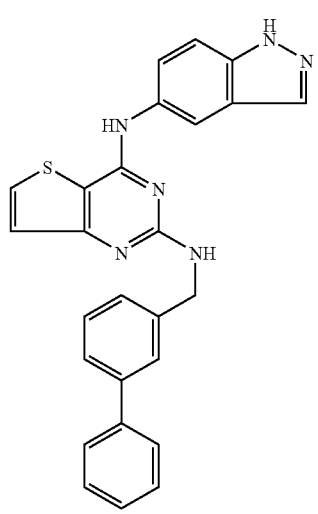
(195)
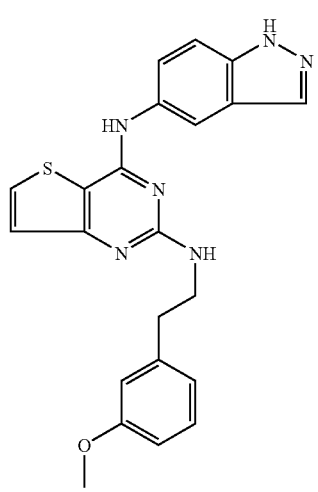

-continued
(196)
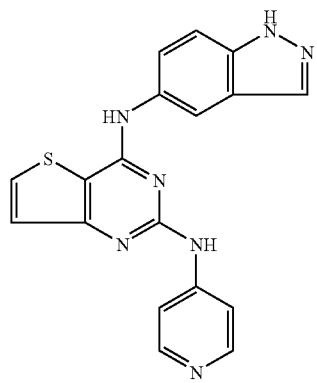
(197)
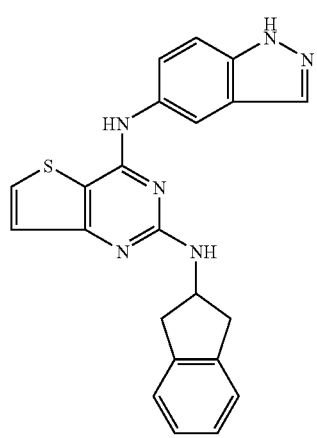
(198)
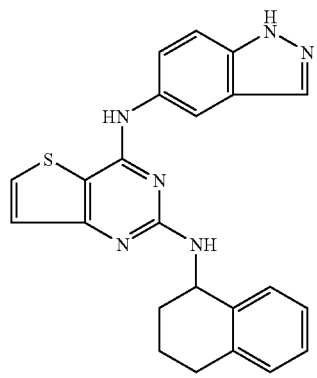
-continued
(199)
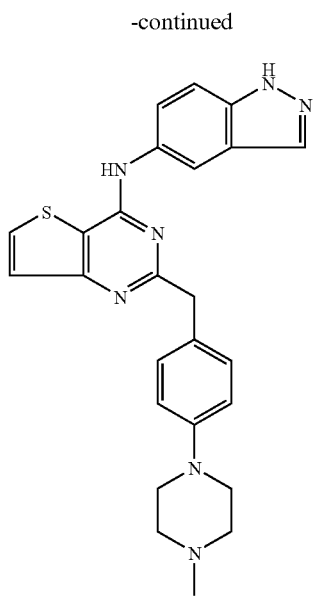
(200)
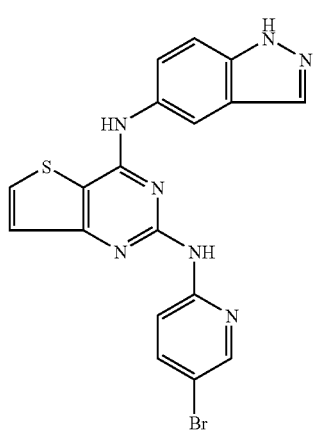
(201)
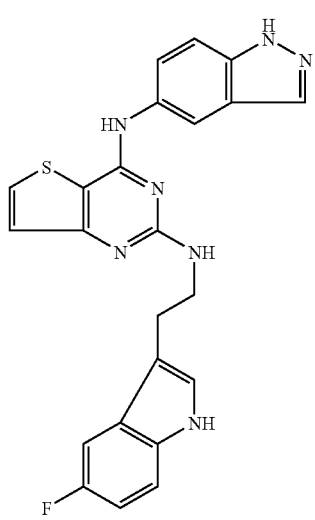

-continued
(202)
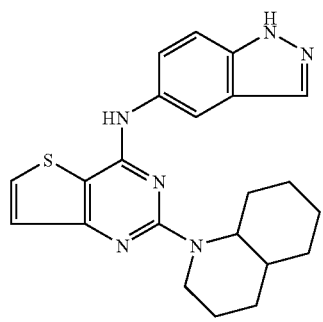
(203)
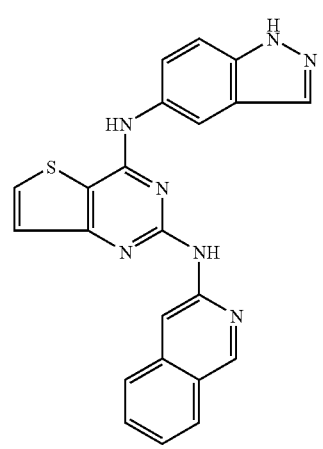
(204)
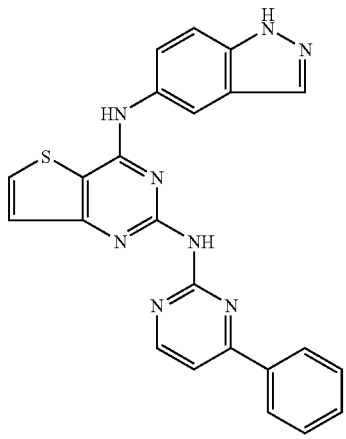
-continued
(205)
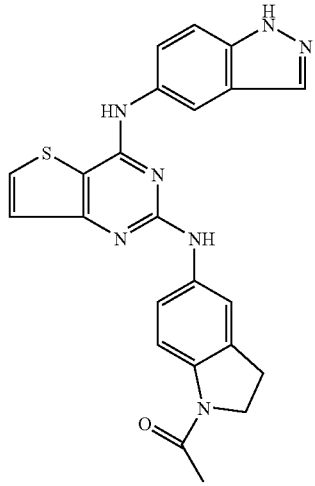
(206)
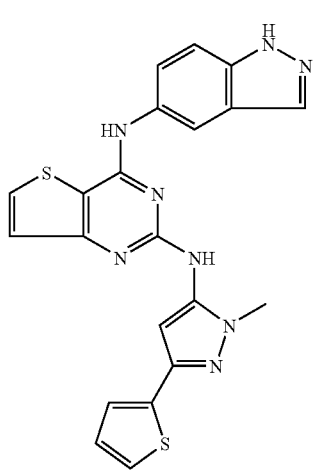
(207)
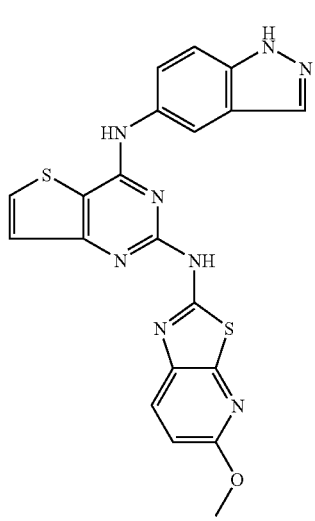

-continued
(208)
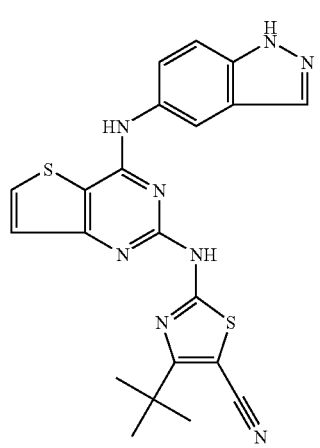
(209)
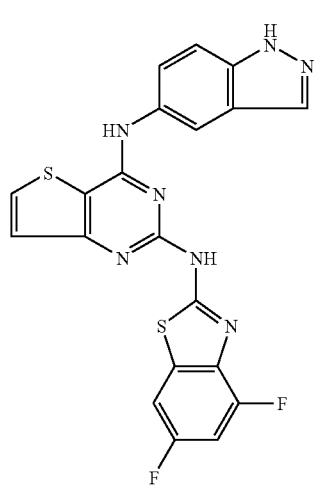
(210)
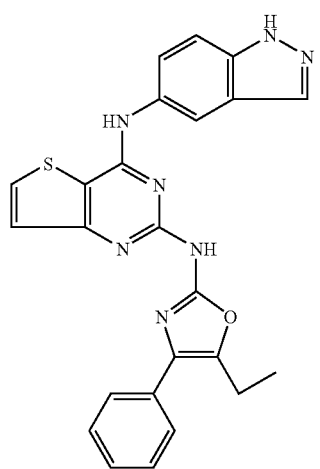
-continued
(211)
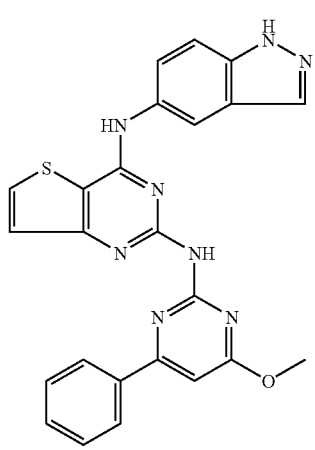
(212)
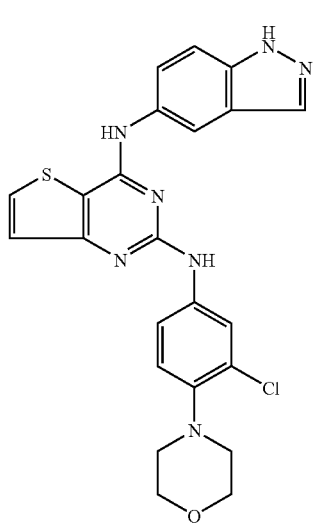
(213)
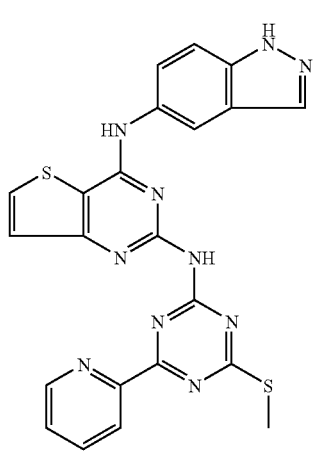

-continued
(214)
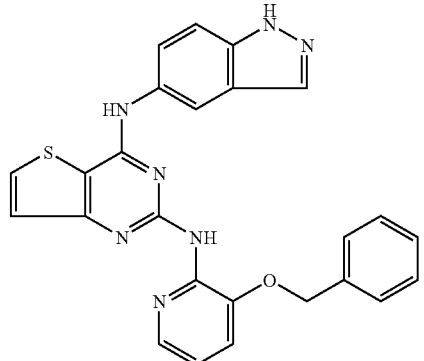
(215)
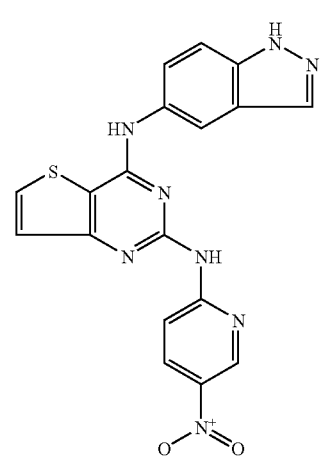
(216)
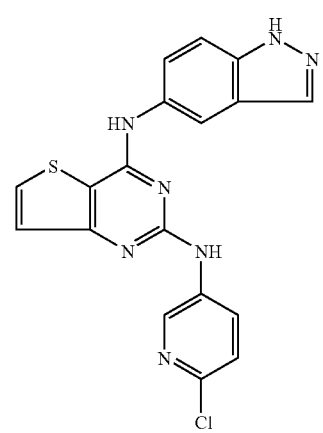
-continued
(217)
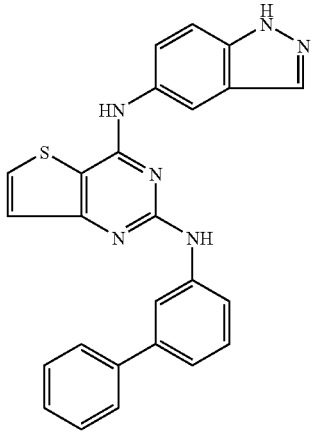
(218)
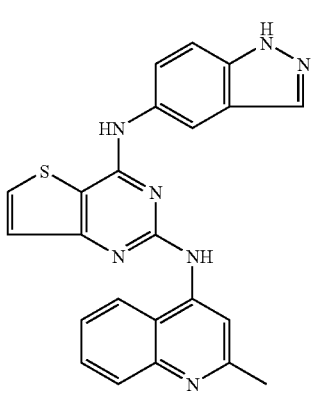
(219)
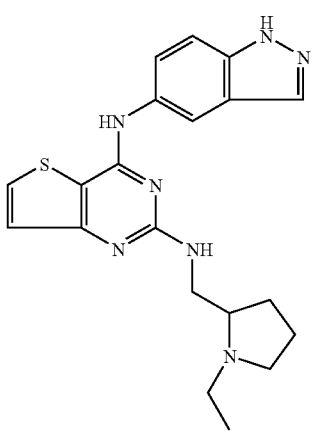

203
-continued
(220)
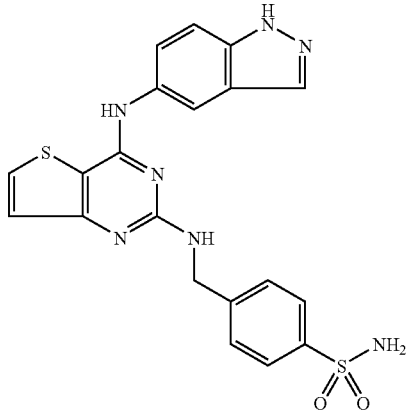
(221)
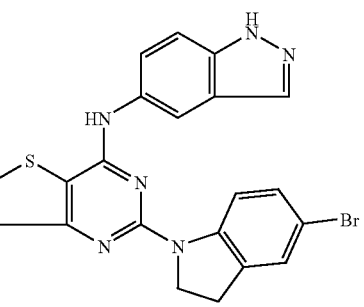
(222)
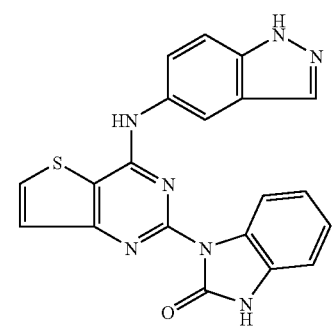
(223)
204
-continued
(224)
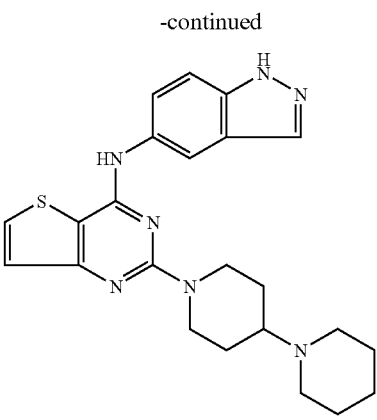
(225)
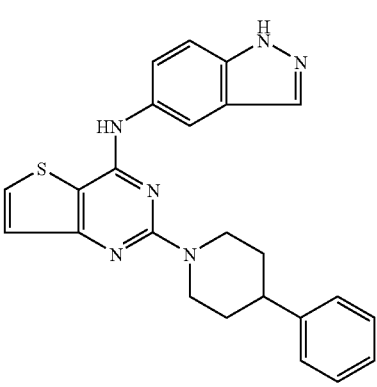
(226)
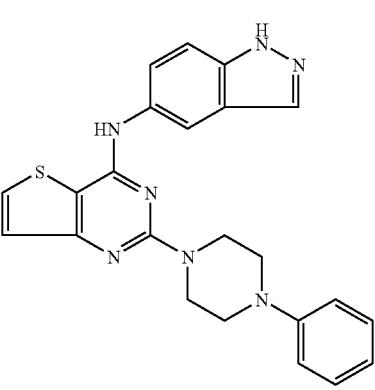
(227)
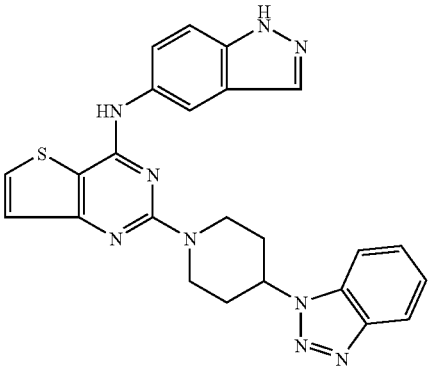

-continued

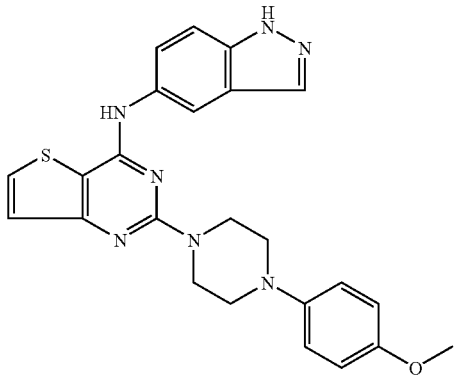

(228)

or a pharmaceutically acceptable salt thereof.

5. A method of treating hypertension, atherosclerosis, restenosis, cerebral ischemia, cerebral vasospasm, erectile dysfunction, comprising administering to host in need thereof a compound according to claim 4.

6. A method of treating hypertension, atherosclerosis, restenosis, cerebral ischemia, cerebral vasospasm, or erectile dysfunction, comprising administering to a host in need thereof a compound according to claim 1.

7. A method according to claim 5, wherein the host is a human.

8. A method according to claim 6, wherein the host is a human.

* * * * *